(12) United States Patent
Fujita et al.

(10) Patent No.: US 10,294,125 B2
(45) Date of Patent: *May 21, 2019

(54) FILTER MEDIUM, METHOD FOR PRODUCING FILTER MEDIUM, WATER TREATMENT MODULE, AND WATER TREATMENT DEVICE

(71) Applicants: MITSUBISHI MATERIALS CORPORATION, Tokyo (JP); Mitsubishi Materials Electronic Chemicals Co., Ltd., Akita-shi (JP)

(72) Inventors: Masato Fujita, Akita (JP); Masakazu Uotani, Akita (JP); Hiroshi Koshiyama, Akita (JP); Takeshi Kamiya, Akita (JP); Tsunetoshi Honda, Akita (JP); Daisuke Takano, Saitama (JP)

(73) Assignees: MITSUBISHI MATERIALS CORPORATION, Tokyo (JP); Mitsubishi Materials Electronic Chemicals Co., Ltd., Akita-shi (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/329,841

(22) PCT Filed: Jul. 30, 2015

(86) PCT No.: PCT/JP2015/071635
§ 371 (c)(1),
(2) Date: Jan. 27, 2017

(87) PCT Pub. No.: WO2016/017754
PCT Pub. Date: Feb. 4, 2016

(65) Prior Publication Data
US 2017/0247265 A1    Aug. 31, 2017

(30) Foreign Application Priority Data

Jul. 30, 2014 (JP) ................................. 2014-155553
Jul. 30, 2014 (JP) ................................. 2014-155554
(Continued)

(51) Int. Cl.
*C02F 1/40* (2006.01)
*B01D 17/04* (2006.01)
(Continued)

(52) U.S. Cl.
CPC ............... *C02F 1/40* (2013.01); *B01D 17/045* (2013.01); *B01D 17/10* (2013.01); *C09D 5/00* (2013.01);
(Continued)

(58) Field of Classification Search
CPC ......... B01D 17/045; B01D 17/10; C02F 1/40; C02F 2101/32; C08K 5/19; C08K 5/20;
(Continued)

(56) References Cited

U.S. PATENT DOCUMENTS 2,266,350 A    12/1941    Womack
3,471,484 A    10/1969    Guenthner
(Continued)

FOREIGN PATENT DOCUMENTS

CN    1805774 A    7/2006
GB    1512348 A    6/1978
(Continued)

OTHER PUBLICATIONS

English translation of Japanese Patent No. 4406700 B2 (2009).*
(Continued)

*Primary Examiner* — John Kim
(74) *Attorney, Agent, or Firm* — Locke Lord LLP

(57) ABSTRACT

The filter medium is a filter medium which uses a liquid containing oil and water as a separation target, and has a
(Continued)

channel for the liquid. The filter medium includes a base constituting the channel, and one or more of nitrogen-containing fluorine compounds which are provided on at least a portion of a surface of the channel. The nitrogen-containing fluorine compound includes an oil-repellency imparting group and any one hydrophilicity imparting group selected from a group consisting of an anion type, a cation type, and an amphoteric type, in a molecule.

15 Claims, 1 Drawing Sheet

(30) Foreign Application Priority Data

| Oct. 7, 2014 | (JP) | ................................. 2014-206782 |
| May 21, 2015 | (JP) | ................................. 2015-104023 |

(51) Int. Cl.

| C09D 129/14 | (2006.01) |
| C09D 167/00 | (2006.01) |
| C09D 201/00 | (2006.01) |
| C09D 5/00 | (2006.01) |
| C09D 7/63 | (2018.01) |
| B01D 17/00 | (2006.01) |
| D06M 13/408 | (2006.01) |
| D06M 13/438 | (2006.01) |
| D06M 13/46 | (2006.01) |
| C07C 303/02 | (2006.01) |
| C07C 303/22 | (2006.01) |
| C07C 303/40 | (2006.01) |
| C07C 309/04 | (2006.01) |
| C07C 311/03 | (2006.01) |
| C07C 311/10 | (2006.01) |
| C07C 227/08 | (2006.01) |
| C07C 227/18 | (2006.01) |
| C07C 229/06 | (2006.01) |
| C07C 231/12 | (2006.01) |
| C07C 233/36 | (2006.01) |
| C07C 233/37 | (2006.01) |
| C02F 101/32 | (2006.01) |
| C08K 5/19 | (2006.01) |
| C08K 5/20 | (2006.01) |
| C08K 5/3415 | (2006.01) |
| C08K 5/3462 | (2006.01) |
| C08K 5/357 | (2006.01) |
| C08K 5/42 | (2006.01) |
| C08K 5/435 | (2006.01) |

(52) U.S. Cl.
CPC ............ *C09D 7/63* (2018.01); *C09D 129/14* (2013.01); *C09D 167/00* (2013.01); *C09D 201/00* (2013.01); *D06M 13/408* (2013.01); *D06M 13/438* (2013.01); *D06M 13/461* (2013.01); *B01D 2239/0421* (2013.01); *B01D 2239/086* (2013.01); *C02F 2101/32* (2013.01); *C07C 227/08* (2013.01); *C07C 227/18* (2013.01); *C07C 229/06* (2013.01); *C07C 231/12* (2013.01); *C07C 233/36* (2013.01); *C07C 233/37* (2013.01); *C07C 303/02* (2013.01); *C07C 303/22* (2013.01); *C07C 303/40* (2013.01); *C07C 309/04* (2013.01); *C07C 311/03* (2013.01); *C07C 311/10* (2013.01); *C08K 5/19* (2013.01); *C08K 5/20* (2013.01); *C08K 5/3415* (2013.01); *C08K 5/3462* (2013.01); *C08K 5/357* (2013.01); *C08K 5/42* (2013.01); *C08K 5/435* (2013.01)

(58) Field of Classification Search
CPC .... C08K 5/3415; C08K 5/3462; C08K 5/357; C08K 5/42; C08K 5/435; C09D 129/14; C09D 167/00; C09D 201/00; C09D 5/00; C09D 7/1233; C09D 7/63; C07C 303/02; C07C 303/22; C07C 303/40; C07C 309/04; C07C 311/03; C07C 311/10; C07C 227/08; C07C 227/18; C07C 229/06; C07C 231/12; C07C 233/36; C07C 233/37; D06M 13/408; D06M 13/438; D06M 13/461
See application file for complete search history.

(56) References Cited

U.S. PATENT DOCUMENTS

| 4,859,754 | A | 8/1989 | Maekawa et al. |
| 5,443,724 | A | 8/1995 | Williamson et al. |
| 6,207,777 | B1 | 3/2001 | Shimada et al. |
| 2002/0004107 | A1 | 1/2002 | Rogers |
| 2009/0317621 | A1 | 12/2009 | Youngblood et al. |

FOREIGN PATENT DOCUMENTS

| GB | 2354458 A | | 3/2001 |
| JP | 45-002299 B | | 1/1970 |
| JP | 45-006006 B1 | | 2/1970 |
| JP | 46-031802 Y | | 11/1971 |
| JP | 49-040734 B1 | | 11/1974 |
| JP | 51-012462 A | | 1/1976 |
| JP | 51-012463 A | | 1/1976 |
| JP | 51-059133 U | | 5/1976 |
| JP | 52-021130 U | | 2/1977 |
| JP | 52-052182 A | | 4/1977 |
| JP | 52-074960 A | | 6/1977 |
| JP | 52-090861 A | | 7/1977 |
| JP | 53-109266 A | * | 9/1978 |
| JP | 53-111569 A | | 9/1978 |
| JP | 54-061362 A | | 5/1979 |
| JP | 60-139306 A | | 7/1985 |
| JP | 61-257211 A | | 11/1986 |
| JP | 62-035738 Y | | 9/1987 |
| JP | 63-037187 U | | 3/1988 |
| JP | 03-060791 A | | 3/1991 |
| JP | 03-144006 A | | 6/1991 |
| JP | 05-058970 A | | 3/1993 |
| JP | 05-137903 A | | 6/1993 |
| JP | 05-177766 A | | 7/1993 |
| JP | 05-272027 A | | 10/1993 |
| JP | 05-285305 A | | 11/1993 |
| JP | 05-329476 A | | 12/1993 |
| JP | 05-331455 A | | 12/1993 |
| JP | 06-134300 A | | 5/1994 |
| JP | 07-004535 U | | 1/1995 |
| JP | 07-024212 A | | 1/1995 |
| JP | 07-048464 A | | 2/1995 |
| JP | H07-204505 A | | 8/1995 |
| JP | 07-265605 A | | 10/1995 |
| JP | 07-284606 A | | 10/1995 |
| JP | 07-289801 A | | 11/1995 |
| JP | 08-243558 A | | 9/1996 |
| JP | 09-094401 A | | 4/1997 |
| JP | 09-227160 A | | 9/1997 |
| JP | 10-006973 A | | 1/1998 |
| JP | 10-007742 A | | 1/1998 |
| JP | 10-103816 A | | 4/1998 |
| JP | 10-204860 A | | 8/1998 |
| JP | 11-021866 A | | 1/1999 |
| JP | 11-114304 A | | 4/1999 |
| JP | 11-156104 A | | 6/1999 |
| JP | 11-244671 A | | 9/1999 |
| JP | 11-323812 A | | 11/1999 |

(56) References Cited

FOREIGN PATENT DOCUMENTS

| | | |
|---|---|---|
| JP | 2000-024656 A | 1/2000 |
| JP | 2000-096082 A | 4/2000 |
| JP | 2000-126505 A | 5/2000 |
| JP | 2000-189954 A | 7/2000 |
| JP | 2000-288303 A | 10/2000 |
| JP | 2000-342359 A | 12/2000 |
| JP | 2001-000960 A | 1/2001 |
| JP | 2001-004125 A | 1/2001 |
| JP | 2001-164450 A | 6/2001 |
| JP | 2001-220374 A | 8/2001 |
| JP | 2002-105433 A | 4/2002 |
| JP | 2002-113301 A | 4/2002 |
| JP | 2002-266329 A | 9/2002 |
| JP | 2003-166173 A | 6/2003 |
| JP | 2003-227117 A | 8/2003 |
| JP | 2003-267900 A | 9/2003 |
| JP | 2004-098047 A | 4/2004 |
| JP | 2004-230278 A | 8/2004 |
| JP | 2004-298711 A | 10/2004 |
| JP | 2005-074316 A | 3/2005 |
| JP | 2005-144436 A | 6/2005 |
| JP | 2005-330354 A | 12/2005 |
| JP | 2006-110452 A | 4/2006 |
| JP | 2006-130743 A | 5/2006 |
| JP | 2006-198483 A | 8/2006 |
| JP | 2006-200269 A | 8/2006 |
| JP | 2006-292326 A | 10/2006 |
| JP | 2007-144239 A | 6/2007 |
| JP | 2007-216184 A | 8/2007 |
| JP | 2007-326821 A | 12/2007 |
| JP | 2007-326836 A * | 12/2007 |
| JP | 2008-031511 A | 2/2008 |
| JP | 2008-062127 A | 3/2008 |
| JP | 2009-061376 A | 3/2009 |
| JP | 2009-127015 A | 6/2009 |
| JP | 2009-133173 A | 6/2009 |
| JP | 4406700 B2 | 2/2010 |
| JP | 2010-159563 A | 7/2010 |
| JP | 2010-201321 A | 9/2010 |
| JP | 2011-011172 A | 1/2011 |
| JP | 2013-188680 A | 9/2013 |
| JP | 2013-202569 A | 10/2013 |
| JP | 2014-036931 A | 2/2014 |
| JP | 2014-057920 A | 4/2014 |
| JP | 2014-148504 A | 8/2014 |
| JP | 2014-148670 A | 8/2014 |
| JP | 2014-158996 A | 9/2014 |
| KR | 10-2015-0001082 A | 1/2015 |
| WO | 97/036951 A1 | 10/1997 |
| WO | 2013/111372 A1 | 8/2013 |
| WO | 2013/145372 A1 | 10/2013 |

OTHER PUBLICATIONS

English translation of Japanese Patent Application No. 53-109266 (1978).*
English translation of Japanese Patent Application No. 2007-326836 (2007).*
International Search Report dated Oct. 20, 2015, issued for PCT/JP2015/071489 and English translation thereof.
International Search Report dated Oct. 20, 2015, issued for PCT/JP2015/071635 and English translation thereof.
International Search Report dated Oct. 20, 2015, issued for PCT/JP2015/071680 and English translation thereof.
International Search Report dated Oct. 27, 2015, issued for PCT/JP2015/071684 and English translation thereof.
International Search Report dated Oct. 20, 2015, issued for PCT/JP2015/071544 and English translation thereof.
International Search Report dated Oct. 27, 2015, issued for PCT/JP2015/071661 and English translation thereof.
Search Report dated Jan. 4, 2018, issued for the European Patent Application No. 15827683.2.
Search Report dated Jan. 8, 2018, issued for the European Patent Application No. 15827639.4.
Search Report dated Jan. 15, 2018, issued for the European Patent Application No. 15827185.8.
Office Action dated May 15, 2018, issued for the Chinese patent application No. 201580041432.X and a partial English translation of the Search Report.
Office Action dated Jul. 24, 2018, issued for the Japanese patent application No. 2015-013505 and English translation thereof.
Office Action dated Jul. 24, 2018, issued for the Japanese patent application No. 2015-013696 and English translation thereof.
Office Action dated Aug. 21, 2018, issued for the Japanese patent application No. 2014-238242 and English translation thereof.
Office Action dated Aug. 21, 2018, issued for the Japanese patent application No. 2014-256646 and English translation thereof.
Office Action dated Sep. 11, 2018, issued for the Japanese patent application No. 2015-009441 and English translation thereof.
Office Action dated Sep. 11, 2018, issued for the Japanese patent application No. 2015-013699 and English translation thereof.
Office Action dated Nov. 20, 2018, issued for the Japanese patent application No. 2015-013695 and English translation thereof.
Office Action dated Sep. 25, 2018, issued for the Japanese patent application No. 2015-007194 and English translation thereof.
Office Action dated Sep. 25, 2018, issued for the Japanese patent application No. 2015-009440 and English translation thereof.
Office Action dated Feb. 26, 2019, issued for the Japanese patent application No. 2015-084239 and English translation thereof.
Office Action dated Feb. 26, 2019, issued for the Japanese patent application No. 2015-086020 and English translation thereof.
Office Action dated Feb. 26, 2019, issued for the Japanese patent application No. 2015-105865 and English translation thereof.
Notice of Allowance dated Mar. 5, 2019, issued for the Japanese patent application No. 2015-147198 and English translation thereof.

* cited by examiner

FILTER MEDIUM, METHOD FOR PRODUCING FILTER MEDIUM, WATER TREATMENT MODULE, AND WATER TREATMENT DEVICE

CROSS REFERENCE TO RELATED APPLICATIONS

This application is related to three co-pending applications: "OIL-WATER SEPARATION APPARATUS AND DRAINAGE SYSTEM" filed Jan. 26, 2017, U.S. Ser. No. 15/329,393 in the names of Kosei SATO; Masato FUJITA; Masakazu UOTANI; Hiroshi KOSHIYAMA; Takeshi KAMIYA; Tsunetoshi HONDA; Hiroyuki IMAI and Daisuke TAKANO as a national phase entry of PCT/JP2015/071544; "HYDROPHILIC OIL REPELLENT AND PRODUCTION METHOD OF SAME, SURFACE COATING MATERIAL, COATING FILM, RESIN COMPOSITION, OIL-WATER SEPARATION FILTER MATERIAL, AND POROUS BODY" filed Jan. 26, 2017, U.S. Ser. No. 15/329,408 in the names of Masato FUJITA; Masakazu UOTANI; Takeshi KAMIYA; Tsunetoshi HONDA and Daisuke TAKANO as a national phase entry of PCT/JP2015/071489; and "SURFACE COATING MATERIAL, COATING FILM, AND HYDROPHILIC OIL REPELLENT MEMBER" filed Jan. 26, 2017, U.S. Ser. No. 15/329,426 in the names of Masakazu UOTANI; Hiroshi KOSHIYAMA; Takeshi KAMIYA; Tsunetoshi HONDA; Kosei SATO; Masato FUJITA and Daisuke TAKANO as a national phase entry of PCT/JP2015/071661; which applications are assigned to the assignee of the present application and all three incorporated by reference herein.

TECHNICAL FIELD

The present invention relates to a filter medium, a method for producing the filter medium, a water treatment module, and a water treatment device.

Priority is claimed on Japanese Patent Application Nos. 2014-155553 and 2014-155554, filed on Jul. 30, 2014; Japanese Patent Application No. 2014-206782, filed on Oct. 7, 2014; and Japanese Patent Application No. 2015-104023, filed on May 21, 2015, the content of which is incorporated herein by reference.

BACKGROUND ART

Conventionally, oils and fats such as oil or lard are mixed and contained in water discharged from, for example, a general house, a commercial cooking place, or a building, or water discharged from a conduit for a sewage or waste liquid treatment facility of public establishment. Such discharged water is the cause of clogging of a sewerage pipe by fixation of the oil, or the cause of an occurrence of an odor. In addition, there are also problems in that the function of the public sewerage facility is hindered or an oil clot (white solid matter) from a sewerage facility is spilled to a harbor after heavy rain, for example. Thus, in each district, measures in that restaurant companies are caused to install a gathering machine which separates and collects oils and fats in discharged water, and thus oils and fats are not spilled to the sewerage are also performed.

Treatment of separating an oil-water mixed liquid into oil and water is performed as waste liquid treatment in, for example, food manufacturing, fiber treatment, mechanical processing, and petroleum refining, and as an oil collection work performed in a case where an oil is spilled into a river, the sea, and the like due to, for example, an accident.

In addition, for example, when crude oil is minded, a method in which the seawater is injected to an oil layer of a stratum, and pressure of non-aqueous oil is increased, and thus an output is ensured is generally performed. "Water accompanying in the oil field" which is water used in such minding of crude oil contains a large amount of non-aqueous oil. Thus, treatment of removing the non-aqueous oil is performed, and then the non-aqueous oil is scrapped. However, because the non-aqueous oil is the cause of contaminating the ocean, lakes and marshes, and the like, recently, restrictions for the content of the non-aqueous oil in discharged water is reinforced. In a country or a district in which the restrictions are strongest, the content of the non-aqueous oil is required to be less than 5 mg/L.

As the conventional oil-water separation method, for example, the following methods are known: separation by using a flocculant; adhering and separation; centrifugation; pressure floatation separation; an electrolysis floatation method; coarsely granulation and separation by using a coalescer (for example, see Patent Document 1); and separation by microbial degradation.

In a case of a separation method using a flocculant, there is a problem in that expenses are continuously required, and treatment of filtered agglutinates also takes much labor and cost. A case by a machine such as a centrifuge and a case by pressure floatation separation may be effective for treating a large amount or for large-size utilities. However, the above cases have a problem in that it is difficult to be provided in a limited space. In the electrolysis floatation method, there is a problem in that complex control, for example, changing an applied power in accordance with electrical conductivity and the treated amount of a treatment liquid is required for stably performing oil-water separation. In the coalescer method, a filter having a network structure of ultrafine fiber is used. Thus, there is a problem in that clogging normally occurs in maintenance management. In a separation method using a microorganism, there is a problem in that it takes time, and maintenance is serious.

Water treatment by using a separation membrane which uses a porous film is performed in the related art. As oil-water separation, a reverse osmosis method, an ultrafiltration method, a precise filtration method (for example, see Patent Document 2), and the like are also known.

However, because oil and water is separated by using a hole diameter of the separation membrane in the reverse osmosis method, the ultrafiltration method, and the precise filtration method, there is a problem in that a membrane permeation flux is small. Further, in the process of performing water treatment, a separation target substance such as oil, which is provided in raw water adheres to the separation membrane, and thus fouling (clogging) occurs. A problem in that it is necessary that physical washing such as back pressure washing and air scrubbing is periodically performed occurs due to the fouling. Thus, improvement of difficulty in adhering oil (antifouling properties) or easiness of removing adhered oil (easy washing properties) is desired for the separation membrane using a porous film, in order to continuously use the separation membrane for a long term.

Various technologies are opened to the public for improving anti-fouling properties (clogging prevention properties). For example, a non-adhesiveness and hydrophilic hollow-fiber porous film is known. The non-adhesiveness and hydrophilic hollow-fiber porous film is formed from copolymer of polyolefin or olefin and halogenated olefin or polyvinylidene fluoride. In the non-adhesiveness and hydrophilic hollow-fiber porous film, a lateral chain including a neutral hydroxyl group is grafted to the surface of a pore in a hollow-fiber porous film, and a neutral hydroxyl group is provided. A hydrophilic fluorine finely-porous film and a water treatment method using the film are known. The hydrophilic fluorine finely-porous film is formed from fluoropolymer subjected to ozone treatment. Further, a polysulfone hollow-fiber membrane formed by polysulfone and blend of a polyvinyl acetal resin and a hydrophilic polymeric substance is known. Further, a method of applying a surfactant to a porous film which contains a polyvinylidene fluoride resin is known. The surfactant has a polyoxyalkylene structure, a fatty acid ester structure, and a hydroxyl group. A method (for example, see Patent Document 3) of performing hydrophilization treatment on a polyethersulfone porous film is known. In the hydrophilization treatment, discharging treatment is performed under vacuum while a gas mixture including a hexafluoropropylene gas and an oxygen gas flows.

However, even with the well-known technologies as described above, improvement of the anti-fouling properties may be insufficient. In a case where the above technology is used in, for example, oil-water separation, there is a problem in that oil easily adheres to a film surface, and this is the cause of decreasing a flow rate.

PRIOR ART LITERATURE

Patent Documents

[Patent Document 1] Japanese Unexamined Patent Application, First Publication No. 2006-198483
[Patent Document 2] Japanese Unexamined Patent Application, First Publication No. H5-137903
[Patent Document 3] Japanese Unexamined Patent Application, First Publication No. 2008-062127

DISCLOSURE OF INVENTION

Problems to be Solved by the Invention

Considering the above circumstances, an object of the present invention is to provide a filter medium which allows oil-water separation and has exceptional antifouling properties, easy washing properties, and anti-fouling properties, and to provide a method for producing the filter medium. Another object of the present invention is to provide a water treatment module and a water treatment device including the filter medium.

Means for Solving the Problems

In a case where a compound having a perfluoroalkyl group in a molecule is used as a surface treatment agent, the treated-surface normally shows water-repellent and oil-repellent properties, and water repellent properties are generally improved as the number of carbon atoms in a fluorine structure is increased. However, as a result obtained by the inventors performing close examination, the inventors found that unusual characteristics (of which realizing in the conventional nitrogen-containing fluorine compound was not possible) referred to as hydrophilic and oil-repellent properties are provided in a compound obtained by adding a hydrophilicity imparting group to a specific nitrogen-containing fluorine compound, among compounds having a perfluoroalkyl group which is bonded to fluorine and has carbon atoms of which the number is 4 to 18, and particularly exceptional hydrophilicity and exceptional oil repellent properties are also simultaneously shown in a compound having a fluorine structure in which the number of carbon atoms is large. Then, the inventors complete the present invention.

That is, the present invention has the following configuration.

[1] A filter medium which uses a liquid containing oil and water as a separation target, and has a channel for the liquid. The filter medium includes a base constituting the channel, and one or two types or more of nitrogen-containing fluorine compounds which are provided on at least a portion of a surface of the channel and are represented by the following formulas (1) to (4).

[Chemical Formula 1]

(1)

[Chemical Formula 2]

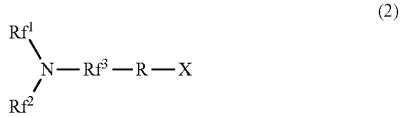

(2)

[Chemical Formula 3]

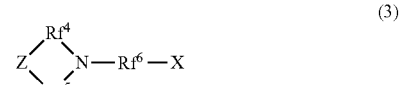

(3)

[Chemical Formula 4]

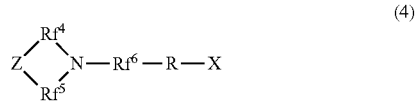

(4)

In the formulas (1) and (2), each of $Rf^1$ and $Rf^2$ is a straight-chain or branched perfluoroalkyl group which is the same as or different from each other, and has 1 to 6 carbon atoms. $Rf^3$ is a straight-chain or branched perfluoroalkylene group which has 1 to 6 carbon atoms.

In the formulas (3) and (4), each of $Rf^4$, $Rf^5$, and $Rf^6$ is a straight-chain or branched perfluoroalkylene group which is the same as or different from each other, and has 1 to 6 carbon atoms. Z includes any of an oxygen atom, a nitrogen atom, a $CF_2$ group, and a CF group.

In the formulas (2) and (4), R is a linking group which is a bivalent organic group.

In the formulas (1) to (4), X is any one hydrophilicity imparting group selected from a group consisting of an anion type, a cation type, and an amphoteric type in the above formulas.

In the filter medium of [1], the channel is formed by the base. Thus, the filter medium of [1] is a filter medium which uses a liquid containing water and oil as a separation target, and has a channel for the liquid. In the filter medium, the channel is formed by the base, and one or two types or more of nitrogen-containing fluorine compounds represented by the formulas (1) to (4) are provided on the surface of the channel.

Further, the filter medium of [1] may be used as an oil-water separating member. Thus, the filter medium of [1]

is an oil-water separating member which uses a liquid containing water and oil as a separation target, and has a channel for the liquid. An oil-water separating member in which the channel is formed by the base, and one or two types or more of nitrogen-containing fluorine compounds represented by the formulas (1) to (4) are provided on the surface of the channel is included in the filter medium.

[2] In the filter medium of [1], the one or more of nitrogen-containing fluorine compounds are bonded to the surface of the channel by one or both of an organic binder and an inorganic binder.

[3] In the filter medium of [2], the organic binder contains any of a thermoplastic resin, a thermoplastic elastomer, a thermosetting resin, an UV curable resin.

[4] In the filter medium of [2], the inorganic binder contains any of a silane compound and water glass.

[5] In the filter medium of any of [1] to [4], the base is an organic matter.

[6] In the filter medium of any of [1] to [4], the base is an inorganic matter.

[7] In the filter medium of any of [1] to [4], the base is a composite of an organic matter and an inorganic matter.

[8] In the filter medium of any of [1] to [4], the base is a fiber assembly and the channel is configured by a gap between fibers.

[9] In the filter medium of [8], the fiber includes an organic fiber selected from a group consisting of synthetic fiber, natural fiber, and cellulosic fiber, or an inorganic fiber selected from a group consisting of metallic fiber, carbon fiber, glass fiber, and ceramics fiber.

[10] In the filter medium of [8], the base is any of filter paper, woven fabric, knitted fabric, and nonwoven fabric.

[11] In the filter medium of any of [1] to [4], the base is an aggregate of particles. The channel is configured by a gap between the particles.

[12] In the filter medium of [11], the particle includes an inorganic particle selected from a group consisting of anthracite, sand, gravel, garnet, glass, ceramics, and metal.

[13] In the filter medium of any of [1] to [4], the base is a porous medium having a continuous pore. The channel is configured by the continuous pore.

[14] In the filter medium of [13], the porous medium is an organic porous medium selected from a group consisting of porous fluororesin, porous polypropylene, porous polyethylene, porous polyester, porous polysulfone, porous polyethersulfone, porous vinylon, porous nylon, porous polyvinyl alcohol, porous vinyl copolymer containing polyalkylene oxide chain, porous cellulose, or an inorganic porous medium selected from a group consisting of active carbon, ceramics, sintered metal, silica, alumina, zeolite, calcium carbonate, and clay mineral.

[15] In the filter medium of any of [1] to [14], the base is a base having hydrophilicity.

[16] In the filter medium of [15], the base is formed of a polymeric material in which one or more functional group which has hydrophilicity and is selected from a group consisting of a hydroxyl group, a carboxyl group, an amino group, a ketone group, and a sulfone group is introduced by a chemical reaction.

[17] In the filter medium of [15], the base is an organic matter in which the surface of polymer is subjected to hydrophilization by a finishing agent which is any of polyethylene glycol, polycarboxylic acid, polyisocyanate, a vinyl group, a glycidyl ether group, polyamine, polyalkylene oxide containing N-methoxymethylol, a polymeric electrolyte, and a cellulose-based substance having hydrophilicity.

[18] In the filter medium of [15], the base is any of a fluororesin, polypropylene resin, and polyethylene resin of which the surface is treated by any one or two or more of plasma treatment, corona treatment, and ozone treatment.

[19] In the filter medium of [1], a composite of the nitrogen-containing fluorine compound and an inorganic compound having charges or an ionic group is fixed onto the surface of the channel.

[20] In the filter medium of [19], the inorganic compound is a mixture of any one or more of a group consisting of fumed silica, colloidal silica, mullite, alumina, and zeolite.

[21] In the filter medium of [19], the inorganic compound is a mixture of any one or more of a group consisting of bentonite, organic bentonite, smectite, and kaolinite.

[22] In the filter medium of [19], the inorganic compound is polyaluminium chloride or ferric polysulfate.

[23] In the filter medium of [1], a composite of the nitrogen-containing fluorine compound and a fluorine resin particle is fixed onto the surface of the channel.

[24] In the filter medium of any of [19] to [23], the composite is bonded to the surface of the channel by one or both of an organic binder and an inorganic binder.

[25] In the filter medium of [24], the organic binder contains any of a thermoplastic resin, a thermoplastic elastomer, a thermosetting resin, an UV curable resin.

[26] In the filter medium of [24], the inorganic binder contains any of a silane compound and water glass.

[27] In the filter medium of any of [1] to [26], the width of the channel is 0.1 to 180 μm.

[28] In the filter medium of any of [1] to [27], when 45 μL of water is dropped, the dropped water is permeated into the base within 300 seconds.

[29] In the filter medium of any of [1] to [28], the nitrogen-containing fluorine compound is manufactured by a producing method in which carboxylic acid halide or sulfonic acid halide which has a nitrogen-containing perfluoroalkyl group represented by the following formula (5) or (6) is used as a raw material.

[Chemical Formula 5]

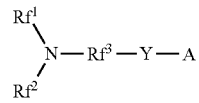

(5)

[Chemical Formula 6]

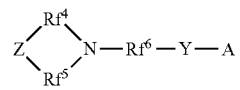

(6)

Each of $Rf^1$ and $Rf^2$ in the formula (5) is a straight-chain or branched perfluoroalkyl group which is the same as or different from each other, and has 1 to 6 carbon atoms. $Rf^3$ is a straight-chain or branched perfluoroalkylene group which has 1 to 6 carbon atoms.

Each of $Rf^4$, $Rf^5$, and $Rf^6$ in the formula (6) is a straight-chain or branched perfluoroalkylene group which is the same as or different from each other, and has 1 to 6 carbon atoms. Z includes any of an oxygen atom, a nitrogen atom, a $CF_2$ group, and a CF group.

Y in the formulas (5) and (6) is CO or $SO_2$.

In the formulas (5) and (6), A is any one halogen atom selected from a group consisting of fluorine, chlorine, bromine, and iodine.

[30] A method of manufacturing the filter medium described in [1], the method includes a process of preparing a coating liquid in which one or more nitrogen-containing fluorine compounds represented by the formulas (1) to (4) are dispersed or dissolved in water, an organic solvent, or a solvent mixture of water and an organic solvent; a process of coating at least a portion of the surface of the base with the coating liquid in which the nitrogen-containing fluorine compound is dispersed or dissolved; and a process of removing a dispersion medium or a solvent by drying, and forming a coating film on at least a portion of the surface of the base.

[31] In the method for producing a filter medium described in [30], the coating liquid contains an organic binder or an inorganic binder.

[32] A water treatment module includes the filter medium described in any of [1] to [29].

[33] A water treatment device includes the water treatment module described in [32].

Effects of the Invention

In the filter medium according to the present invention, one or more of nitrogen-containing fluorine compound in which an oil-repellency imparting group and a hydrophilicity imparting group are contained in a molecule is provided in the surface of the channel configured by the base. Thus, oil-water separation is possible, and antifouling properties, the easy washing properties, and the anti-fouling properties are exceptional.

If the channel is formed by the base having hydrophilicity, the nitrogen-containing fluorine compound is sufficiently held in the channel. Thus, persistence of an effect of oil-water separation performance and the like is exceptional.

The surface of the base is coated with a coating liquid in which one or more of the above-described nitrogen-containing fluorine compounds are dispersed or dissolved in water, an organic solvent, or a solvent mixture of water and an organic solvent, further a coating liquid obtained by providing a binder in the above coating liquid, by using the method for producing a filter medium according to the present invention. Then, the dispersion medium or the solvent is removed by drying, and thus it is possible to form a coating film on the surface of the base. Thus, it is possible to manufacture a filter medium in which a nitrogen-containing fluorine compound is strongly held in the surface of the base.

Since the water treatment module and the water treatment device according to the present invention include the above-described filter medium, oil-water separation is possible. The antifouling properties, the easy washing properties, and the anti-fouling properties are exceptional, and persistence of these effects is also exceptional.

BEST MODE FOR CARRYING OUT THE INVENTION

Figure 1:
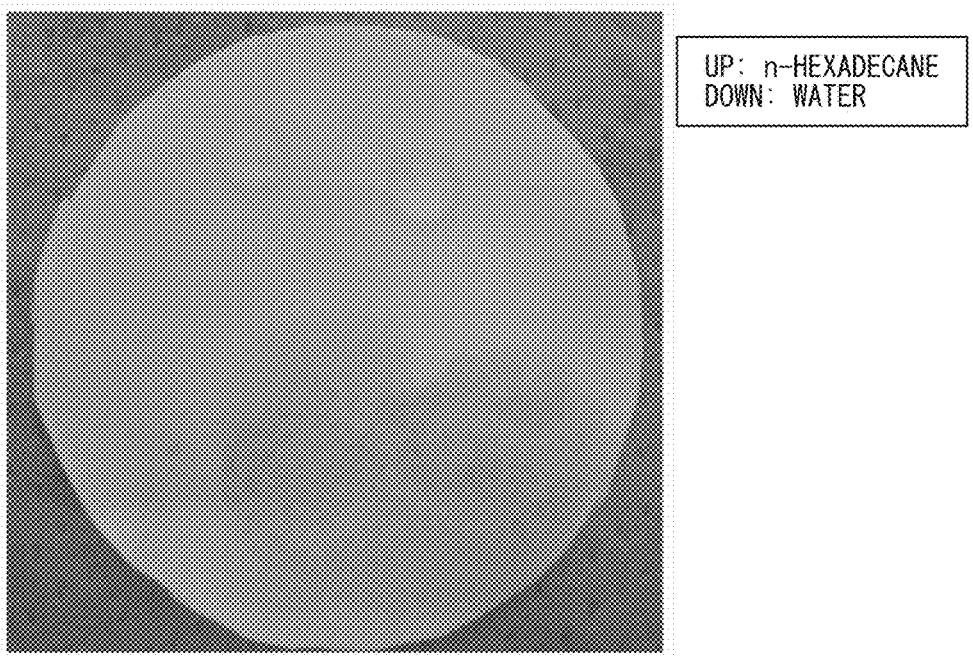
FIG. 1 is a picture showing a representative state of a permeation test result of a nonwoven fabric filter which is an example of the present invention and has a surface treated with an oil-repellent hydrophilic agent.

Hereinafter, a filter medium which is an embodiment to which the present invention is applied will be described in detail along with a method for producing the filter medium, a water treatment module, and a water treatment device.

<Filter Medium>

Firstly, a configuration of the filter medium which is an embodiment to which the present invention is applied will be described.

A filter medium in the embodiment is a filter medium which use a liquid containing water and oil as a separation target and has a channel for the liquid. Specifically, the filter medium in the embodiment includes a base constituting the channel, and one or more of nitrogen-containing fluorine compounds which are provided on at least a portion of a surface of the channel and are represented by the following formulas (1) to (4). The nitrogen-containing fluorine compound may be provided on only one of an entrance side and an exit side of the liquid in the channel, or may be provided in the entirety of the channel.

[Chemical Formula 7]

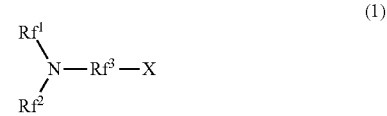

(1)

[Chemical Formula 8]

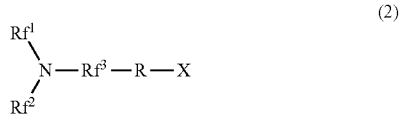

(2)

[Chemical Formula 9]

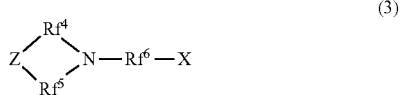

(3)

[Chemical Formula 10]

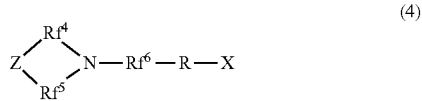

(4)

Here, each of $Rf^1$ and $Rf^2$ in the formulas (1) and (2) is a straight-chain or branched perfluoroalkyl group which is the same as or different from each other and has 1 to 6 carbon atoms. $Rf^3$ is a straight-chain or branched perfluoroalkylene group which has 1 to 6 carbon atoms.

Each of $Rf^1$ and $Rf^2$ is a straight-chain or branched perfluoroalkyl group which is the same as or different from each other and has 1 to 4 carbon atoms. $Rf^2$ is a straight-chain or branched perfluoroalkylene group which has 1 to 4 carbon atoms.

Each of $Rf^4$, $Rf^5$, and $Rf^6$ in the formulas (3) and (4) is a straight-chain or branched perfluoroalkylene group which is the same as or different from each other and has 1 to 6 carbon atoms. Z includes any of an oxygen atom, a nitrogen atom, a $CF_2$ group, and a CF group. In a case where Z is a nitrogen atom or a CF group, a perfluoroalkyl group branched from Z may be bonded to the Z.

Each of $Rf^4$, $Rf^5$, and $Rf^6$ is a straight-chain or branched perfluoroalkylene group which is the same as or different from each other, and has 1 to 4 carbon atoms.

R in the formulas (2) and (4) is a linking group which is a bivalent organic group. Here, R may be a straight-chain or branched organic group. R may or may not include one type or more selected from an ether bond, an ester bond, an amide bond, and an urethane bond in a molecular chain.

X in the formulas (1) to (4) is any one hydrophilicity imparting group selected from a group consisting of an anion type, a cation type, and an amphoteric type in the above formulas.

As described above, nitrogen-containing fluorine compounds represented by the formulas (1) to (4) are oil-repellent hydrophilic agents which include an oil-repellency imparting group and a hydrophilicity imparting group in a molecule. In other words, in the filter medium according to the embodiment, the channel is formed by the base, and the oil-repellent hydrophilic agent is provided on the surface of the channel. A mixture which contains one type or two types or more of nitrogen-containing fluorine compounds, which are selected from a group consisting of the nitrogen-containing fluorine compounds represented by the formulas (1) to (4) may be used as the oil-repellent hydrophilic agent.

The oil-repellent hydrophilic agent will be described below in detail, for each nitrogen-containing fluorine compound.

<Oil-Repellent Hydrophilic Agent>

[Straight-Chain Nitrogen-Containing Fluorine Compound]

In a straight-chain (or branched) nitrogen-containing fluorine compound represented by the formula (1) or the formula (2), a nitrogen-containing perfluoroalkyl group formed from $Rf^1$ and $Rf^2$ and a nitrogen-containing perfluoroalkylene group formed from $Rf^3$ constitute the oil-repellency imparting group.

In the nitrogen-containing fluorine compound represented by the formula (1) or the formula (2), the total number of carbon atoms to which fluorine is bonded in $Rf^1$ to $Rf^3$ which are the oil-repellency imparting groups is preferably in a range of 4 to 18. If the number of carbon atoms to which fluorine is bonded is less than 4, an oil repellent effect is insufficient, and thus this case is not preferable.

A specific example of a structure of the oil-repellency imparting group in the formula (1) or the formula (2) includes structures of the following formulas (7) to (24).

[Chemical Formula 11]

$$CF_3\diagdown N-CF_2-CF_2- \atop CF_3\diagup \qquad (7)$$

[Chemical Formula 12]

$$CF_3\diagdown N-CF_2-\underset{\underset{CF_3}{|}}{CF}- \atop CF_3\diagup \qquad (8)$$

[Chemical Formula 13]

$$CF_3\diagdown N-CF_2CF_2CF_2- \atop CF_3\diagup \qquad (9)$$

[Chemical Formula 14]

$$C_2F_5\diagdown N-CF_2-CF_2- \atop C_2F_5\diagup \qquad (10)$$

[Chemical Formula 15]

$$C_2F_5\diagdown N-CF_2-\underset{\underset{CF_3}{|}}{CF}- \atop C_2F_5\diagup \qquad (11)$$

[Chemical Formula 16]

$$C_2F_5\diagdown N-CF_2CF_2CF_2- \atop C_2F_5\diagup \qquad (12)$$

[Chemical Formula 17]

$$C_3F_7\diagdown N-CF_2-CF_2- \atop C_3F_7\diagup \qquad (13)$$

[Chemical Formula 18]

$$C_3F_7\diagdown N-CF_2-\underset{\underset{CF_3}{|}}{CF}- \atop C_3F_7\diagup \qquad (14)$$

[Chemical Formula 19]

$$C_3F_7\diagdown N-CF_2CF_2CF_2- \atop C_3F_7\diagup \qquad (15)$$

[Chemical Formula 20]

$$C_4F_9\diagdown N-CF_2-CF_2- \atop C_4F_9\diagup \qquad (16)$$

[Chemical Formula 21]

$$C_4F_9\diagdown N-CF_2-\underset{\underset{CF_3}{|}}{CF}- \atop C_4F_9\diagup \qquad (17)$$

[Chemical Formula 22]

$$C_4F_9\diagdown N-CF_2CF_2CF_2- \atop C_4F_9\diagup \qquad (18)$$

[Chemical Formula 23]

$$C_5F_{11}\diagdown N-CF_2-CF_2- \atop C_5F_{11}\diagup \qquad (19)$$

[Chemical Formula 24]

$$C_5F_{11}\diagdown N-CF_2-\underset{\underset{CF_3}{|}}{CF}- \atop C_5F_{11}\diagup \qquad (20)$$

[Chemical Formula 25]

$$\begin{array}{c}C_5F_{11}\\ \phantom{C_5F_{11}}\diagdown\\ \phantom{C_5F_{11}\diagdown}N-CF_2CF_2CF_2-\\ \phantom{C_5F_{11}}\diagup\\ C_5F_{11}\end{array} \quad (21)$$

[Chemical Formula 26]

$$\begin{array}{c}C_6F_{13}\\ \phantom{C_6F_{13}}\diagdown\\ \phantom{C_6F_{13}\diagdown}N-CF_2-CF_2-\\ \phantom{C_6F_{13}}\diagup\\ C_6F_{13}\end{array} \quad (22)$$

[Chemical Formula 27]

$$\begin{array}{c}C_6F_{13} \qquad\qquad CF_3\\ \phantom{C_6F_{13}}\diagdown \qquad\qquad |\\ \phantom{C_6F_{13}\diagdown}N-CF_2-CF-\\ \phantom{C_6F_{13}}\diagup\\ C_6F_{13}\end{array} \quad (23)$$

[Chemical Formula 28]

$$\begin{array}{c}C_6F_{13}\\ \phantom{C_6F_{13}}\diagdown\\ \phantom{C_6F_{13}\diagdown}N-CF_2CF_2CF_2-\\ \phantom{C_6F_{13}}\diagup\\ C_6F_{13}\end{array} \quad (24)$$

[Cyclic Nitrogen-Containing Fluorine Compound]

In a cyclic nitrogen-containing fluorine compound represented by the formula (3) or the formula (4), a nitrogen-containing perfluoroalkylene group formed from $Rf^4$, $Rf^4$, and $Rf^6$, further, Z constitutes the oil-repellency imparting group.

In the cyclic nitrogen-containing fluorine compound represented by the formula (3) or the formula (4), the total number of carbon atoms to which fluorine is bonded in $Rf^4$ to $Rf^6$ and Z which are the oil-repellency imparting group is preferably in a range of 4 to 18, and is more preferably in a range of 5 to 12. If the number of carbon atoms to which fluorine is bonded is less than 4, an oil repellent effect is insufficient, and thus this case is not preferable.

A specific example of a structure of the oil-repellency imparting group in the formula (3) or the formula (4) includes structures of the following formulas (25) to (49).

[Chemical Formula 29]

(25) Morpholine-type ring: $CF_2$–$CF_2$ / $CF_2$ / $CF_2$–$CF_2$ with N–$CF_2$–$CF_2$–

[Chemical Formula 30]

(26) Same ring with N–$CF_2$–$CF(CF_3)$–

[Chemical Formula 31]

(27) Same ring with N–$CF_2$–$CF_2$–$CF_2$–

[Chemical Formula 32]

(28) O-containing ring ($CF_2$–$CF_2$–O–$CF_2$–$CF_2$–N) with N–$CF_2CF_2$–

[Chemical Formula 33]

(29) Same O-ring with N–$CF_2$–$CF(CF_3)$–

[Chemical Formula 34]

(30) Same O-ring with N–$CF_2$–$CF(CF_3)$–

[Chemical Formula 35]

(31) Same O-ring with N–$CF_2CF_2CF_2$–

[Chemical Formula 36]

(32) Four-membered $CF_2$ ring with N–$CF_2$–$CF_2$–

[Chemical Formula 37]

(33) Same ring with N–$CF_2$–$CF(CF_3)$–

[Chemical Formula 38]

(34) Same ring with N–$CF_2$–$CF_2$–$CF_2$–

[Chemical Formula 39]

(35) $CF_3$-substituted O-ring with N–$CF_2$–$CF_2$–

[Chemical Formula 40]

(36) $CF_3$-substituted O-ring with N–$CF_2$–$CF(CF_3)$–

[Chemical Formula 41]

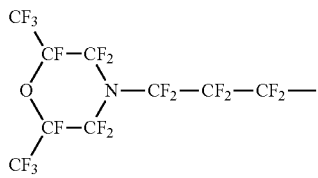
(37)

[Chemical Formula 42]

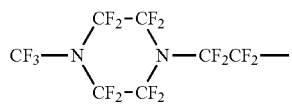
(38)

[Chemical Formula 43]

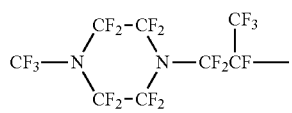
(39)

[Chemical Formula 44]

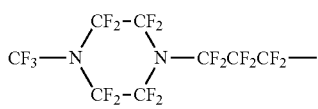
(40)

[Chemical Formula 45]

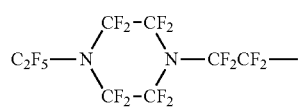
(41)

[Chemical Formula 46]

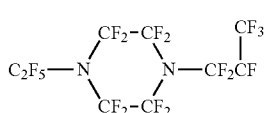
(42)

[Chemical Formula 47]

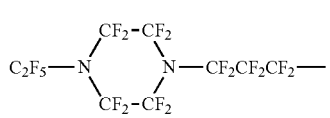
(43)

[Chemical Formula 48]

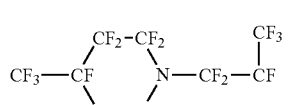
(44)

[Chemical Formula 49]

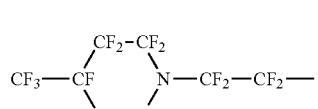
(45)

[Chemical Formula 50]

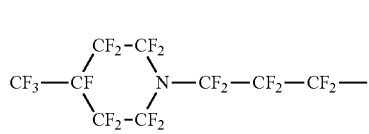
(46)

[Chemical Formula 51]

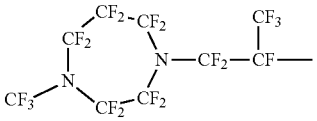
(47)

[Chemical Formula 52]

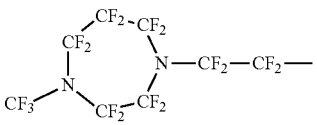
(48)

[Chemical Formula 53]

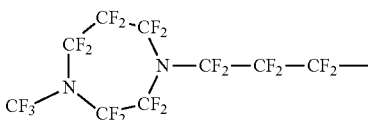
(49)

Here, R in the formulas (2) and (4) is a linking group which links an oil-repellency imparting group and a hydrophilicity imparting group to each other in a molecular chain. The structure of the linking group R is not particularly limited as long as the linking group R is a bivalent organic group. Specific examples of the linking group R may include an oxygen atom [—O—], a carbonyl group [—C(=O)—], an imino group [—NH—], a sulphonyl group [—S(=O)$_2$—], a —OP(=O)(O—)O— group, a hydrocarbon group having 1 to 20 carbon atoms, and combinations thereof. The linking group R may include one type or more selected from a polyoxyalkylene group and an epoxy group. The hydrocarbon group may be a saturated hydrocarbon group or an unsaturated hydrocarbon group. The hydrocarbon group may be a chain hydrocarbon group or a cyclic hydrocarbon group. The chain hydrocarbon group may be a straight-chain or be branched. Examples of the hydrocarbon group may include an alkylene group, an alkenylene group, and an arylene group. The imino group and the hydrocarbon group may have a substituent.

The linking group R may or may not include one or more types of bonds selected from an ether bond, an ester bond, an amide bond, and an urethane bond in the molecular chain. The amide bond includes a carboxylic acid amide bond and a sulfonamide bond. The ester bond includes a carboxylic acid ester bond, a sulfonic acid ester bond, and a phosphate ester bond.

It is preferable that the linking group R is appropriately selected and applied in accordance with characteristics which are desired to be applied to the nitrogen-containing fluorine compound. Specific examples include a case where adjusting solubility to water, an organic solvent, or the like is desired, a case where adhesion to base is improved so as to wish improvement of durability, and a case where compatibility with a resin component or the like wishes to be improved. As the method, there is provided, for example, methods as follows: a method in which presence or absence and the type of a polar group which influences interaction between molecules is adjusted; a method in which the length of a chain in a hydrocarbon group having a straight-chain or branched structure is adjusted; and a method in which a structure similar to a portion of a chemical structure provided in the base or a resin component is applied.

X in the formulas (1) to (4) is any one hydrophilicity imparting group selected from a group consisting of an anion type, a cation type, and an amphoteric type in the above formulas.

The structure of the oil-repellent hydrophilic agent in the embodiment will be described below by using a case of a hydrophilicity imparting group X.

[Anion Type]

In a case where the hydrophilicity imparting group X is an anion type, the X has "—$CO_2M^1$", "—$SO_3M^1$", "—$OSO_3M^1$", "—$OP(OH)O_2M^1$", "—$OPO_3M^1{}_2$", "=$O_2PO_2M^1$", or "—$PO(OH)_y(OM^1)_{2-y}$," ($M^1$ indicates alkali metal, alkaline-earth metal, Mg, and Al, and $R^1R^2R^3R^4N^+$; $R^1$ to $R^4$ indicate straight chain or branched alkyl groups which are independent from each other, and have hydrogen atoms or 1 to 20 carbon atoms (preferably, 1 to 10 carbon atoms); and y indicates an integer of 0 to 2). In a case where $M^1$ is bivalent metal (alkaline-earth metal, Mg), two identical anions may be bonded to $M^1$, or two different types of anions may be bonded to $M^1$. In a case where $M^1$ is aluminium, three same anions may be bonded to $M^1$, or two or three different types of anions may be bonded to $M^1$.

As the alkali metal, lithium (Li), sodium (Na), potassium (K), and cesium (Cs) are exemplified. As the alkaline-earth metal, calcium (Ca), strontium (Sr), and barium (Ba) are exemplified.

A quaternary ammonium salt ($R^1R^2R^3R^4N^-$) is not particularly limited as long as $R^1$ to $R^4$ indicate straight chain or branched alkyl groups which are independent from each other, and have hydrogen atoms or 1 to 20 carbon atoms (preferably, 1 to 10 carbon atoms. Here, if the number of carbon atoms of the alkyl group is equal to or less than 20, the hydrophilic and oil-repellent properties are not damaged. Thus, this case is preferable. More specifically, as a case where all of $R^1$, $R^2$, $R^3$, and $R^4$ are the same compounds, for example, $(CH_3)_4N^+$, $(C_2H_5)_4N^+$, $(C_3H_7)_4N^+$, $(C_4H_9)_4N^+$, $(C_5H_{11})_4N^+$, $(C_6H_{13})_4N^+$, $(C_7H_{15})_4N^+$, $(C_8H_{17})_4N^+$, $(C_9H_{19})_4N^-$, and $(C_{10}H_{21})_4N^+$ are exemplified. As a case where all of $R^1$, $R^2$, and $R^3$ are methyl groups, for example, compounds in which $R^4$ is $(C_2H_5)$, $(C_6H_{13})$, $(C_8H_{17})$, $(C_9H_{19})$, $(C_{10}H_{21})$, $(C_{12}H_{25})$, $(C_{14}H_{29})$, $(C_{16}H_{33})$, $(C_{18}H_{37})$, or the like are exemplified. Further, as a case where all of $R^1$ and $R^2$ are methyl groups, for example, compounds in which all of $R^3$ and $R^4$ are $(C_8H_{17})$, $(C_{10}H_{21})$, $(C_{12}H_{25})$, $(C_{14}H_{29})$, $(C_{16}H_{33})$, $(C_{18}H_{37})$, or the like are exemplified. As a case where $R^1$ is a methyl group, for example, compounds in which all of $R^2$, $R^3$, and $R^4$ are $(C_4H_9)$, $(C_8H_{17})$, or the like are exemplified.

Regarding a material, for example, which is used by being brought into contact with water, such as an oil-water separating member, it is desirable that the material has durability against water, or persistence of a hydrophilic and oil-repellent effect for water. From this viewpoint, in the oil-repellent hydrophilic agent in this embodiment, the nitrogen-containing fluorine compound is desirably a poorly water-soluble compound having low solubility to water. That is, regarding the oil-repellent hydrophilic agent in this embodiment, in a case where the hydrophilicity imparting group X is an anion type, M1 which is a counterpart ion is preferably alkaline-earth metal, Mg, or Al. Because Ca, Ba, and Mg have exceptional hydrophilic and oil-repellent properties and low solubility to water, Ca, Ba, and Mg are particularly preferable.

Here, in a case where the hydrophilicity imparting group X is an anion type, a specific example (except for the structure of M1 which is the counterpart ion) of a structure of the oil-repellent hydrophilic agent (that is, straight-chain nitrogen-containing fluorine compound) represented by the formula (1) or the formula (2) includes structures of the following formulas (50) to (117).

[Chemical Formula 54]

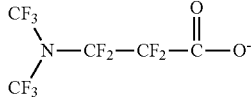
(50)

[Chemical Formula 55]

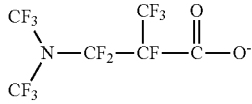
(51)

[Chemical Formula 56]

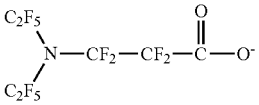
(52)

[Chemical Formula 57]

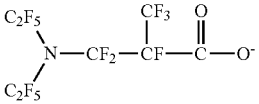
(53)

[Chemical Formula 58]

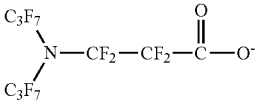
(54)

[Chemical Formula 59]

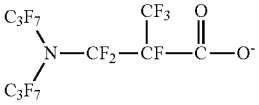
(55)

[Chemical Formula 60]

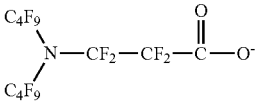
(56)

[Chemical Formula 61]

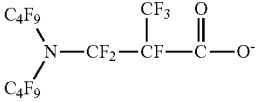
(57)

[Chemical Formula 62]

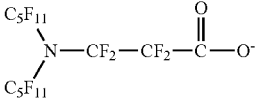
(58)

[Chemical Formula 63]

(59) $(C_5F_{11})_2N-CF_2-CF(CF_3)-C(=O)-O^-$

[Chemical Formula 64]

(60) $(C_6F_{13})_2N-CF_2-CF_2-C(=O)-O^-$

[Chemical Formula 65]

(61) $(C_6F_{13})_2N-CF_2-CF(CF_3)-C(=O)-O^-$

[Chemical Formula 66]

(62) $(CF_3)_2N-CF_2-CF_2-C(=O)-N(H)-CH_2-C(=O)-O^-$

[Chemical Formula 67]

(63) $(C_3F_7)_2N-CF_2-CF_2-C(=O)-N(H)-CH_2CH_2-C(=O)-O^-$

[Chemical Formula 68]

(64) $(C_4F_9)_2N-CF_2-CF_2-C(=O)-N(H)-CH(CH_3)-CH_2-C(=O)-O^-$

[Chemical Formula 69]

(65) $(C_4F_9)_2N-CF_2-CF_2-C(=O)-N(CH_3)-CH_2CH_2-C(=O)-O^-$

[Chemical Formula 70]

(66) $(C_6F_{13})_2N-CF_2-CF(CF_3)-C(=O)-N(H)-(CH_2)_5-C(=O)-O^-$

[Chemical Formula 71]

(67) $(CF_3)_2N-CF_2-CF_2-C(=O)-N(H)-CH_2-S(=O)_2-O^-$

[Chemical Formula 72]

(68) $(C_3F_7)_2N-CF_2-CF_2-C(=O)-N(CH_3)-CH_2CH_2-S(=O)_2-O^-$

[Chemical Formula 73]

(69) $(C_4F_9)_2N-CF_2-CF_2-C(=O)-N(CH_3)-CH_2CH_2-S(=O)_2-O^-$

[Chemical Formula 74]

(70) $(C_6F_{13})_2N-CF_2-CF(CF_3)-C(=O)-N(CH_3)-CH_2CH_2-S(=O)_2-O^-$

[Chemical Formula 75]

(71) $(C_3F_7)_2N-CF_2-CF-C(=O)-N(H)-N(C(=O)O^-)-CH_2CH_2-C(=O)-O^-$

[Chemical Formula 76]

(72) $(C_4F_9)_2N-CF_2-CF_2-C(=O)-N(H)-N(C(=O)O^-)-CH_2CH_2-C(=O)-O^-$

[Chemical Formula 77]

(73) $(C_6F_{13})_2N-CF_2-CF(CF_3)-C(=O)-N(H)-N(C(=O)O^-)-CH_2CH_2-C(=O)-O^-$

[Chemical Formula 78]

(74) $(C_4F_9)_2N-CF_2-CF_2-C(=O)-N(H)-C_6H_4-CH_2-C(=O)-O^-$

[Chemical Formula 79]

(75) $(C_4F_9)_2N-CF_2-CF_2-C(=O)-N(H)-C_6H_4-CH=CH-C(=O)-O^-$

[Chemical Formula 80]

(76) $(CF_3)_2N-CF_2-CF_2-C(=O)-N(H)-C_6H_4-S(=O)_2-O^-$

[Chemical Formula 81]

(77) $(C_3F_7)_2N-CF_2-CF-C(=O)-N(H)-C_6H_4-S(=O)_2-O^-$

-continued

[Chemical Formula 82]

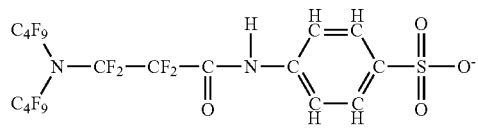
(78)

[Chemical Formula 83]

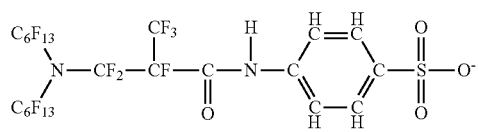
(79)

[Chemical Formula 84]

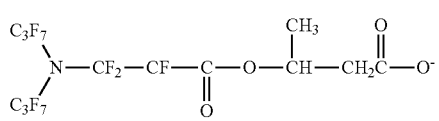
(80)

[Chemical Formula 85]

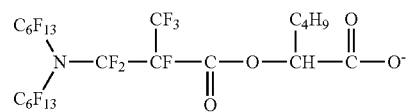
(81)

[Chemical Formula 86]

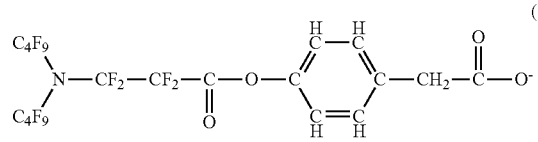
(82)

[Chemical Formula 87]

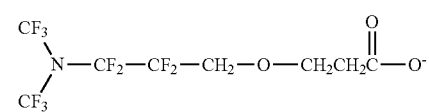
(83)

[Chemical Formula 88]

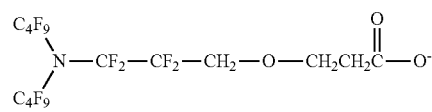
(84)

[Chemical Formula 89]

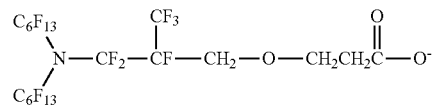
(85)

[Chemical Formula 90]

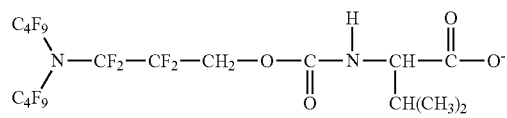
(86)

[Chemical Formula 91]

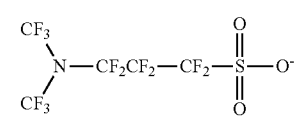
(87)

-continued

[Chemical Formula 92]

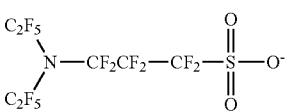
(88)

[Chemical Formula 93]

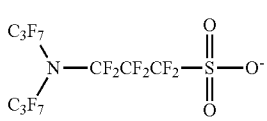
(89)

[Chemical Formula 94]

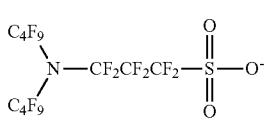
(90)

[Chemical Formula 95]

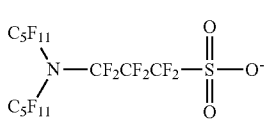
(91)

[Chemical Formula 96]

(92)

[Chemical Formula 97]

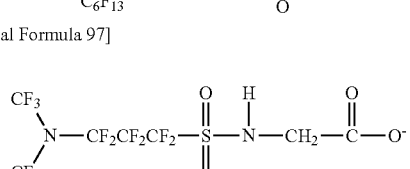
(93)

[Chemical Formula 98]

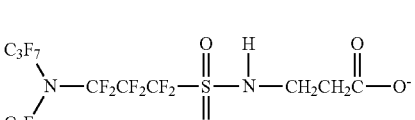
(94)

[Chemical Formula 99]

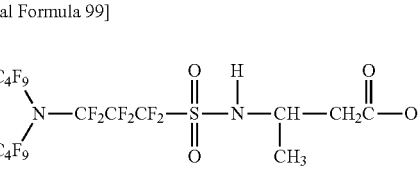
(95)

[Chemical Formula 100]

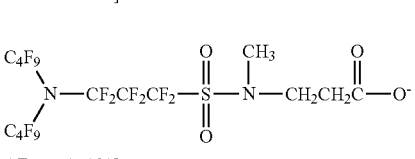
(96)

[Chemical Formula 101]

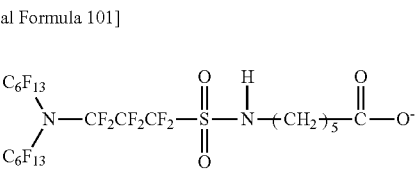
(97)

-continued
[Chemical Formula 102]
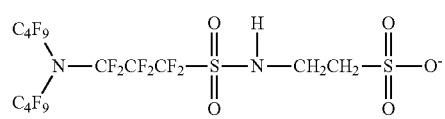
(98)
[Chemical Formula 103]
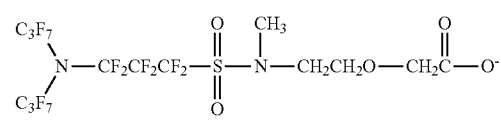
(99)
[Chemical Formula 104]
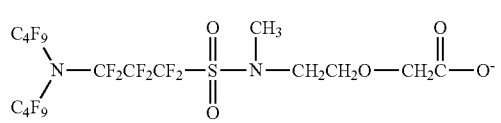
(100)
[Chemical Formula 105]
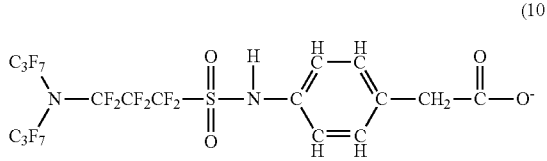
(101)
[Chemical Formula 106]
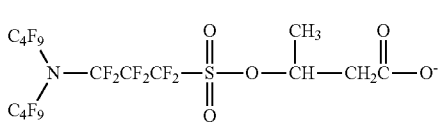
(102)
[Chemical Formula 107]
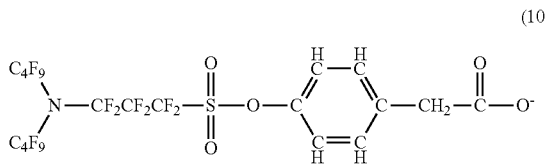
(103)
[Chemical Formula 108]
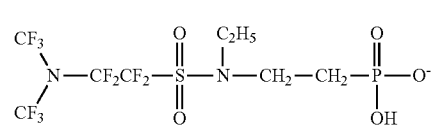
(104)
[Chemical Formula 109]
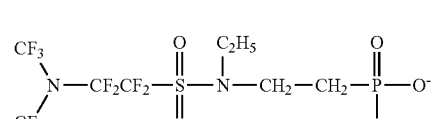
(105)
[Chemical Formula 110]
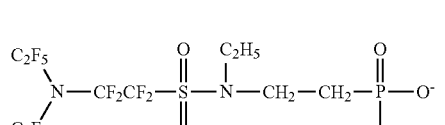
(106)
[Chemical Formula 111]
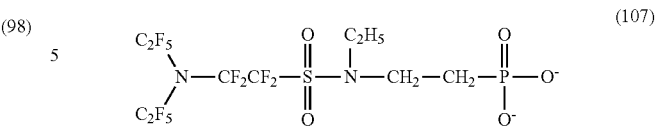
(107)
[Chemical Formula 112]
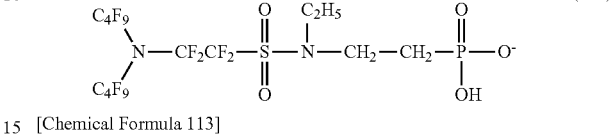
(108)
[Chemical Formula 113]
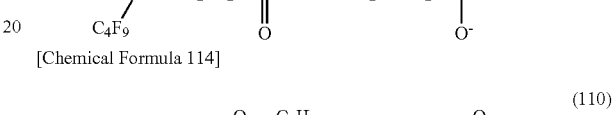
(109)
[Chemical Formula 114]
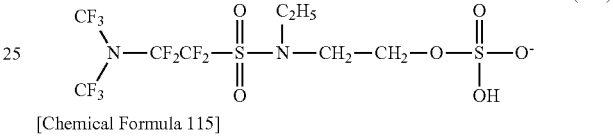
(110)
[Chemical Formula 115]
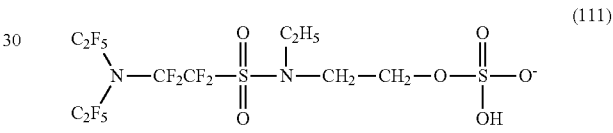
(111)
[Chemical Formula 116]
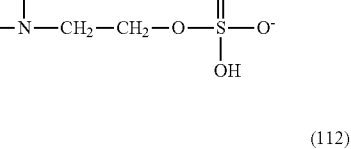
(112)
[Chemical Formula 117]
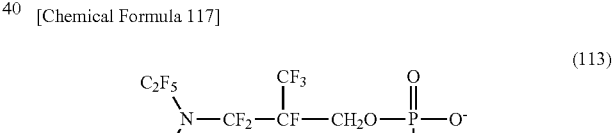
(113)
[Chemical Formula 118]
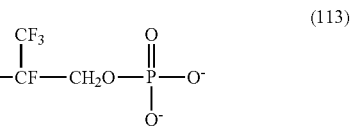
(114)
[Chemical Formula 119]
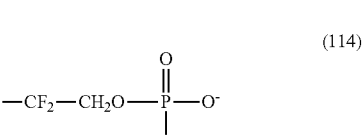
(115)
[Chemical Formula 120]
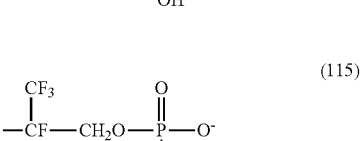
(116)

[Chemical Formula 121]

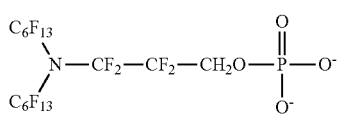 (117)

On the contrary, a specific example (except for the structure of $M^1$ which is the counterpart ion) of a structure of the oil-repellent hydrophilic agent (that is, cyclic nitrogen-containing fluorine compound) represented by the formula (3) or the formula (4) includes structures of the following formulas (118) to (189).

[Chemical Formula 122]

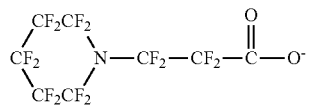 (118)

[Chemical Formula 123]

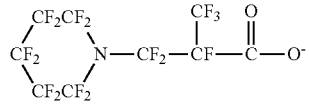 (119)

[Chemical Formula 124]

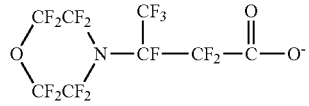 (120)

[Chemical Formula 125]

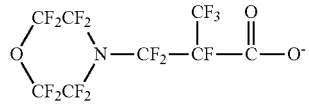 (121)

[Chemical Formula 126]

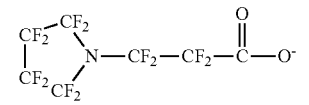 (122)

[Chemical Formula 127]

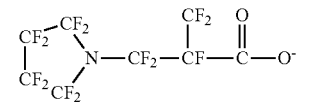 (123)

[Chemical Formula 128]

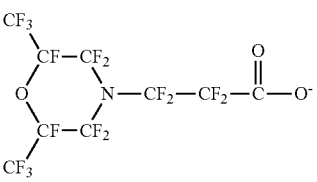 (124)

[Chemical Formula 129]

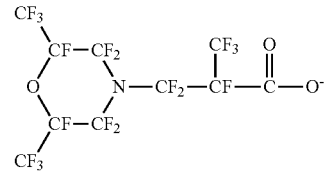 (125)

[Chemical Formula 130]

(126)

[Chemical Formula 131]

(127)

[Chemical Formula 132]

(128)

[Chemical Formula 133]

(129)

[Chemical Formula 134]

(130)

[Chemical Formula 135]

(131)

[Chemical Formula 136]

(132)

[Chemical Formula 137]

(133)

[Chemical Formula 138]
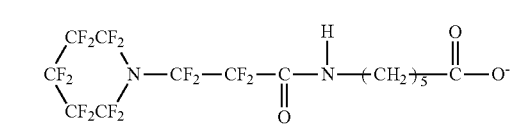
(134)
[Chemical Formula 139]
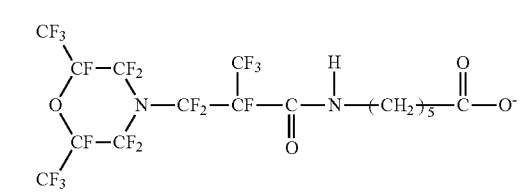
(135)
[Chemical Formula 140]
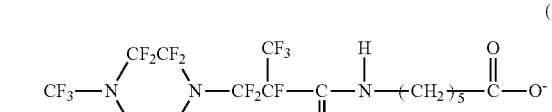
(136)
[Chemical Formula 141]
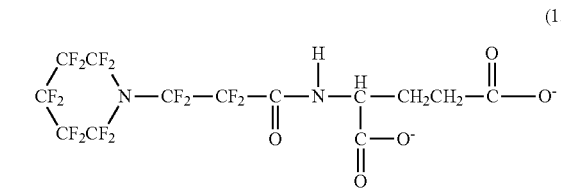
(137)
[Chemical Formula 142]
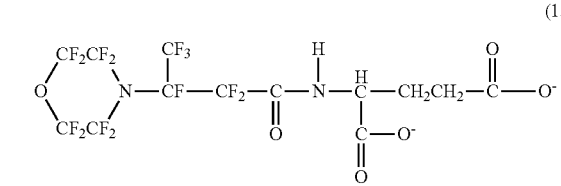
(138)
[Chemical Formula 143]
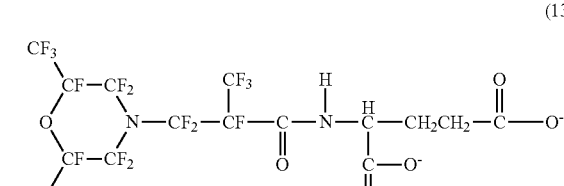
(139)
[Chemical Formula 144]
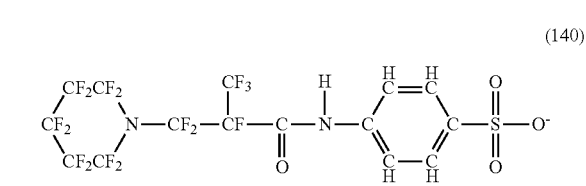
(140)
[Chemical Formula 145]
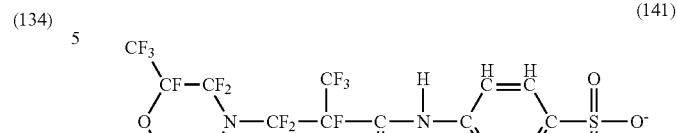
(141)
[Chemical Formula 146]
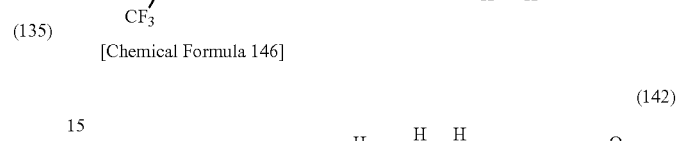
(142)
[Chemical Formula 147]
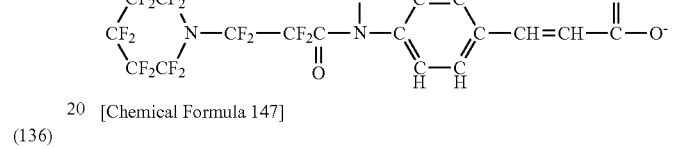
(143)
[Chemical Formula 148]
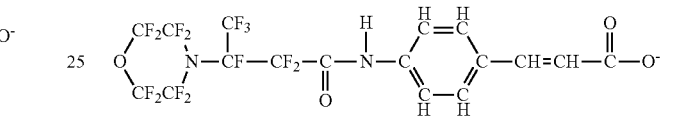
(144)
[Chemical Formula 149]
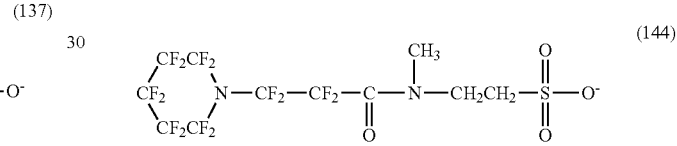
(145)
[Chemical Formula 150]
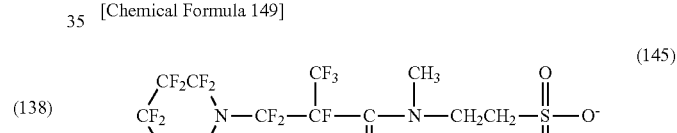
(146)
[Chemical Formula 151]
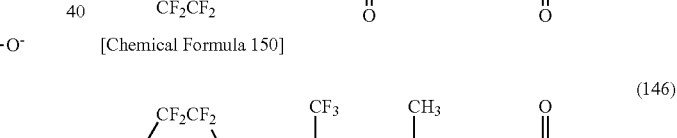
(147)
[Chemical Formula 152]
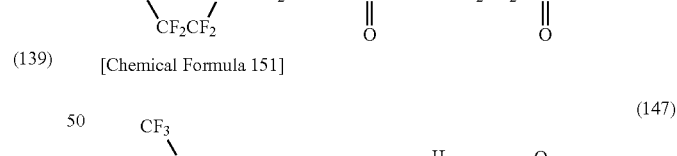
(148)

[Chemical Formula 153]
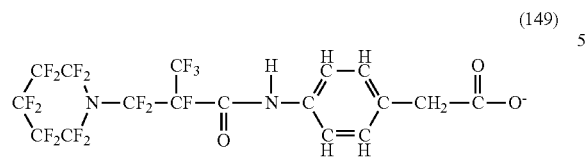
(149)
[Chemical Formula 154]
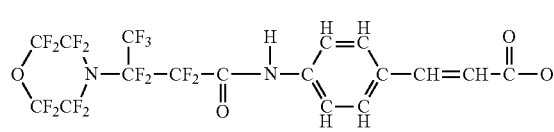
(150)
[Chemical Formula 155]
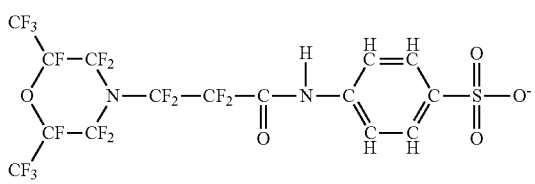
(151)
[Chemical Formula 156]
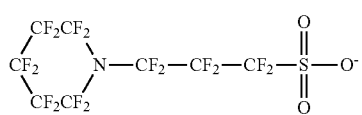
(152)
[Chemical Formula 157]
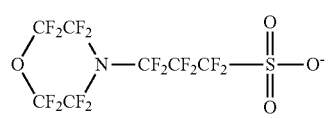
(153)
[Chemical Formula 158]
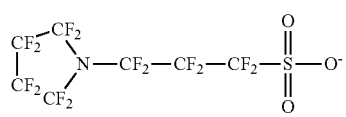
(154)
[Chemical Formula 159]
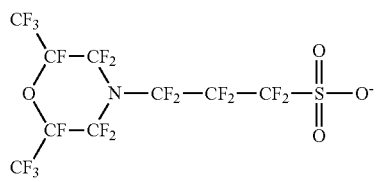
(155)
[Chemical Formula 160]
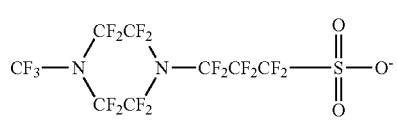
(156)
[Chemical Formula 161]
(157)
[Chemical Formula 162]
(158)
[Chemical Formula 163]
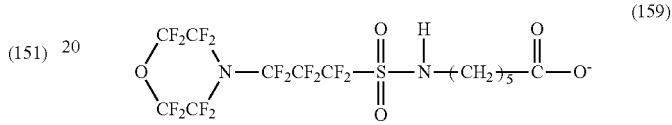
(159)
[Chemical Formula 164]
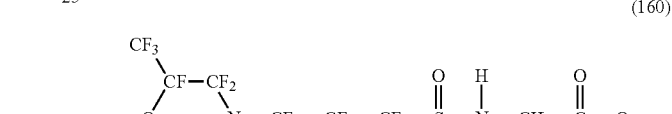
(160)
[Chemical Formula 165]
(161)
[Chemical Formula 166]
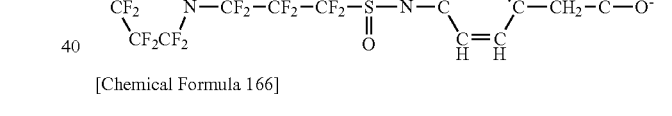
(162)
[Chemical Formula 167]
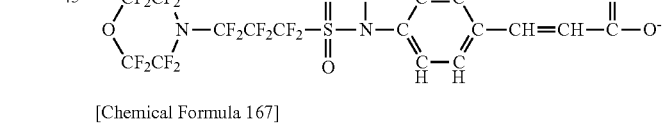
(163)
[Chemical Formula 168]
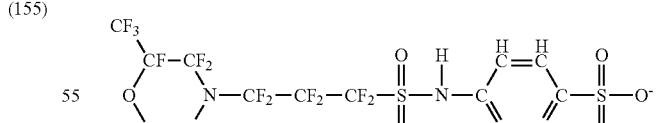
(164)

[Chemical Formula 169]
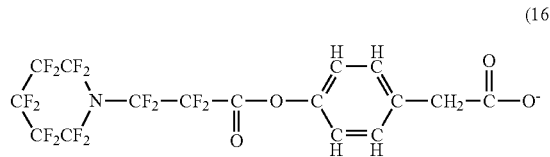
(165)
[Chemical Formula 170]
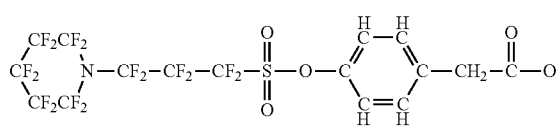
(166)
[Chemical Formula 171]
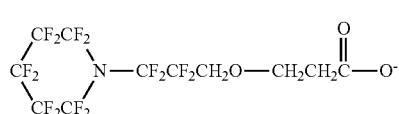
(167)
[Chemical Formula 172]
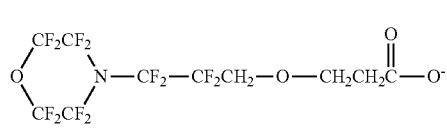
(168)
[Chemical Formula 173]
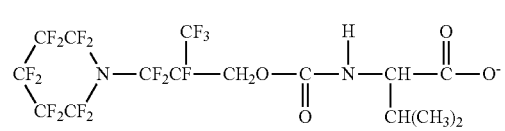
(169)
[Chemical Formula 174]
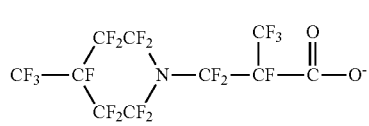
(170)
[Chemical Formula 175]
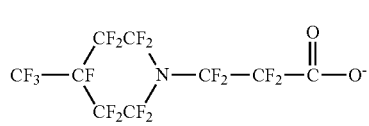
(171)
[Chemical Formula 176]
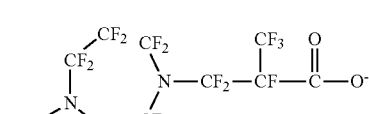
(172)
[Chemical Formula 177]
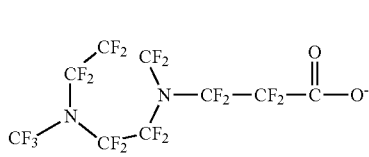
(173)
[Chemical Formula 178]
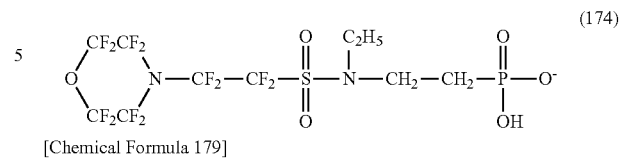
(174)
[Chemical Formula 179]
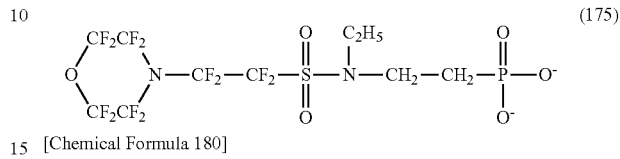
(175)
[Chemical Formula 180]
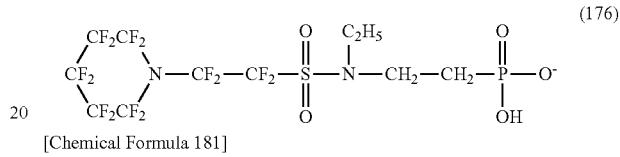
(176)
[Chemical Formula 181]
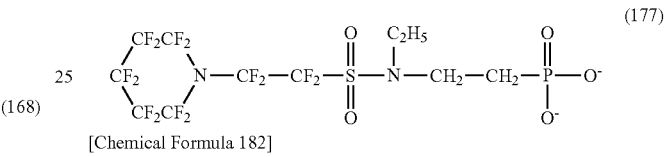
(177)
[Chemical Formula 182]
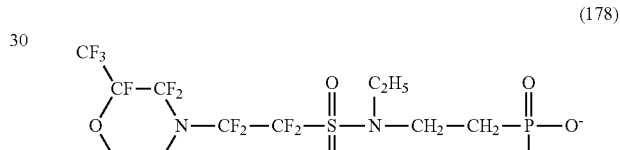
(178)
[Chemical Formula 183]
(179)
[Chemical Formula 184]
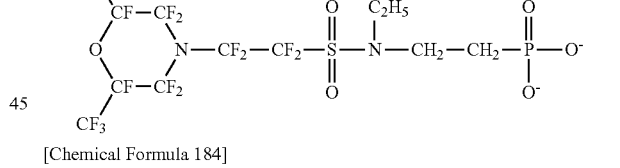
(180)
[Chemical Formula 185]
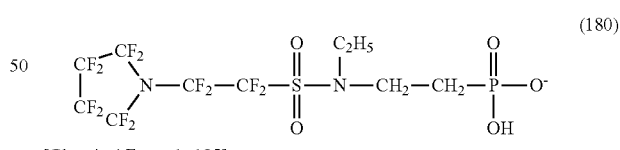
(181)
[Chemical Formula 186]
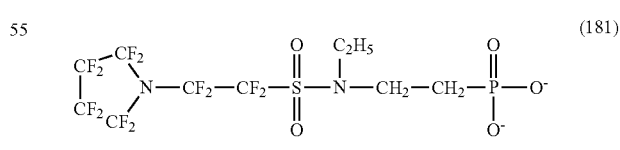
(182)
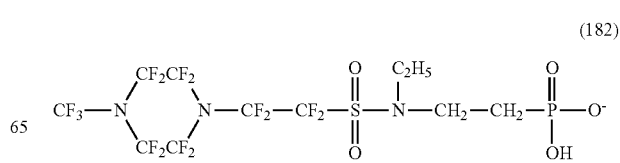

-continued

[Chemical Formula 187]

(183)

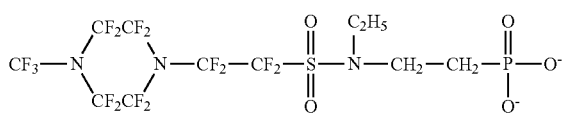

[Chemical Formula 188]

(184)

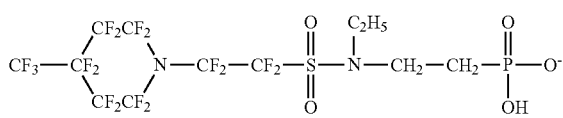

[Chemical Formula 189]

(185)

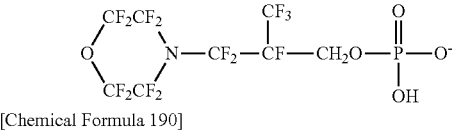

[Chemical Formula 190]

(186)

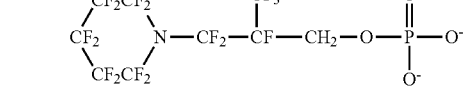

[Chemical Formula 191]

(187)

[Chemical Formula 192]

(188)

[Chemical Formula 193]

(189)

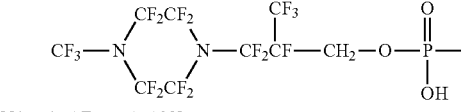

[Cation Type]

In a case where the hydrophilicity imparting group X is a cation type, the X has "—N⁺R⁵R⁶R⁷.Cl—", "—N⁺R⁵R⁶R⁷.Br—", "—N⁺R⁵R⁶R⁷.I—", "—N⁺R⁵R⁶R⁷.CH₂SO₃⁻", "—N⁺R⁵R⁶R⁷.R⁷SO₄⁻", "—N⁺R⁵R⁶R⁷.NO₃⁻", "(—N⁺R⁵R⁶R⁷)₂CO₃²⁻", "(—N⁺R⁵R⁶R⁷)₂SO₄²⁻" at the termination (R⁵ to R⁷ are straight chain or branched alkyl groups which are independent from each other, and have hydrogen atoms or 1 to 20 carbon atoms (preferably, 1 to 10 carbon atoms)). Here, if the number of carbon atoms of the alkyl group is equal to or less than 20, the hydrophilic and oil-repellent properties are not damaged. Thus, this case is preferable.

Here, in a case where the hydrophilicity imparting group X is a cation type, a specific example of a structure of the oil-repellent hydrophilic agent (that is, straight-chain nitrogen-containing fluorine compound) represented by the formula (1) or the formula (2) includes structures of the following formulas (190) to (223).

[Chemical Formula 194]

(190)

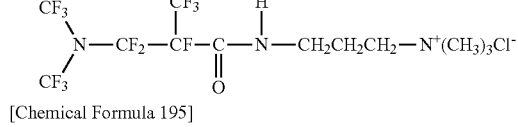

[Chemical Formula 195]

(191)

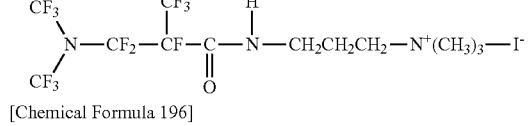

[Chemical Formula 196]

(192)

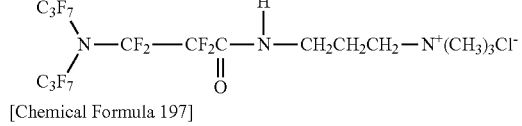

[Chemical Formula 197]

(193)

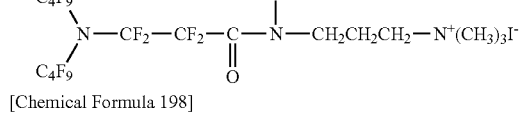

[Chemical Formula 198]

(194)

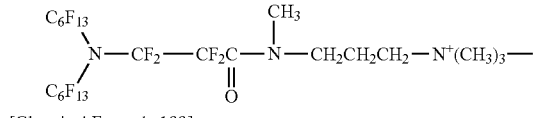

[Chemical Formula 199]

(195)

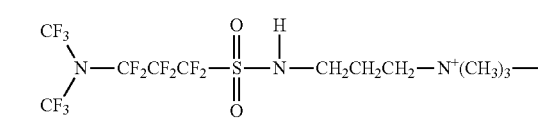

[Chemical Formula 200]

(196)

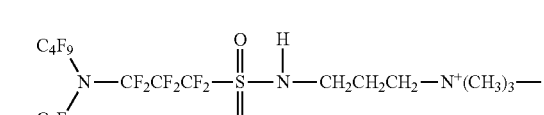

[Chemical Formula 201]

(197)

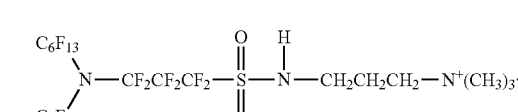

[Chemical Formula 202]

(198)

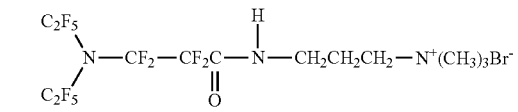

[Chemical Formula 203]
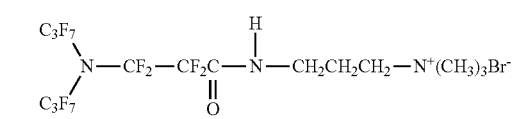
(199)
[Chemical Formula 204]
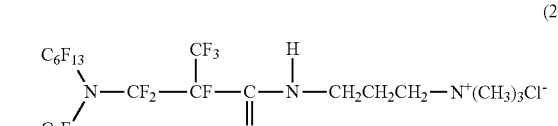
(200)
[Chemical Formula 205]
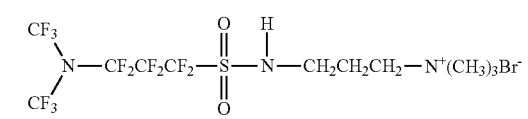
(201)
[Chemical Formula 206]
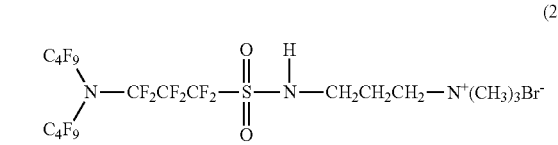
(202)
[Chemical Formula 207]
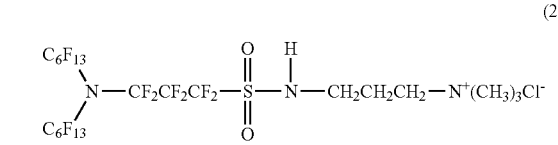
(203)
[Chemical Formula 208]
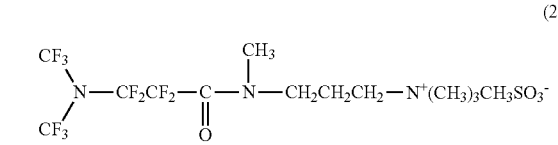
(204)
[Chemical Formula 209]
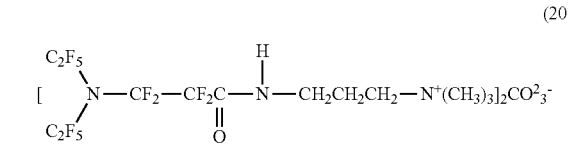
(205)
[Chemical Formula 210]
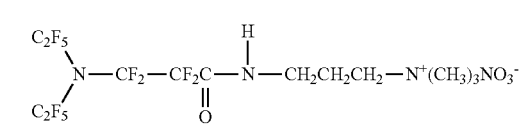
(206)
[Chemical Formula 211]
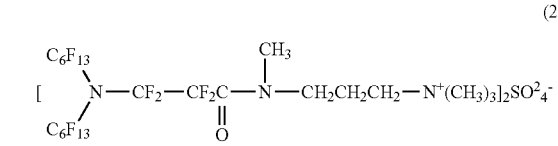
(207)
[Chemical Formula 212]
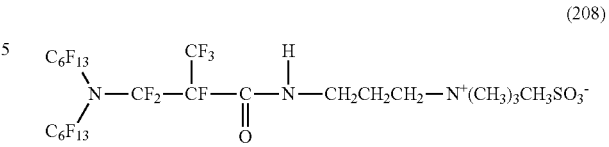
(208)
[Chemical Formula 213]
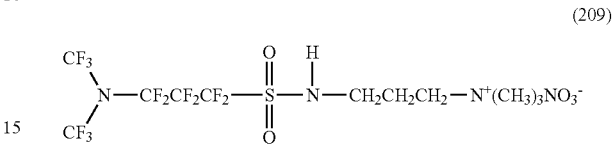
(209)
[Chemical Formula 214]
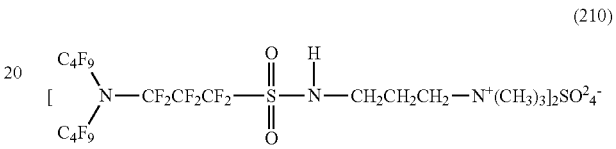
(210)
[Chemical Formula 215]
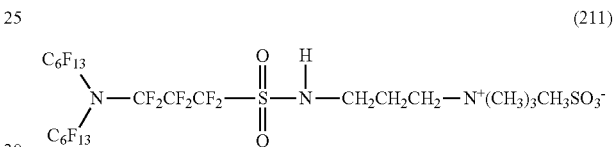
(211)
[Chemical Formula 216]
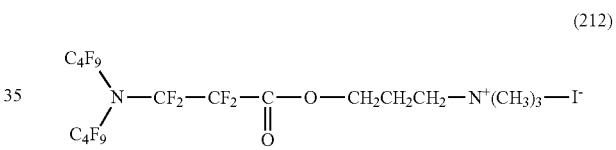
(212)
[Chemical Formula 217]
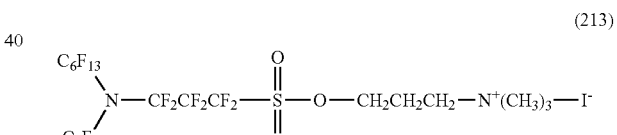
(213)
[Chemical Formula 218]
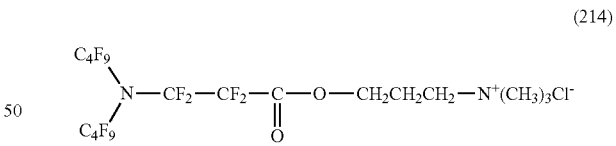
(214)
[Chemical Formula 219]
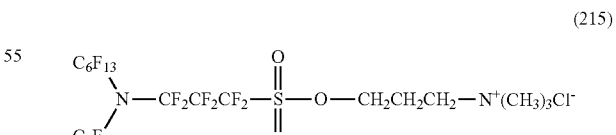
(215)
[Chemical Formula 220]
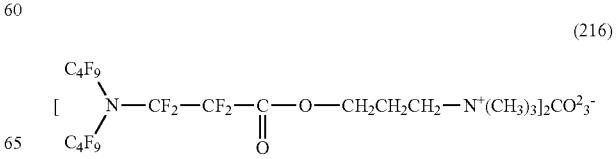
(216)

[Chemical Formula 221]

(217)
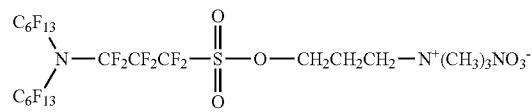

[Chemical Formula 222]

(218)
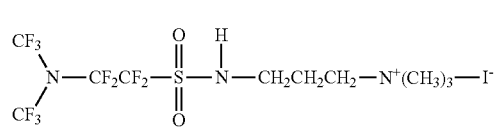

[Chemical Formula 223]

(219)
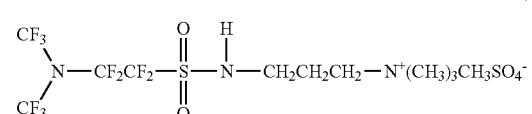

[Chemical Formula 224]

(220)
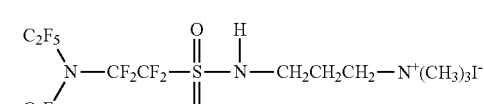

[Chemical Formula 225]

(221)
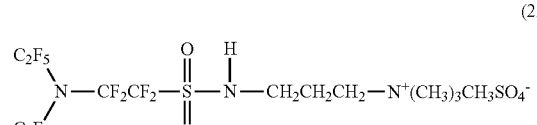

[Chemical Formula 226]

(222)
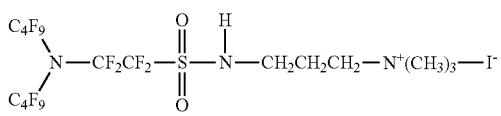

[Chemical Formula 227]

(223)
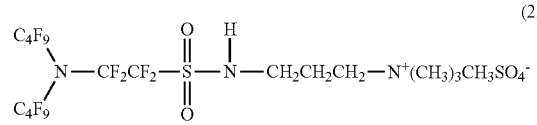

On the contrary, a specific example of a structure of the oil-repellent hydrophilic agent (that is, cyclic nitrogen-containing fluorine compound) represented by the formula (3) or the formula (4) includes structures of the following formulas (224) to (258).

[Chemical Formula 228]

(224)
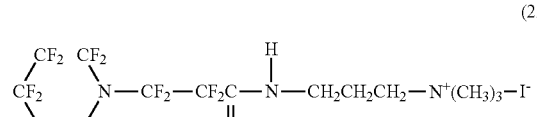

[Chemical Formula 229]

(225)
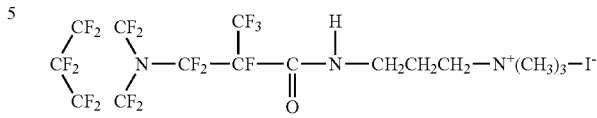

[Chemical Formula 230]

(226)
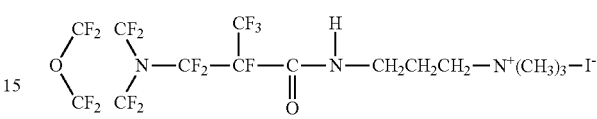

[Chemical Formula 231]

(227)
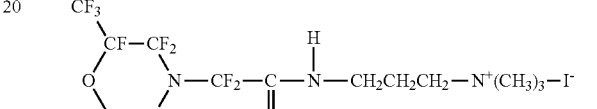

[Chemical Formula 232]

(228)
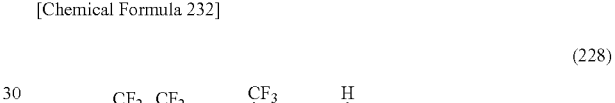

[Chemical Formula 233]

(229)

[Chemical Formula 234]

(230)
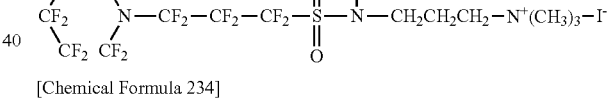

[Chemical Formula 235]

(231)
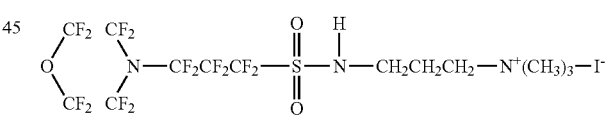

[Chemical Formula 236]

(232)
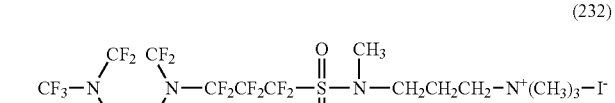

[Chemical Formula 237]
(233)
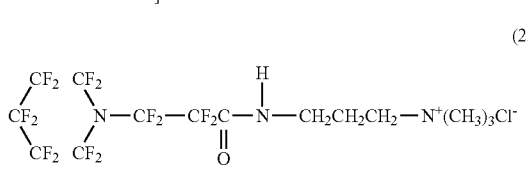
[Chemical Formula 238]
(234)
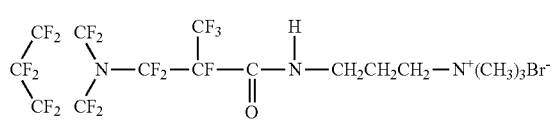
[Chemical Formula 239]
(235)
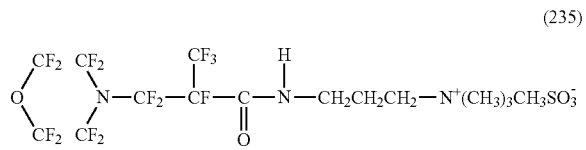
[Chemical Formula 240]
(236)
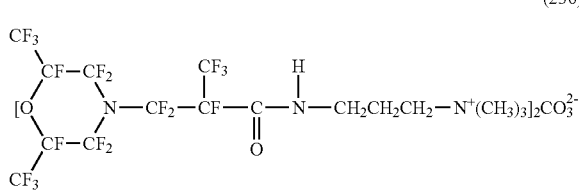
[Chemical Formula 241]
(237)
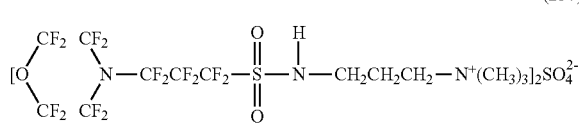
[Chemical Formula 242]
(238)
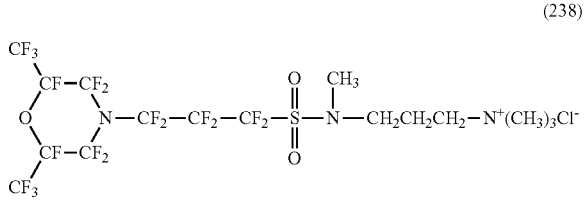
[Chemical Formula 243]
(239)
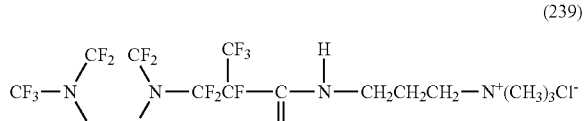
[Chemical Formula 244]
(240)
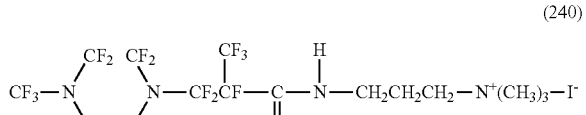
[Chemical Formula 245]
(241)
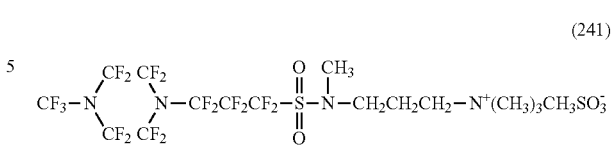
[Chemical Formula 246]
(242)
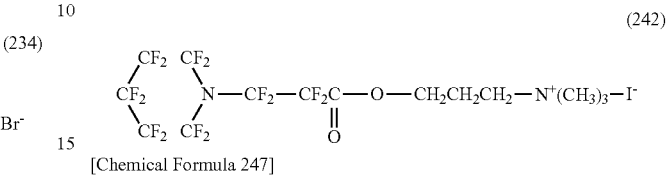
[Chemical Formula 247]
(243)
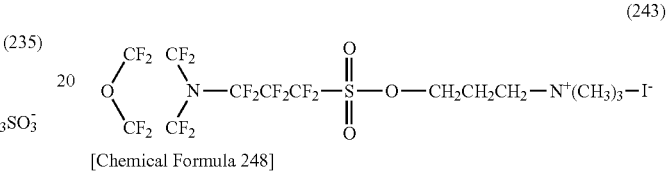
[Chemical Formula 248]
(244)
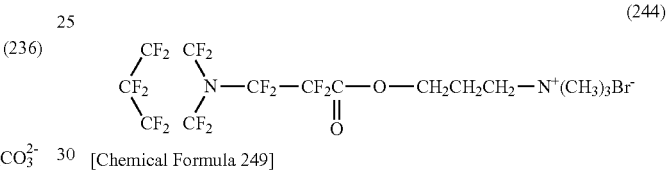
[Chemical Formula 249]
(245)
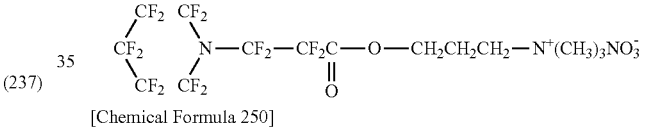
[Chemical Formula 250]
(246)
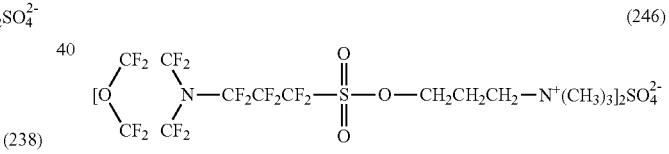
[Chemical Formula 251]
(247)
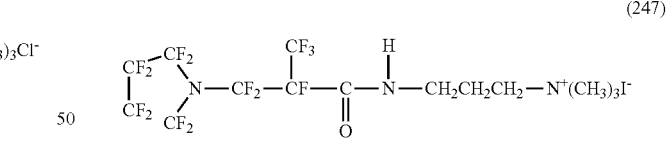
[Chemical Formula 252]
(248)
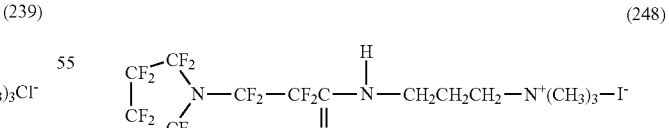
[Chemical Formula 253]
(249)
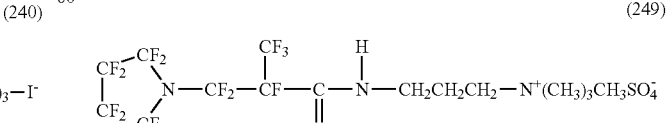

-continued

[Chemical Formula 254]

(250)
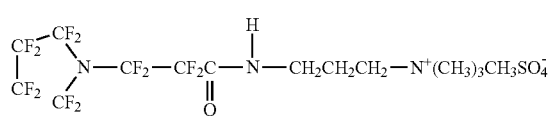

[Chemical Formula 255]

(251)
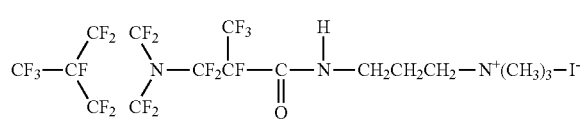

[Chemical Formula 256]

(252)
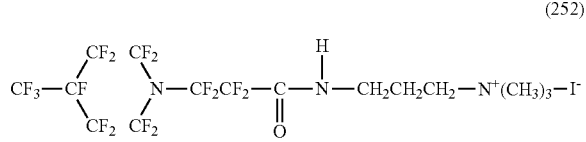

[Chemical Formula 257]

(253)
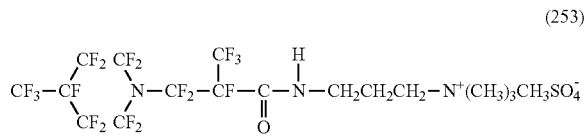

[Chemical Formula 258]

(254)
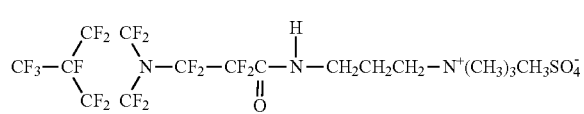

[Chemical Formula 259]

(255)
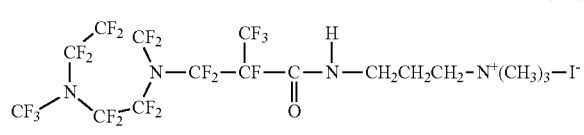

[Chemical Formula 260]

(256)
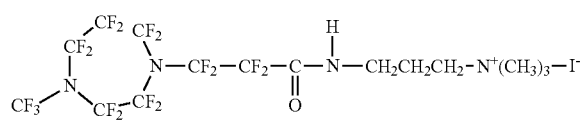

[Chemical Formula 261]

(257)
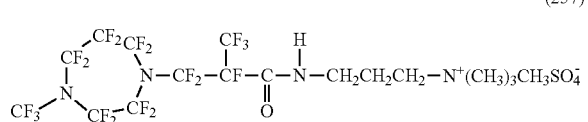

[Chemical Formula 262]

(258)
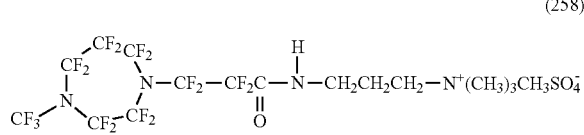

[Amphoteric Type]

In a case where the hydrophilicity imparting group X is an amphoteric type, the X has a carboxy betaine type of "—$N^+R^8R^9(CH_2)_nCO_2$—", a sulfobetaine type of "—$N^+R^8R^9(CH_2)_nSO_3^-$—", an amine oxide type of "—$N^+R^8R^9O$—", or a phosphobetaine type of "—$OPO_3^-(CH_2)_nN^+R^8R^9R^{10}$" at the termination (n is an integer of 1 to 5, $R^8$ and $R^9$ indicates an alkyl group having a hydrogen atom or 1 to 10 carbon atoms, and $R^{10}$ indicates an alkyl group having a hydrogen atom or 1 to 10 carbon atoms or an alkylene group having 1 to 10 carbon atoms). Here, if the number of carbon atoms of the alkyl group is equal to or less than 10, the hydrophilic and oil-repellent properties are not damaged. Thus, this case is preferable.

Here, in a case where the hydrophilicity imparting group X is an amphoteric type, a specific example of a structure of the oil-repellent hydrophilic agent (that is, straight-chain nitrogen-containing fluorine compound) represented by the formula (1) or the formula (2) includes structures of the following formulas (259) to (309).

[Chemical Formula 263]

(259)
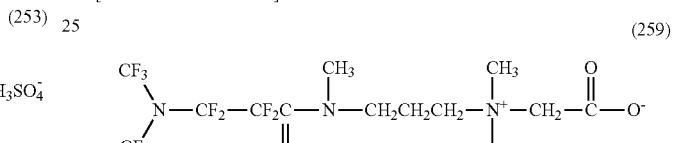

[Chemical Formula 264]

(260)
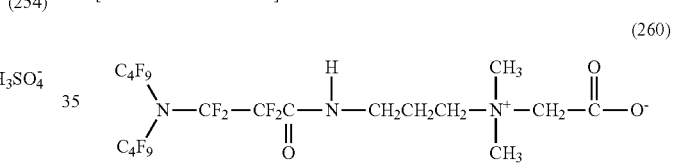

[Chemical Formula 265]

(261)
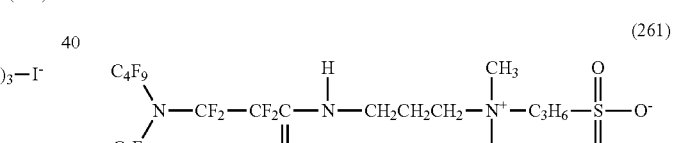

[Chemical Formula 266]

(262)
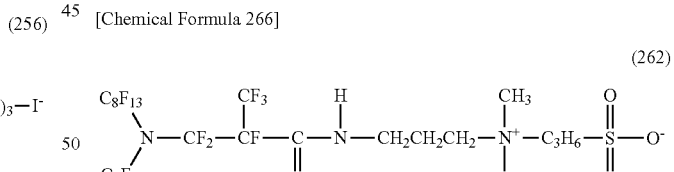

[Chemical Formula 267]

(263)
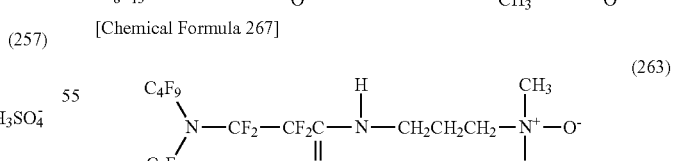

[Chemical Formula 268]

(264)
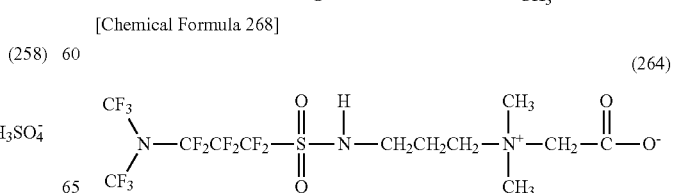

[Chemical Formula 269]
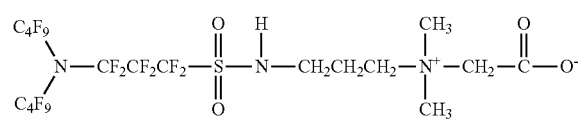
(265)
[Chemical Formula 270]
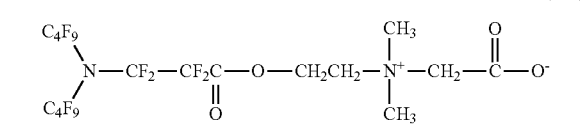
(266)
[Chemical Formula 271]
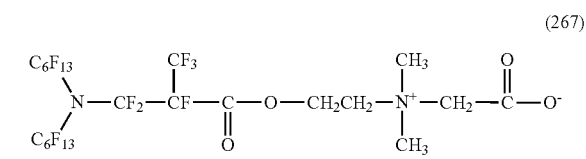
(267)
[Chemical Formula 272]
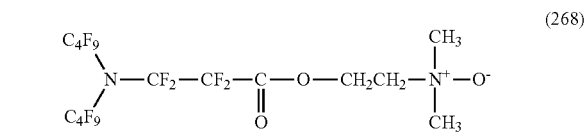
(268)
[Chemical Formula 273]
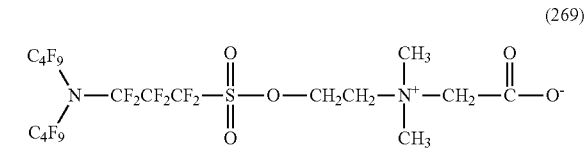
(269)
[Chemical Formula 274]
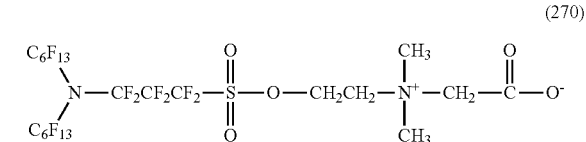
(270)
[Chemical Formula 275]
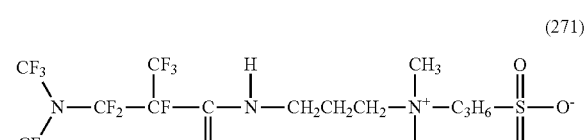
(271)
[Chemical Formula 276]
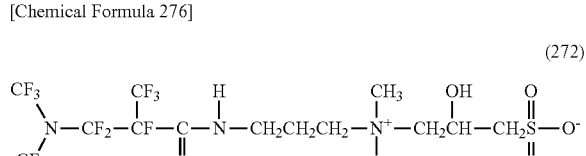
(272)
[Chemical Formula 277]
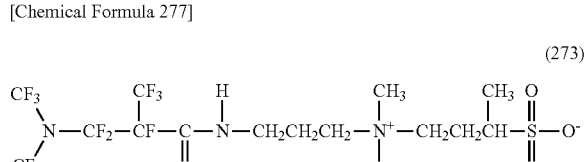
(273)
[Chemical Formula 278]
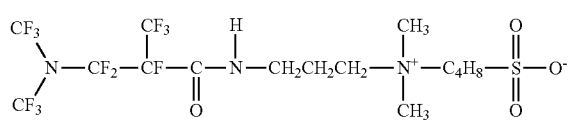
(274)
[Chemical Formula 279]
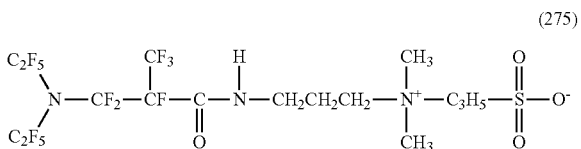
(275)
[Chemical Formula 280]
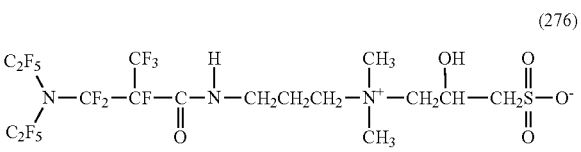
(276)
[Chemical Formula 281]
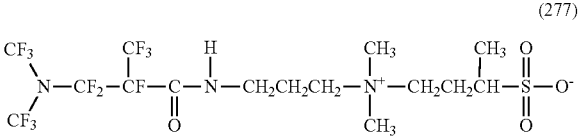
(277)
[Chemical Formula 282]
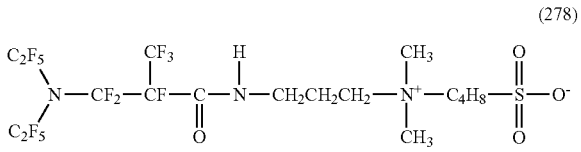
(278)
[Chemical Formula 283]
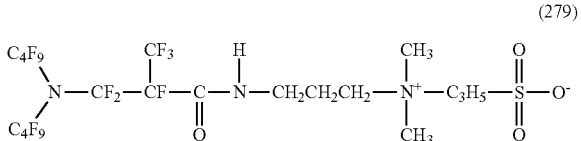
(279)
[Chemical Formula 284]
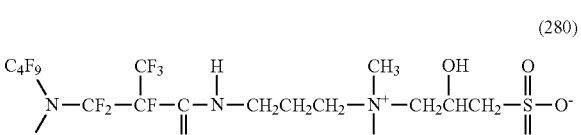
(280)
[Chemical Formula 285]
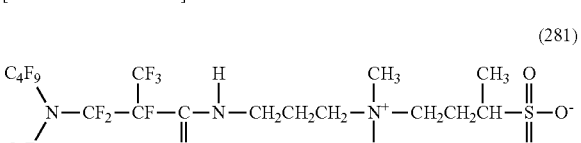
(281)
[Chemical Formula 286]
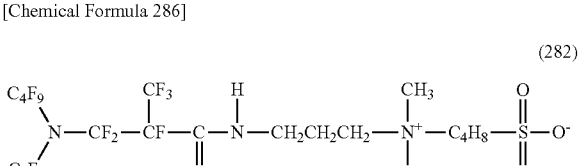
(282)

-continued
[Chemical Formula 287]
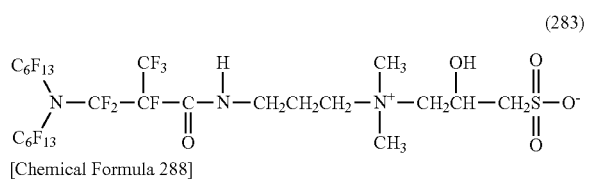
(283)
[Chemical Formula 288]
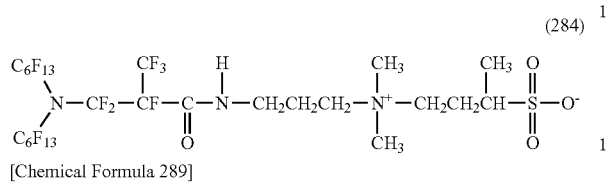
(284)
[Chemical Formula 289]
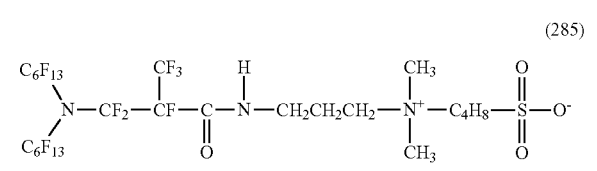
(285)
[Chemical Formula 290]
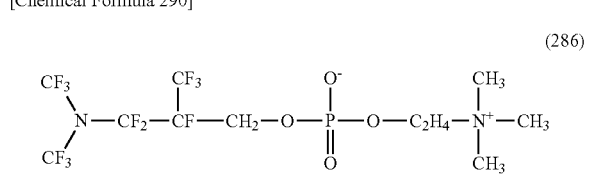
(286)
[Chemical Formula 291]
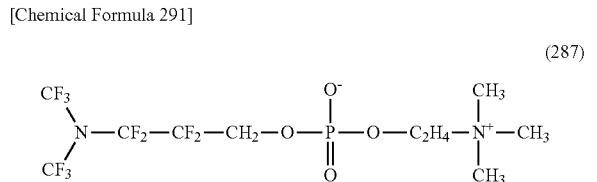
(287)
[Chemical Formula 292]
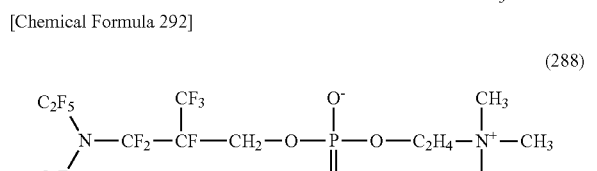
(288)
[Chemical Formula 293]
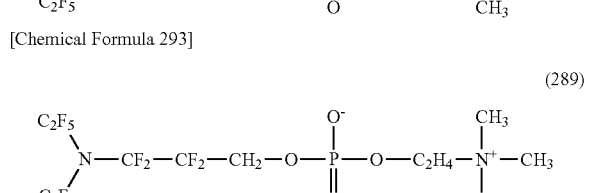
(289)
[Chemical Formula 294]
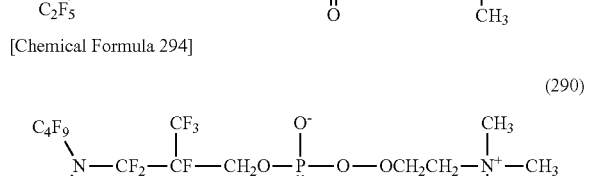
(290)
[Chemical Formula 295]
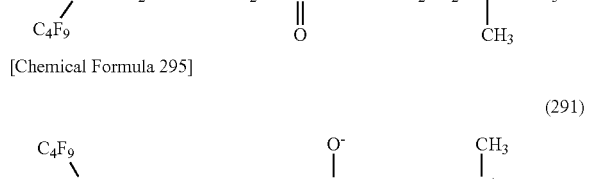
(291)
-continued
[Chemical Formula 296]
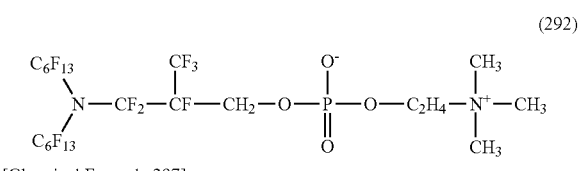
(292)
[Chemical Formula 297]
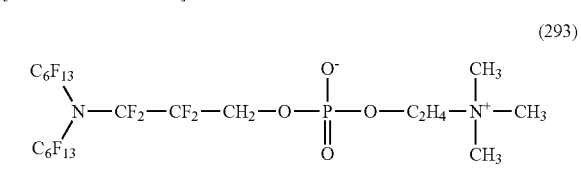
(293)
[Chemical Formula 298]
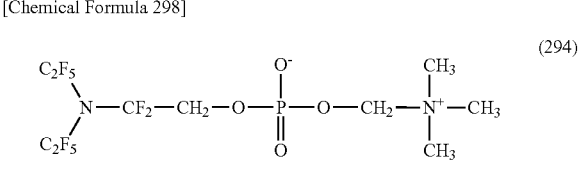
(294)
[Chemical Formula 299]
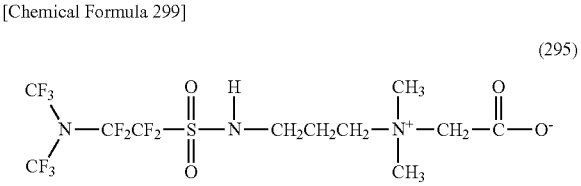
(295)
[Chemical Formula 300]
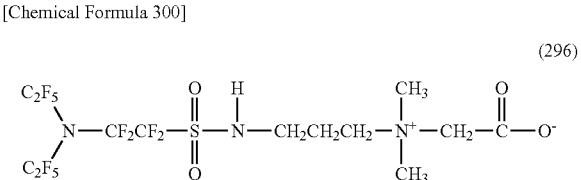
(296)
[Chemical Formula 301]
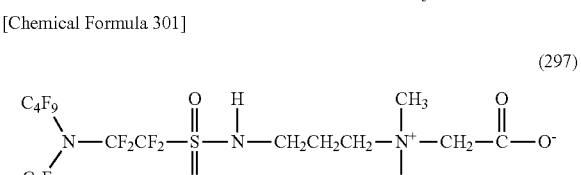
(297)
[Chemical Formula 302]
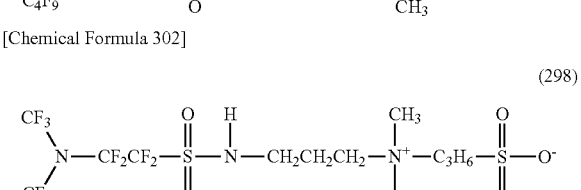
(298)
[Chemical Formula 303]
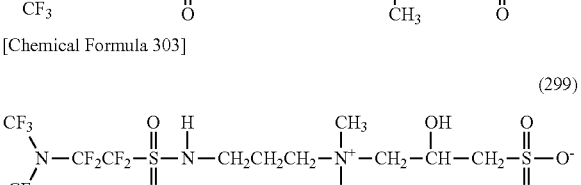
(299)
[Chemical Formula 304]
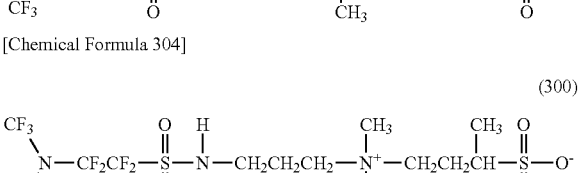
(300)

-continued

[Chemical Formula 305]

(301)
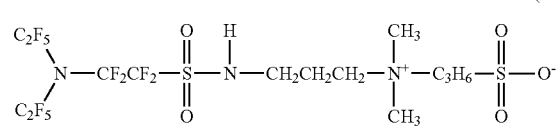

[Chemical Formula 306]

(302)
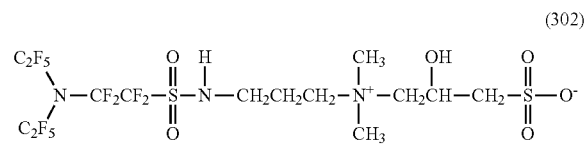

[Chemical Formula 307]

(303)
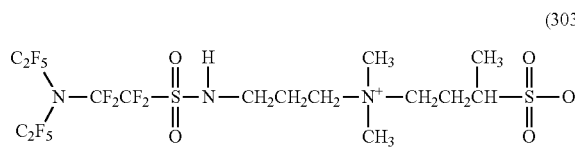

[Chemical Formula 308]

(304)
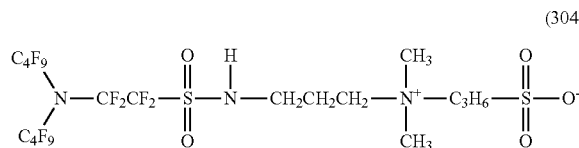

[Chemical Formula 309]

(305)
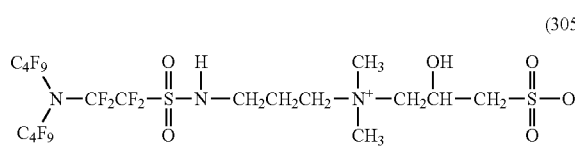

[Chemical Formula 310]

(306)
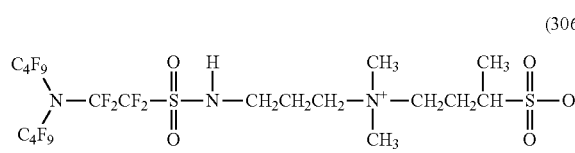

[Chemical Formula 311]

(307)
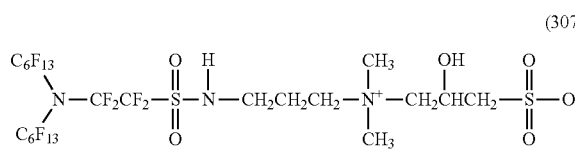

[Chemical Formula 312]

(308)
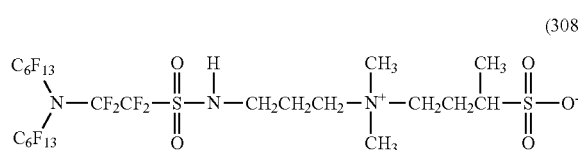

[Chemical Formula 313]

(309)
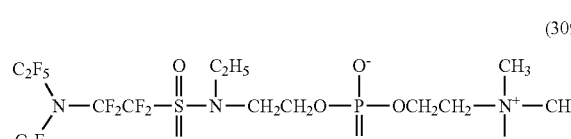

On the contrary, a specific example of a structure of the oil-repellent hydrophilic agent (that is, cyclic nitrogen-containing fluorine compound) represented by the formula (3) or the formula (4) includes structures of the following formulas (310) to (375).

[Chemical Formula 314]

(310)
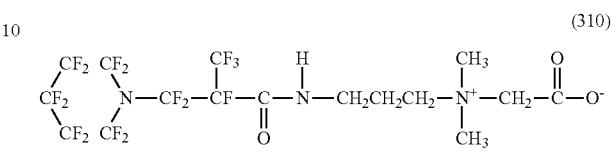

[Chemical Formula 315]

(311)
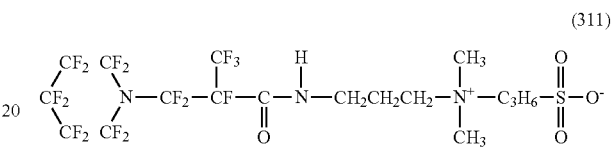

[Chemical Formula 316]

(312)
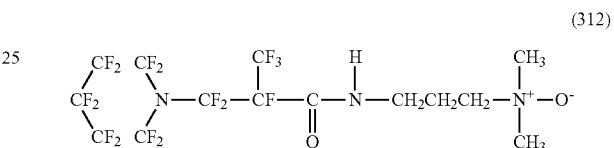

[Chemical Formula 317]

(313)
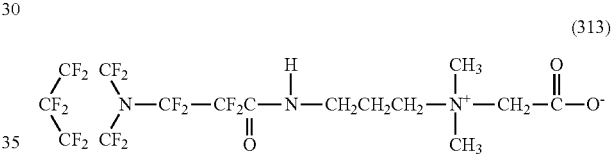

[Chemical Formula 318]

(314)
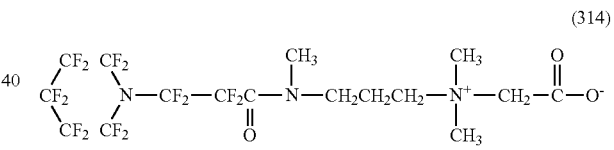

[Chemical Formula 319]

(315)
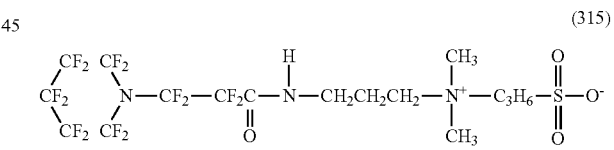

[Chemical Formula 320]

(316)
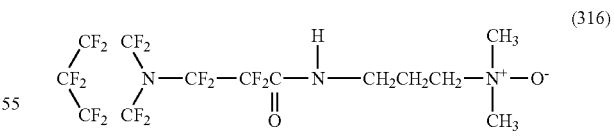

[Chemical Formula 321]

(317)
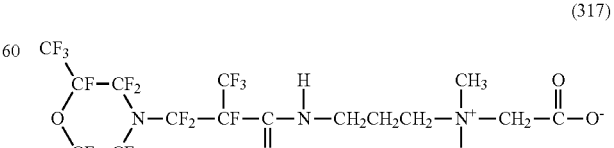

[Chemical Formula 322]
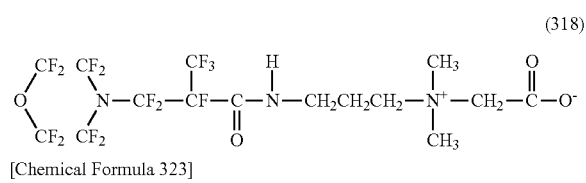
(318)
[Chemical Formula 323]
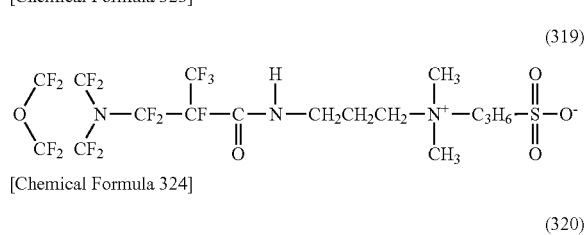
(319)
[Chemical Formula 324]
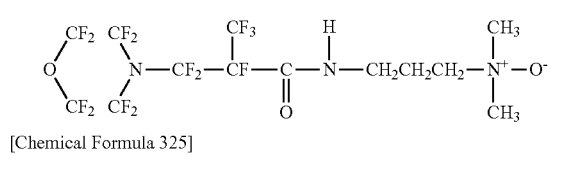
(320)
[Chemical Formula 325]
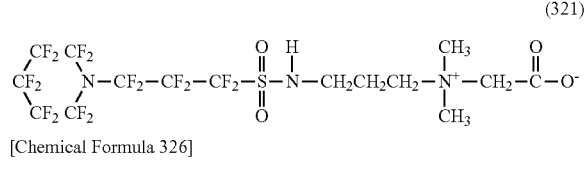
(321)
[Chemical Formula 326]
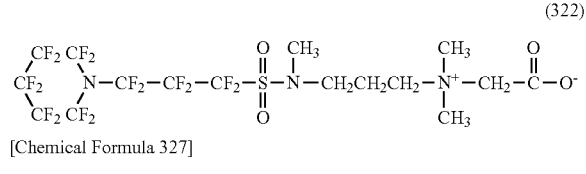
(322)
[Chemical Formula 327]
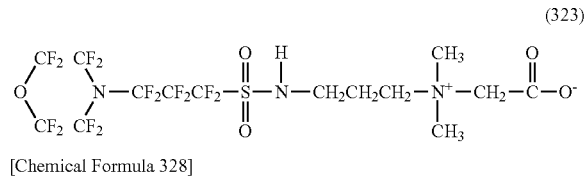
(323)
[Chemical Formula 328]
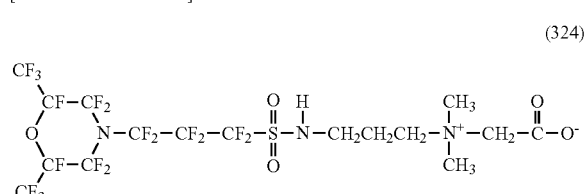
(324)
[Chemical Formula 329]
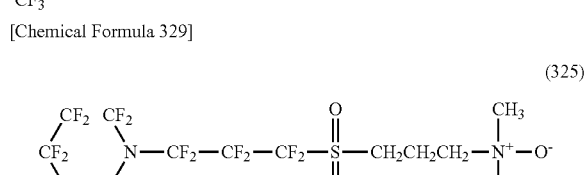
(325)
[Chemical Formula 330]
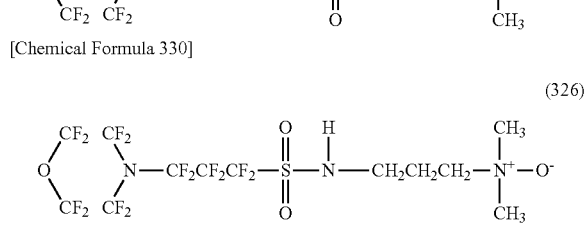
(326)
[Chemical Formula 331]
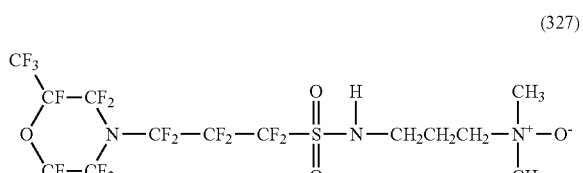
(327)
[Chemical Formula 332]
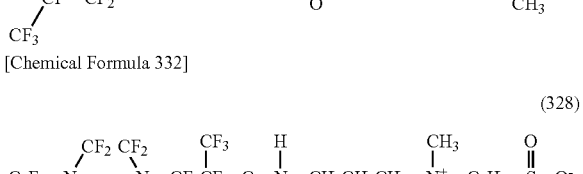
(328)
[Chemical Formula 333]
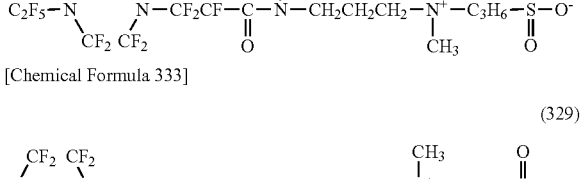
(329)
[Chemical Formula 334]
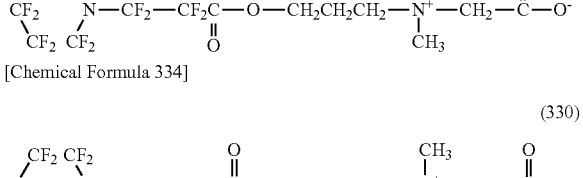
(330)
[Chemical Formula 335]
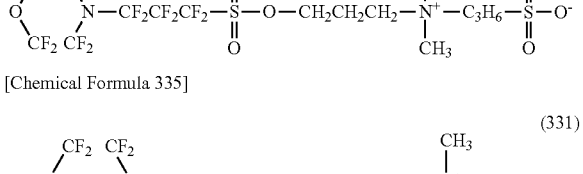
(331)
[Chemical Formula 336]
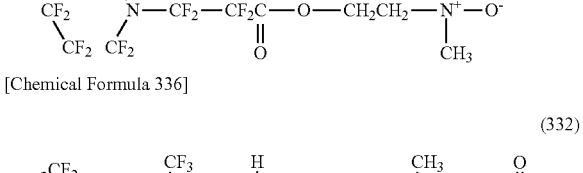
(332)
[Chemical Formula 337]
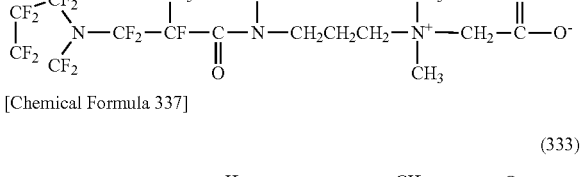
(333)
[Chemical Formula 338]
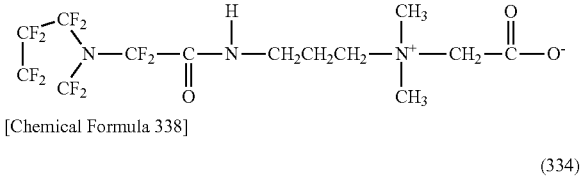
(334)
[Chemical Formula 339]
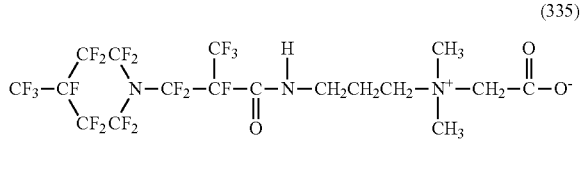
(335)

[Chemical Formula 340]
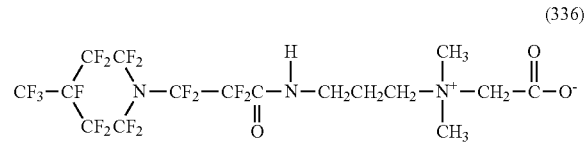
(336)
[Chemical Formula 341]
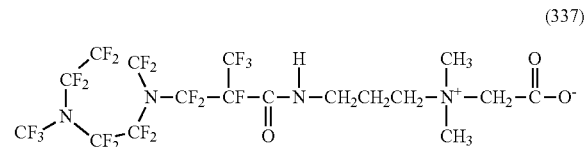
(337)
[Chemical Formula 342]
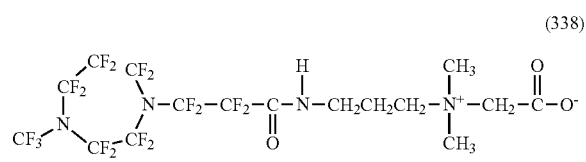
(338)
[Chemical Formula 343]
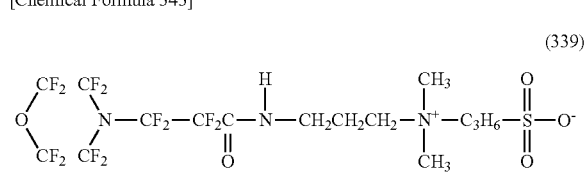
(339)
[Chemical Formula 344]
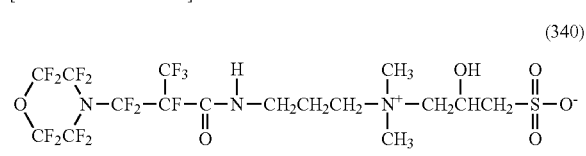
(340)
[Chemical Formula 345]
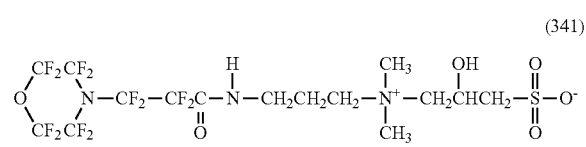
(341)
[Chemical Formula 346]
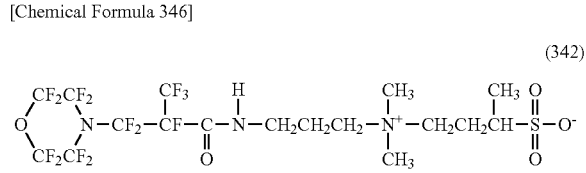
(342)
[Chemical Formula 347]
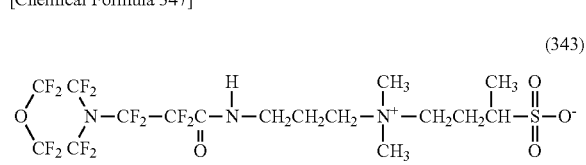
(343)
[Chemical Formula 348]
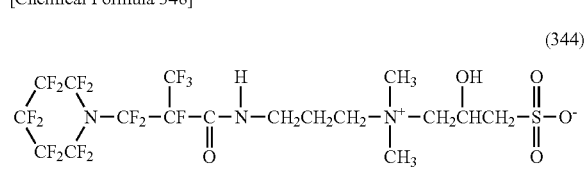
(344)
[Chemical Formula 349]
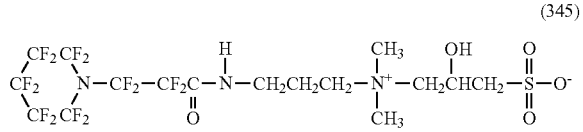
(345)
[Chemical Formula 350]
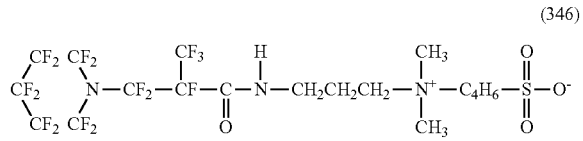
(346)
[Chemical Formula 351]
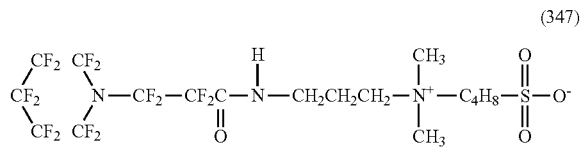
(347)
[Chemical Formula 352]
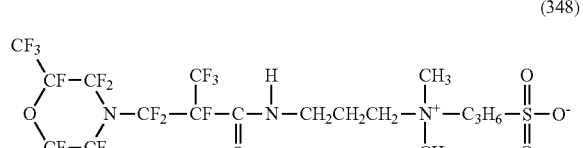
(348)
[Chemical Formula 353]
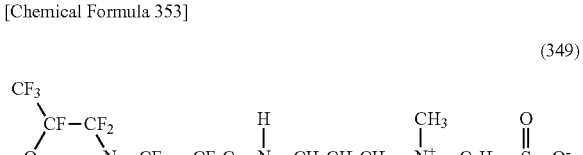
(349)
[Chemical Formula 354]
(350)
[Chemical Formula 355]
(351)
[Chemical Formula 356]
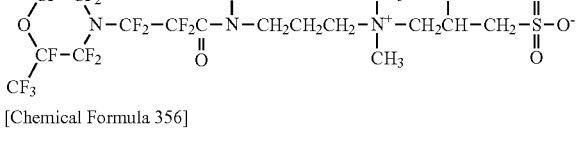
(352)
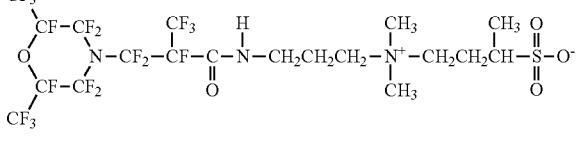

[Chemical Formula 357]
(353)
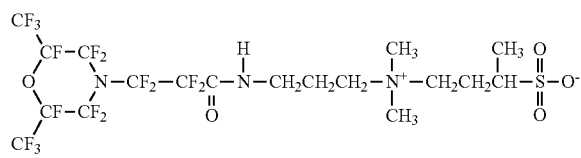
[Chemical Formula 358]
(354)
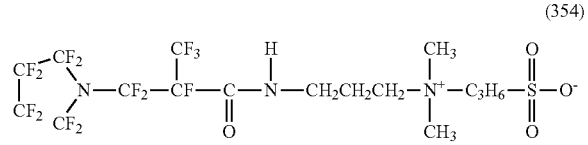
[Chemical Formula 359]
(355)
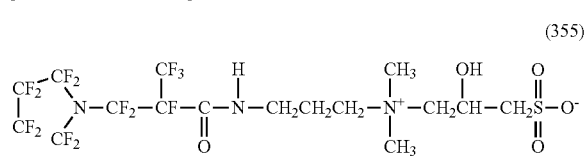
[Chemical Formula 360]
(356)
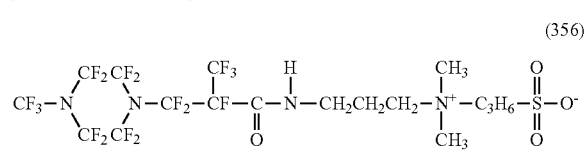
[Chemical Formula 361]
(357)
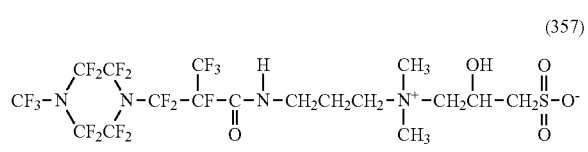
[Chemical Formula 362]
(358)
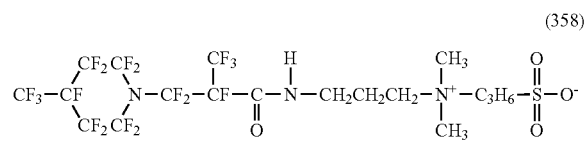
[Chemical Formula 363]
(359)
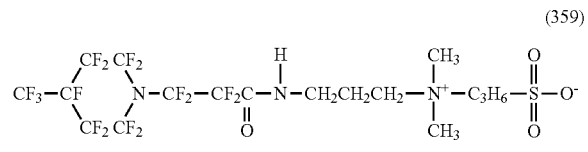
[Chemical Formula 364]
(360)
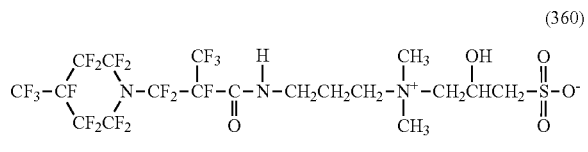
[Chemical Formula 365]
(361)
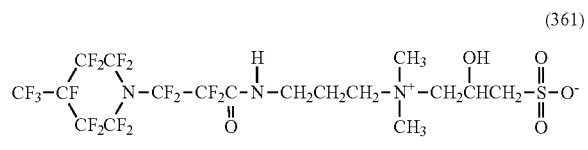
[Chemical Formula 366]
(362)
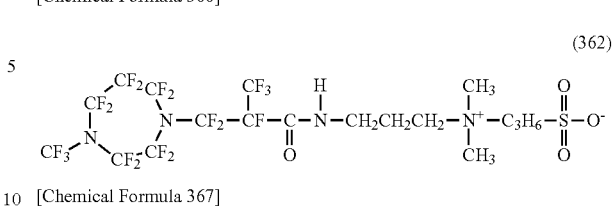
[Chemical Formula 367]
(363)
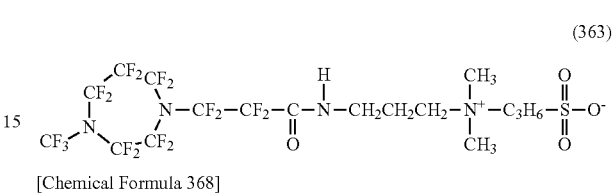
[Chemical Formula 368]
(364)
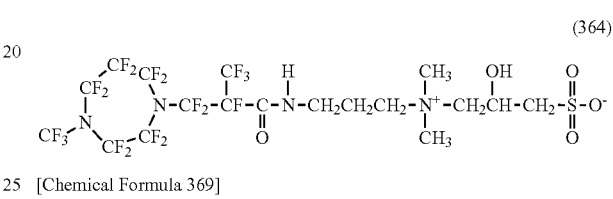
[Chemical Formula 369]
(365)
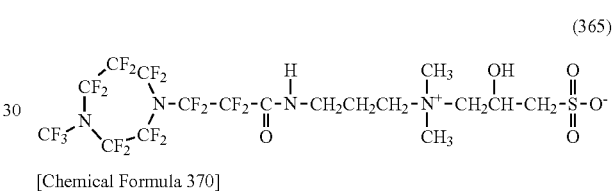
[Chemical Formula 370]
(366)
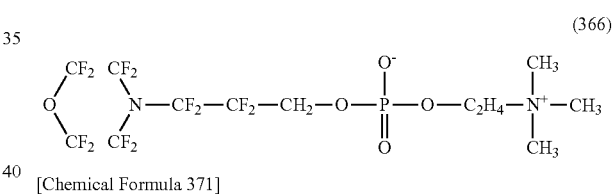
[Chemical Formula 371]
(367)
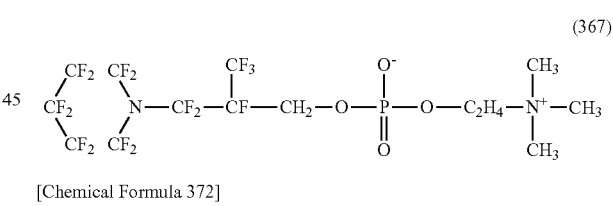
[Chemical Formula 372]
(368)
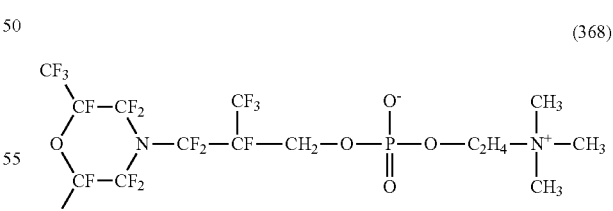
[Chemical Formula 373]
(369)
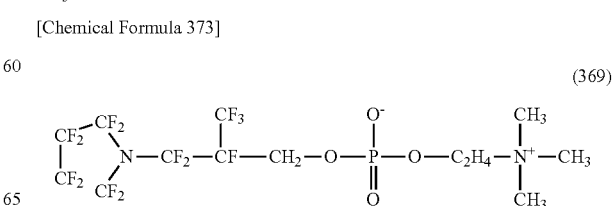

-continued

[Chemical Formula 374]

(370)

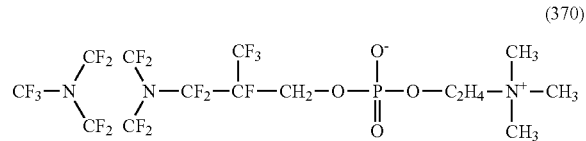

[Chemical Formula 375]

(371)

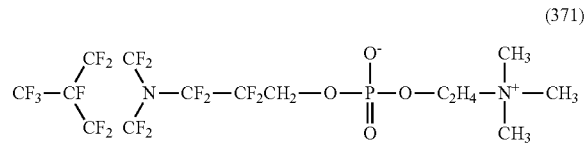

[Chemical Formula 376]

(372)

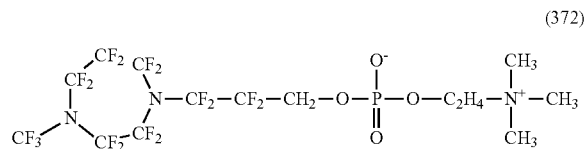

[Chemical Formula 377]

(373)

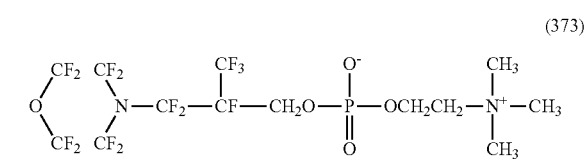

[Chemical Formula 378]

(374)

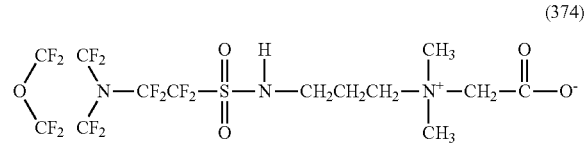

[Chemical Formula 379]

(375)

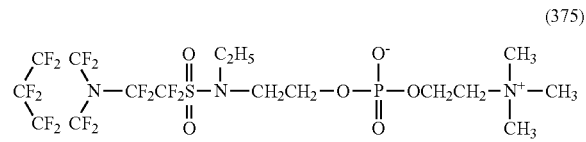

The specific example of the structure of the above-described oil-repellent hydrophilic agent which uses the filter medium in the embodiment is just an example. The technical range of the present invention is not limited to the above specific examples. That is, the oil-repellent hydrophilic agent used in the embodiment may include various oil-repellency imparting groups, and a hydrophilicity imparting group having any of an anion type, a cation type, and an amphoteric type. The oil-repellency imparting groups of which the number is at least one or more, and the hydrophilicity imparting groups of which the number is at least one or more may be provided in a molecule.

The above-described oil-repellent hydrophilic agent independently and sufficiently show the hydrophilic and oil-repellent properties. However, the practical environment extremely varies, for example, containing acid, alkali, oil, and the like. In a case where durability is practically added, it is desirable that the oil-repellent hydrophilic agent is appropriately combined, and thus durability for the practical environment is improved.

The above-described oil-repellent hydrophilic agent may be variously modified in a range without departing from the gist of the present invention. For example, the oil-repellent hydrophilic agent may include two or more oil-repellency imparting groups which are the same as each other or different from each other, in a molecule. In a case where two or more oil-repellency imparting groups are provided in a molecule, the oil-repellency imparting groups may be provided at both terminations of a molecule, or be provided in a molecule chain. The oil-repellent hydrophilic agent may include two or more hydrophilicity imparting groups which are the same as each other or different from each other, in a molecule.

The oil-repellent hydrophilic agent in the embodiment may have two or more bonds which are he same as each other or different from each other, in a linking group. In a case where the linking group is a polymeric type, the number of times of an unit repeating or a bonding order is not particularly limited.

<Evaluation Method of Hydrophilic and Oil-Repellent Properties>

Next, an evaluation method of the hydrophilic and oil-repellent properties of the nitrogen-containing fluorine compound (oil-repellent hydrophilic agent) represented by the formulas (1) to (4) will be described. Here, the hydrophilic and oil-repellent properties can be evaluated, specifically, by a filter permeation test or contact angle measurement.

[Filter Permeation Test]

In the filter permeation test, firstly, the nitrogen-containing fluorine compound represented by the formulas (1) to (4) is dissolved in a solvent such as water or alcohol, so as to obtain a solution. A commercial PTFE membrane filter (ADVANTEC T100A047A: hole diameter of 1 μm, porosity of 79%, thickness of 75 μm) is immersed in the solution, and then drying is performed at room temperature. Water and n-hexadecane is respectively dropped into a filter obtained by the drying at room temperature. In a case where water is permeated into the filter within five minutes, and n-hexadecane is not permeated into the filter even after 30 minutes elapses according to visual determination after the dropping, this case means that the nitrogen-containing fluorine compound has the hydrophilic and oil-repellent properties (that is, the nitrogen-containing fluorine compound is the oil-repellent hydrophilic agent).

Regarding a not-treated PTFE membrane filter, water is not permeated even after 30 minutes elapses, and n-hexadecane is permeated into the filter within five minutes (that is, the nitrogen-containing fluorine compound has water-repellent and lipophilic properties).

In the filter permeation test, regarding a dropping method of water and n-hexadecane, the following conditions are used.

Dropped quantity: 40 to 45 μL/droplet (water)
Dropped quantity: 20 to 25 μL/droplet (n-hexadecane)
Dropping height: 5 cm from surface of PTFE membrane filter
Dropping tool: polyfiller
Measurement temperature: room temperature (22±1° C.)

In the filter permeation test, nonwoven fabric formed of PP/PE and the like may be used instead of the PTFE membrane filter.

[Contact Angle Measurement]

In contact angle measurement, firstly, the nitrogen-containing fluorine compound represented by the formulas (1) to (4) is dissolved in methanol, thereby 2.0 mass % of a methanol solution is obtained. A soda glass plate is immersed in a 1N potassium hydroxide aqueous solution for two hours, in advance, at room temperature for room temperature. Then, washing with pure water, and washing with acetone is performed, and then drying is performed. Such a soda glass plate is immersed (dip-coated) in the methanol solution and is dried at room temperature so as to remove methanol, and thus a coating film is formed on the glass plate. Then, water and n-hexadecane is dropped onto the coating film, and a contact angle between the coating film and a liquid droplet is measured at room temperature (22±1° C.). As a result of the contact angle measurement, in a case where the contact angle of water with the coating film is equal to or less than 20°, and the contact angle of n-hexadecane is equal to or more than 40°, this case means that the nitrogen-containing fluorine compound has the hydrophilic and oil-repellent properties (that is, the nitrogen-containing fluorine compound is the oil-repellent hydrophilic agent).

In the contact angle measurement, regarding a dropping method of water and n-hexadecane, the following conditions are used.

Dropped quantity: 2 μL/droplet (water)
Dropped quantity: 2 μL/droplet (n-hexadecane)
Measurement temperature: room temperature (22±1° C.)

Such a contact angle may be measured by a liquid droplet method with an automatic contact angle meter (manufactured by Kyowa Interface Science Co., Ltd, "Drop Master 701").

<Method for Producing Oil-Repellent Hydrophilic Agent>

Next, a method for producing an oil-repellent hydrophilic agent in the embodiment will be described.

In the method for producing an oil-repellent hydrophilic agent in the embodiment, the nitrogen-containing fluorine compound represented by the formulas (1) to (4) is manufactured by using carboxylic acid halide or sulfonic acid halide which has a nitrogen-containing perfluoroalkyl group represented by the following formula (5) or (6), as a raw material. More specifically, the nitrogen-containing fluorine compound represented by the formula (1) or (2) is manufactured by using carboxylic acid halide or sulfonic acid halide which has a nitrogen-containing perfluoroalkyl group represented by the following formula (5), as a raw material. The nitrogen-containing fluorine compound represented by the formula (3) or (4) is manufactured by using carboxylic acid halide or sulfonic acid halide which has a nitrogen-containing perfluoroalkyl group represented by the following formula (6), as a raw material.

[Chemical Formula 380]

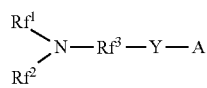

(5)

[Chemical Formula 381]

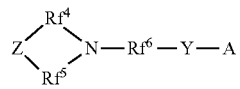

(6)

Here, each of $Rf^1$ and $Rf^2$ in the formula (5) is a straight-chain or branched perfluoroalkyl group which is the same as or different from each other, and has 1 to 6 carbon atoms. $Rf^3$ is a straight-chain or branched perfluoroalkylene group which has 1 to 6 carbon atoms.

Each of $Rf^1$ and $Rf^2$ is a straight-chain or branched perfluoroalkyl group which is the same as or different from each other, and has 1 to 4 carbon atoms. $Rf^3$ is a straight-chain or branched perfluoroalkylene group which has 1 to 4 carbon atoms.

Each of $Rf^4$, $Rf^4$, and $Rf^6$ in the formula (6) is a straight-chain or branched perfluoroalkylene group which is the same as or different from each other, and has 1 to 6 carbon atoms.

Each of $Rf^4$, $Rf^5$, and $Rf^6$ is a straight-chain or branched perfluoroalkylene group which is the same as or different from each other, and has 1 to 4 carbon atoms.

Z includes any of an oxygen atom, a nitrogen atom, a $CF_2$ group, and a CF group. In a case where Z is a nitrogen atom or a CF group, a perfluoroalkyl group branched from Z may be bonded to the Z.

Y in the formulas (5) and (6) is CO or $SO_2$.

In the formulas (5) and (6), A is any one halogen atom selected from a group consisting of fluorine, chlorine, bromine, and iodine.

The method for producing an oil-repellent hydrophilic agent in the embodiment varies depending on the type of X indicated in the formulas (1) to (4). This will be described below by using a case.

[Case of Anion Type]

Firstly, a case where the nitrogen-containing fluorine compound represented by the formula (1) or the formula (3) is manufactured will be described.

The raw material may be dropped so as to cause a neutralization reaction, and then be dried and solidified. A target material may be extracted from a solid obtained by drying and solidifying with a solvent in which the target material is allowed to be dissolved, and M(A), $M(A)_2$, or $M(A)_3$ which is generated as a byproduct is not allowed to be dissolved. Then, the extraction solvent may be dried and solidified, and thus the target material may be obtained. Regarding the raw material represented by the formula (5) or the formula (6), in a case where Y is CO (in a case of carboxylate series), the raw material is dropped in M(OH) (M indicates Li, Na, K, Ca, Mg, Al, and the like; and m indicates 1 in a case of a monovalent cation such as Li, Na, and K, indicates 2 in a case of a bivalent cation such as Ca and Mg, and indicates 3 in a case of a trivalent cation such as Al) which is provided in a form of an aqueous solution. In a case where Y is $SO_2$ (in a case of sulfonic acid series), the raw material is dropped in $M(OH)_m$ (M indicates Li, Na, K, $R^1R^2R^3R^4N^+$, Ca, Mg, Al, and the like; m indicates 1 in a case of a monovalent cation such as Li, Na, and K, indicates 2 in a case of a bivalent cation such as Ca and Mg, and indicates 3 in a case of a trivalent cation such as Al; $R^1$ to $R^4$ are hydrogen atoms or straight-chain or branched alkyl groups which have independently 1 to 20 carbon atoms) which is provided in a form of an aqueous solution. If necessary, the salt may be transformed into carboxylic acid or sulfonic acid by using sulfuric acid and the like, and be distilled. Then, a desired salt may be obtained again by using $M(OH)_m$ and thus purity of the salt may be increased.

Next, a case where the nitrogen-containing fluorine compound represented by the formula (2) or the formula (4) is manufactured will be described.

Specifically, for example, in a case where a linking group R having an amide bond is inserted between the oil-repellency imparting group (nitrogen-containing perfluoroalkyl group) and an anion type hydrophilicity imparting group, firstly, nitrogen-containing perfluoroalkylcarbonyl fluoride or sulfonyl fluoride is caused to react with aminoalkyl carboxylic acid or aminophenyl sulfonic acid. Then, reaction with alkali hydroxide is performed, and thus an alkali metal salt of carboxylic acid or sulfonic acid having an amide bond is obtained.

For example, in a case where a linking group R having an ester bond is inserted between the oil-repellency imparting group (nitrogen-containing perfluoroalkyl group) and an anion type hydrophilicity imparting group, firstly, nitrogen-containing perfluoroalkylcarbonyl fluoride or sulfonyl fluoride is caused to react with hydroxyphenyl organic acid. Then, reaction with alkali hydroxide is performed, and thus an alkali metal salt of carboxylic acid or sulfonic acid having an ester bond is obtained.

For example, in a case where a linking group R having an ether bond is inserted between the oil-repellency imparting group (nitrogen-containing perfluoroalkyl group) and an anion type hydrophilicity imparting group, firstly, nitrogen-containing perfluoroalkylcarbonyl fluoride is reduced by lithium aluminum hydride ($LiAlH_4$) or sodium borohydride ($NaBH_4$), and thus alcohol having a nitrogen-containing perfluoroalkyl group is generated. Then, after potassium alcoholate is obtained by t-butoxy potassium and the like, reaction with a metal salt of halogenated organic acid is performed. Thus, an alkali metal salt of carboxylic acid having an ether bond is obtained.

[Case of Cation Type]

Specifically, for example, in the raw material represented by the formula (5) or the formula (6), amide-bonding of nitrogen-containing perfluoroalkylcarbonyl fluoride or sulfonyl fluoride to N,N-dialkylamino alkyleneamine is performed so as to cause tertiary amine to be provided at the termination, and then quaternization is performed by an alkylating agent such as methyl iodide ($CH_3I$), methyl bromide ($CH_3Br$), or dimethyl sulfate ($(CH_3)_2SO_4$). Thus, a nitrogen-containing fluorine compound having a cation type hydrophilicity imparting group is obtained.

For example, in the raw material represented by the formula (5) or the formula (6), ether-bonding of nitrogen-containing perfluoroalkylcarbonyl fluoride or sulfonyl fluoride to N,N-dialkylamino alkylene alcohol so as to cause tertiary amine to be provided at the termination, and then quaternization is performed by an alkylating agent such as methyl iodide ($CH_3I$), methyl bromide ($CH_3Br$), or dimethyl sulfate ($(CH_3)_2SO_4$). Thus, a nitrogen-containing fluorine compound having a cation type hydrophilicity imparting group is obtained.

[Case of Amphoteric Type]

Specifically, for example, in a case of a carboxy betaine type, firstly, in the raw material represented by the formula (5) or the formula (6), amide-bonding of nitrogen-containing perfluoroalkylcarbonyl fluoride or sulfonyl fluoride to N,N-dialkylamino alkyleneamine is performed or ether-bonding of nitrogen-containing perfluoroalkylcarbonyl fluoride or sulfonyl fluoride to N,N-dialkylamino alkylene alcohol, so as to cause tertiary amine to be provided at the termination. Then, reaction with sodium monochloroacetate is performed. Thus, a nitrogen-containing fluorine compound having an amphoteric type hydrophilicity imparting group is obtained.

For example, in a case of a sulfobetaine type, as described above, after tertiary amine is caused to be provided at the termination, reaction with a cyclic sulfonic acid ester compound represented by 1,3-propane sultone and the like is performed. Thus, a nitrogen-containing fluorine compound having an amphoteric type hydrophilicity imparting group is obtained.

For example, in a case of an amine oxide type, as described above, after tertiary amine is caused to be provided at the termination, reaction with a hydrogen peroxide is performed. Thus, a nitrogen-containing fluorine compound having an amphoteric type hydrophilicity imparting group is obtained.

For example, in a case of a phosphobetaine type, an alcohol substance obtained by reducing nitrogen-containing perfluorocarbonyl fluoride, or a substance obtained in a manner that sulfonamidation of nitrogen-containing perfluoroalkyl sulfonyl fluoride is performed by amino alcohol so as to cause a hydroxyl group to be provided at the termination is caused to react with phosphorus oxychloride in a state where a base of trimethylamine and the like is provided. Thus, dichlorophosphate ester having a nitrogen-containing perfluoroalkyl group is obtained. Then, the obtained dichlorophosphate ester having a nitrogen-containing perfluoroalkyl group is caused to react with bromoethanol, and then reaction with trimethylamine under a silver carbonate catalyst, so as to obtain a quaternary ammonium salt. Finally, hydrolysis is performed, and thus a nitrogen-containing fluorine compound having an amphoteric type hydrophilicity imparting group is obtained.

<Binder>

In the filter medium in this embodiment, the nitrogen-containing fluorine compound (oil-repellent hydrophilic agent) represented by the formulas (1) to (4) is singly provided or is combined and provided with a binder on the surface of the channel formed by the base. In other words, the nitrogen-containing fluorine compound (oil-repellent hydrophilic agent) exists on at least the portion of the surface of the base. In the filter medium in this embodiment, because spillage of the nitrogen-containing fluorine compound due to a liquid to be separated does not occur, the nitrogen-containing fluorine compound is fixed to the surface of the base.

Specifically, in the filter medium in this embodiment, a portion or the entirety of the base may be coated by a coating film which contains a nitrogen-containing fluorine compound (oil-repellent hydrophilic agent) represented by the formulas (1) to (4) or may be coated by a coating film which contains a binder and the nitrogen-containing fluorine compound (oil-repellent hydrophilic agent) represented by the formulas (1) to (4).

The coating film has a case of being formed from only the above-described nitrogen-containing fluorine compound (oil-repellent hydrophilic agent) and a case of including the binder. In a case of including the binder, the mass composition ratio of the oil-repellent hydrophilic agent and the binder is preferably in a range of a pair of 0.2 to 99.9 and 99.8 to 0.1, more preferably in a range of a pair of 2 to 98 and 98 to 2, and further preferably in a range of a pair of 10 to 90 and 90 to 10. If the mass composition ratio of the oil-repellent hydrophilic agent is equal to or less than 0.2, the hydrophilic and oil-repellent properties are sufficiently obtained. Thus, this range is preferable. If the mass composition ratio of the oil-repellent hydrophilic agent is equal to or more 99.9, an effect of fixing the hydrophilic and oil-repellent agent by the binder is relatively improved. Thus, this range is preferable. If adhesion to the base or durability of a coating film is to be added, the mass composition ratio is particularly preferably in a range of a pair of 10 to 90 and 90 to 10.

Specific examples of the binder include an organic binder (resin) and an inorganic binder (inorganic glass). As the organic binder (resin), for example, a thermoplastic resin, a thermoplastic elastomer, a thermosetting resin, an UV curable resin, and the like are provided. Specific examples include a thermoplastic resin such as polyvinyl chloride, polyethylene, polypropylene, polycarbonate, polyester, polystyrene, a silicone resin, polyvinyl acetal, polyvinyl alcohol, an acrylic polyol resin, a polyester polyol resin, a urethane resin, a fluororesin, and a thermoplastic acrylic resin; and a thermosetting resin such as an epoxy resin, a phenol resin, and a thermosetting acrylic resin.

Hydrophilic polymer is preferably used as the binder, in order to exhibit the characteristics of the hydrophilic and oil-repellent properties up to the maximum. As the hydrophilic polymer, a substance which contains a hydroxyl group for causing adhesion to the base or interaction (such as hydrogen bond) with a hydrophilic and oil-repellent composite is preferable.

As the hydrophilic polymer, specifically, for example, polysaccharide such as polyvinyl alcohol, polyvinyl butyral, and cellulose, and derivatives thereof are exemplified. These substances may be singly used or be used in combination of two types or more. The hydrophilic polymer may be cross-linked by a crosslinking agent. Such crosslinking causes durability of a coating film to be improved.

The crosslinking agent is not particularly limited, and may be appropriately selected in accordance with the purpose. Specific examples of the crosslinking agent include an epoxy compound, an isocyanate compound, an aldehyde compound, an ultraviolet crosslinking type compound, a leaving group-containing compound, a carboxylic acid compound, and a urea compound.

Specific examples of the inorganic binder (inorganic glass) include a silane compound such as trialkoxysilane represented by a chemical formula $[R^{14}Si(OR^{15})_3]$, tetraalkoxysilane represented by a chemical formula $[Si(OR^{16})_4]$ ($R^{14}$ to $R^{16}$ each independently is alkyl group having 1 to 6 carbon atoms); and water glass. Among these substances, water glass is preferable because an effect of improving durability is high. A method of forming a coating film will be described later.

<Base>

In the filter medium in the embodiment, the channel for a liquid to be separated is configured by the base. Specifically, in the filter medium in the embodiment, in a case where the base is a fiber assembly, a space between fibers functions as the channel for a liquid. In a case where the base is an aggregate of particles, specifically, in a case where the base is formed by stacking particles (filling with particles), a void between particles functions as the channel for a liquid. In a case where the base is a porous medium having a continuous pore, the continuous pore of the porous medium functions as the channel for a liquid.

The material of the base is not particularly limited as long as the material can form a channel for a liquid to be separated. The material of the base may be an organic matter or an inorganic matter. In addition, the material of the base 17 may be a composite of an organic matter and an inorganic matter. Thus, as a form of the base in the filter medium in this embodiment, an aggregate of a fibrous organic matter, an aggregate of a particulate organic matter, an aggregate of a fibrous inorganic matter, and an aggregate of a particulate inorganic matter, a porous medium of an organic matter, a porous medium of an inorganic matter, and the like are exemplified.

Here, the organic matter usable as the base is not particularly limited. Specific examples of the organic matter include various resins such as a thermoplastic resin, a thermoplastic elastomer, a thermosetting resin, and an UV curable resin, a natural polymer such as cellulose, and derivatives thereof. Specific examples include a thermoplastic resin such as polyvinyl chloride, polyethylene, polypropylene, polycarbonate, polyester, polystyrene, a silicone resin, polyvinyl acetal, polyvinyl alcohol, polyamide, polyimide, an acrylic polyol resin, a polyester polyol resin, a urethane resin, a fluororesin, and a thermoplastic acrylic resin, or a thermosetting resin such as an epoxy resin, a phenol resin, and a thermosetting acrylic resin. Pulp, cotton, or the like is exemplified.

A material usable as the base is not particularly limited. Specific examples of the material include a carbon-based substance such as active carbon, and an inorganic substance such as anthracite, sand, gravel, garnet, glass, ceramics, and metal.

Examples of fiber useable as the base may include an organic fiber such as synthetic fiber, natural fiber, and cellulosic fiber, or an inorganic fiber such as metallic fiber, carbon fiber, glass fiber, and ceramics fiber. These fibers may be singly used or be used by mixing or mixed-spinning two types or more thereof. As a fiber assembly usable as the base, for example, a film-like or sheet-like aggregate such as filter paper, woven fabric, knitted fabric, nonwoven fabric, a net, and mesh may be exemplified. As the fiber assembly, an object obtained by winding fiber (winding to be columnar) to form a filter may be used. In the fiber assembly, fibers may be stuck to each other or be fused in a range without closing a channel for a liquid between fibers.

As particles usable as the base, for example, inorganic particles such as anthracite, and, gravel, garnet, glass, ceramics, and metal may be exemplified. These particles may be singly used or be used as a mixture of two types or more thereof. As an example of an aggregate of particles usable as the base, an object (for example, sand filter) in which a plurality of particles are stacked on a porous substrate, and an object in which a porous bag or a porous container is filled with a plurality of particles may be exemplified. In the aggregate of particles, particles may be stuck to each other or be sintered in a range without closing a channel for a liquid between particles.

Examples of the porous medium which is usable as the base, and has a continuous pore may include an organic porous medium such as porous fluororesin, porous polypropylene, porous polyethylene, porous polyester, porous polystyrene, porous polysulfone, porous polyethersulfone, porous vinylon, porous nylon, and porous cellulose; or an inorganic porous medium such as active carbon, ceramics, sintered metal, silica, alumina, zeolite, calcium carbonate, and clay mineral. These porous media may be singly used or be used as a mixture of two types or more thereof. The shape of the porous medium is, for example, a film shape, a sheet shape, and a particle shape. As the film-like and a sheet-like porous medium, for example, a membrane filter, and a hollow-fiber membrane may be exemplified. The particulate porous medium may be used as the base, in a form of an aggregate, for example. In an aggregate of the particulate porous medium, particulate porous media may be stuck to each other or be sintered in a range without closing a continuous pore.

The pore diameter (that is, channel diameter) of the continuous pore in the porous medium is preferably in a range of 0.1 to 180 μm, more preferably in a range of 0.1 to 150 μm, further preferably in a range of 0.5 to 75 μm, and particularly preferably in a range of 1 to 50 μm. If the pore diameter of the porous medium is in the above range, oil is not permeated, and a water passing rate in a practically-appropriate range is obtained. Thus, such a porous medium is preferable as the base for oil-water separation.

The base which may be used in the filter medium in this embodiment is not particularly limited. Specific examples of such a base include filter paper which is mainly formed of cellulose, a filter cloth (polyester, polyethylene, polypropylene, polytetrafluoroethylene, nylon, polyimide, polyacrylonitrile, polysulfone, polyethersulfone, polyphenylene sulfide, and the like), a nonwoven filter (polyester, polyethylene, polypropylene, rayon, nylon, polyphenylene sulfide, and the like), a fibrous filter (resin, glass, ceramics, and metal), a sintered filter (object obtained by directly bonding powder or fiber of metal, ceramics, plastics, and the like by heat and pressure), a metal net, a metal mesh, a filter plate (an object obtained by performing compression molding of cellulose, glass fiber, and the like), and an object in which silica, alumina, zeolite, calcium carbonate, talc, a clay mineral such as montmorillonite, and the like are stacked (or filled).

The filter medium in this embodiment, which is configured by the base having hydrophilicity is preferable because of having high holding properties to the base in which a coating film containing an oil-repellent hydrophilic agent is provided. Here, an organic matter usable as the base having hydrophilicity is not particularly limited. As such an organic matter, an organic matter which itself can be subjected to hydrophilic and oil-repellent treatment, and an organic matter which is subjected to hydrophilization treatment and then is subjected to hydrophilic and oil-repellent treatment are provided. As the organic matter which itself can be subjected to hydrophilic and oil-repellent treatment, an organic matter having a polar group is appropriate. Examples of such an organic matter include various resins such as a thermoplastic resin, a thermoplastic elastomer, a thermosetting resin, and an UV curable resin, a natural polymer such as cellulose, and derivatives thereof. Specific examples include a thermoplastic resin such as polyvinyl chloride, polycarbonate, polyester, polyvinyl acetal, polyvinyl alcohol, an acrylic polyol resin, a polyester polyol resin, a urethane resin, and a thermoplastic acrylic resin, or a thermosetting resin such as an epoxy resin, a phenol resin, and a thermosetting acrylic resin. Pulp, cotton, or the like is exemplified.

As the base having hydrophilicity, there may be provided a polymeric material in which a functional group having hydrophilicity, such as a hydroxyl group, a carboxyl group, an amino group, a ketone group, and a sulfone group is introduced by a chemical reaction with acid, alkali, a sulfurous gas, or a fluorine gas.

As the base having hydrophilicity, there may be provided an organic matter in which the surface of polymer is subjected to hydrophilization by a finishing agent having hydrophilicity. Examples of the finishing agent having hydrophilicity include polyethylene glycol, polycarboxylic acid, polyisocyanate, a vinyl group, a glycidyl ether group, polyamine, polyalkylene oxide containing N-methoxymethylol and the like, a polymeric electrolyte, and a cellulose-based substance having hydrophilicity.

As the base having hydrophilicity, a fluororesin, polypropylene, polyethylene, and polystyrene of which the surface is subjected to hydrophilization by any one or more of plasma treatment, corona treatment, and ozone treatment may be provided.

Chemical treatment, plasma treatment, corona treatment, or the like may be performed on various resins having a polar group, natural polymer such as cellulose, and derivatives thereof, and the like, which are described above.

It is preferable that porous vinylon, porous nylon, porous polyvinyl alcohol, porous vinyl copolymer containing polyalkylene oxide chain, porous cellulose, and composites thereof are used as a porous medium which is the base having a polar group.

It is preferable that porous fluororesin, porous polypropylene, porous polyethylene, porous polystyrene, porous polyester, porous polysulfone, porous polyethersulfone (which are subjected to hydrophilization treatment), and composites thereof are used as the porous medium which is the base having a polar group.

The channel width (that is, width of a channel configured by the base) of the filter medium in the embodiment is preferably in a range of 0.1 to 180 μm, more preferably in a range of 0.1 to 150 μm, further preferably in a range of 0.5 to 75 μm, and particularly preferably in a range of 1 to 50 μm. If the channel width of the filter medium is in the above range, oil is not permeated, and a water passing rate in a practically-appropriate range is obtained. Thus, such a filter medium is preferable.

In a case where the base is a porous medium, the porous medium may hold a nitrogen-containing fluorine compound (oil-repellent hydrophilic agent) represented by the formulas (1) to (4).

As a holding method, for example, a method in which a porous medium to be held is added to a dissolving liquid or a dispersion liquid of the nitrogen-containing fluorine compound (oil-repellent hydrophilic agent) and is dried so as to remove a solvent may be appropriately applied. As a proportion for holding, selection to cause the mass composition ratio of an oil-repellent hydrophilic agent and a porous medium to be held to be in a range of a pair of 1 to 50 and 99 to 50 is preferable in a point of characteristics of the hydrophilic and oil-repellent properties.

In a case where the obtained porous medium is a particulate porous medium, the surface of the base such as filter paper, nonwoven fabric, or a cartridge filter is subjected to fixing treatment, and thus more exceptional oil-water separation performance is obtained. Thus, this case is more preferable. In order to perform fixation to the base, the above described resins or glassiness may be used.

The base of the filter medium in this embodiment may have a form in a manner that formation is performed to be fibrous or particulate, by a resin composition which contains the above-described organic matter (resin) and one or more of nitrogen-containing fluorine compounds (oil-repellent hydrophilic agents) represented by the formulas (1) to (4). That is, the above-described oil-repellent hydrophilic agent may be used as an additive for imparting the function of the hydrophilic and oil-repellent properties to various resins.

The resin composition may further contain an additive as an arbitrary component, in addition to the oil-repellent hydrophilic agent and a resin. The additive is used for applying function such as a fluidity improving agent, a surfactant, a flame retardant, a conductivity imparting agent, and an antifungal agent, which is different from hydrophilicity and oil repellency.

A method of forming the resin composition is not particularly limited as long as the method is a method in which an oil-repellent hydrophilic agent which is appropriately selected in accordance with the type of a resin can be dispersed or dissolved. Specifically, for example, as a method of mixing an oil-repellent hydrophilic agent to a thermoplastic resin, there is a method of mixing by kneading and the like by an extrusion method or a rolling method.

In the resin composition, the mass composition ratio of the oil-repellent hydrophilic agent and the resin is preferably in a range of a pair of 0.2 to 99.9 and 99.8 to 0.1, more preferably in a range of a pair of 2 to 98 and 98 to 2, and further preferably in a range of a pair of 10 to 90 and 90 to 10. If the mass composition ratio of the oil-repellent hydrophilic agent is equal to or more than 0.2, it is possible to sufficiently exhibit the hydrophilic and oil-repellent function. Thus, this ratio is preferable. If the mass composition ratio of the oil-repellent hydrophilic agent is equal to or more than 90, moldability is easily held without damaging resin physical properties. Thus, this range is preferable.

Further, in a case where the base of the filter medium in this embodiment is a porous medium, one or more of nitrogen-containing fluorine compounds (oil-repellent hydrophilic agents) represented by the formulas (1) to (4) may be used in a form of the porous medium. Thus, exceptional oil-water separation performance is obtained, and accordingly, such a use is preferable.

As a method of obtaining a porous medium, a generally-known method may be applied. Specifically, for example, a method in which a dissolving liquid or a dispersion liquid of the oil-repellent hydrophilic agent is dried by a spray-dry method is exemplified. Regarding particles obtained by the spray-dry method, a porous medium may be formed and a particle diameter may be controlled. In addition, the particles themselves may be applied as a filtering medium. Thus, the particles are particularly preferable.

When an aggregate of particulate porous media is manufactured, a binder such as a resin or glassiness is added to a dissolving liquid or a dispersion liquid of the oil-repellent hydrophilic agent, and thus a particulate porous medium is bound. Thus, physical strength of an aggregate of the porous media may be improved, or solubility to water may be controlled and reduced.

The above-described thermoplastic resin or thermosetting resin may be used as the resin. The above-described silane compound or water glass may be used as the glassiness. The amount of used binder for the oil-repellent hydrophilic agent is not particularly limited, and the binder may be appropriately added in a range which allows particles to be bound to each other. Typically, the mass composition ratio of the oil-repellent hydrophilic agent and the binder is preferably used in a range of a pair of 0.2 to 99.9 and 99.8 to 0.1, more preferably used in a range of a pair of 2 to 98 and 98 to 2, and further preferably used in a range of a pair of 10 to 90 and 90 to 10.

<Inorganic Compound>

As the filter medium in this embodiment, a medium in which a channel is formed by a base having hydrophilicity, and a composite of one or more of nitrogen-containing fluorine compounds represented by the formulas (1) to (4), and an inorganic compound having charges or an ionic group is fixed onto at least a portion of the surface of the channel may be provided.

As the inorganic compound having charges or an ionic group, specifically, for example, an inorganic particle, a clay mineral, a flocculant is exemplified.

The inorganic particle is not particularly limited as long as the inorganic particle has charges. Specifically, for example, fumed silica, colloidal silica, mullite, alumina, and zeolite are exemplified. As the inorganic particle, any of these substances may be singly used or be used as a mixture of two types or more.

The inorganic particle may be an aggregate of primary particles.

In a case where an inorganic particle is used as the inorganic compound, a composite in which at least a portion of the nitrogen-containing fluorine compound is combined with the surface of the inorganic particle by noncovalent bond is obtained.

The clay mineral is not particularly limited as long as the clay mineral has charges. Specifically, for example, bentonite, organic bentonite, smectite, and kaolinite are exemplified. As the clay mineral, any of these substances may be singly used or be used as a mixture of two types or more.

In a case where the clay mineral is used as the inorganic compound, a composite in which the nitrogen-containing fluorine compound is taken between layers of the clay mineral and thus the layers are combined is obtained.

The flocculant is not particularly limited as long as the flocculant has an ionic group. Specifically, for example, polyaluminium chloride, ferric polysulfate (polyferric sulfate), and aluminum sulfate are exemplified. As the flocculant, any of these substances may be singly used or be used as a mixture of two types or more. In addition, the flocculant may be dissolved in water, and may be used in a liquid phase. In a case where the flocculant is used as the inorganic compound, a composite in which at least a portion of the nitrogen-containing fluorine compound and the flocculant are combined by noncovalent bond is obtained.

In the oil-repellent hydrophilic agent in this embodiment, the mass composition ratio of the nitrogen-containing fluorine compound and the inorganic compound is not particularly limited, and may be appropriately selected in accordance with characteristic values of the hydrophilic and oil-repellent properties or persistence of the characteristics. Specifically, the mass composition ratio of the nitrogen-containing fluorine compound and the inorganic compound may be selected in a range of a pair of 1 to 99 and 99 to 1.

As the filter medium in this embodiment, a medium in which a channel is configured by a base having hydrophilicity, and a composite of one or more of nitrogen-containing fluorine compounds represented by the formulas (1) to (4), and a fluorine resin particle is fixed onto the surface of the channel may be provided.

The mass composition ratio of the nitrogen-containing fluorine compound and the fluorine resin particle is not particularly limited, and may be appropriately selected in accordance with characteristic values of the hydrophilic and oil-repellent properties or persistence of the characteristics. Specifically, the mass composition ratio of the nitrogen-containing fluorine compound and the fluorine resin particle may be selected in a range of a pair of 1 to 99 and 99 to 1.

A composite formed from one or more of nitrogen-containing fluorine compounds represented by the formulas (1) to (4), and the inorganic compound or the fluorine resin particle may be formed. The obtained composite may be fixed to a channel formed by the base which has hydrophilicity. Thus, it is possible to further improve persistence of various capabilities such as the oil-water separation function and the like.

The above-described organic binder or inorganic binder may be used for forming a composite of the nitrogen-containing fluorine compound, and the inorganic compound or the fluorine resin particle, and for fixing the composite to the channel.

As described above, according to the filter medium in this embodiment, one or two or more types of nitrogen-containing fluorine compounds in which an oil-repellent imparting group and a hydrophilicity imparting group are contained in a molecule is provided on at least a portion of the surface of the channel configured by the base. Thus, in a case where a liquid mixture of water and oil flows into the filter medium in this embodiment, water passes through the channel, but oil passing through the channel is not possible. Accordingly, the filter medium in this embodiment can be used as a separation membrane or a water treatment filter which allows separation into water and oil only by gravity, and has hydrophilic and oil-repellent properties.

In the filter medium of this embodiment, the hydrophilic and oil-repellent properties are applied to the surface of the channel formed by the base. Thus, adhering of an organic molecule, or soil and muds is difficult, and accordingly, exceptional anti-fouling properties are obtained. Attached dirt is easily removed by physical treatment of, for example, back pressure washing, and easy-washability is also exceptional.

In the filter medium in this embodiment, if the channel is formed by the base having hydrophilicity, the nitrogen-containing fluorine compound is sufficiently held in the channel. Thus, persistence of an effect of oil-water separation performance and the like is exceptional.

In a case where the filter medium in this embodiment contains only the nitrogen-containing fluorine compound represented by the formulas (1) to (4), it is possible to apply exceptional hydrophilic and oil-repellent properties while a perfluoroalkyl group having 8 or more carbon atoms which are continuously bonded to each other is not contained, and a chemical structure which does not have a concern of generating PFOS or PFOA which becomes a problem in a point of bioaccumulation or environmental adaptability is provided.

In the filter medium in this embodiment, a composite formed from one or more of nitrogen-containing fluorine compounds represented by the formulas (1) to (4), and the inorganic compound or the fluorine resin particle may be formed. The obtained composite may be fixed to a channel formed by the base which has hydrophilicity. Thus, it is possible to further improve persistence of various capabilities such as the oil-water separation function and the like.

The filter medium in this embodiment functions as an oil-water separating member which easily separates water and oil. That is, the nitrogen-containing fluorine compound in which an oil-repellency imparting group and a hydrophilicity imparting group are provided in a molecule is provided in the filter medium. Thus, if a liquid mixture of water and oil is brought into contact with the filter medium, moisture passes through the channel of the base. However, oil is excluded by the nitrogen-containing fluorine compound having oil repellent properties, and thus oil passing the base is not possible. Thus, the filter medium in this embodiment can separate water and oil only by putting an oil-water liquid mixture. The filter medium can perform separation into moisture and oil with low cost in a simple configuration. In addition, the filter medium can filter moisture and collect the oil.

<Method for Producing Filter Medium>

Next, a method for producing the above-described filter medium in this embodiment will be described by using a form in which a portion or the entirety of the surface of the above-described base is coated with a coating film containing the nitrogen-containing fluorine compound (oil-repellent hydrophilic agent) represented by the formulas (1) to (4), as an example.

Specifically, the method for producing a filter medium in this embodiment is schematically configured by including a process (first process), a process (second process), and a process (third process). In the process (first process), one type or two types or more of the nitrogen-containing fluorine compounds represented by the formulas (1) to (4) are dispersed or dissolved in water or an organic solvent. In the process (second process), the surface of the base is coated with a coating liquid in which the nitrogen-containing fluorine compound is dispersed or dissolved. In the process (third process), a dispersion medium or a solvent is removed by drying, and the coating film is formed on the surface of the base. The processes will be described below in detail.

(First Process)

Firstly, in the first process, one or more of the nitrogen-containing fluorine compound (oil-repellent hydrophilic agent) represented by the formulas (1) to (4) are caused to be contained in a solvent, and thus a surface coating material of the hydrophilic and oil-repellent agent may be formed. Here, as the solvent, water, an organic solvent, and a mixture of water and an organic solvent are exemplified. Examples of the organic solvent include methanol, ethanol, IPA, tetrahydrofuran, hexane, chloroform, toluene, ethyl acetate, DMSO, DMF, acetone, a fluorinated solvent. In particles, from a viewpoint of easy use by easy drying, an influence on an environment, and the like, water, alcohols such as methanol, ethanol, and IPA, or a mixture of water and alcohol is preferable. A solvent having compatibility with the above-described solvent may be mixed. For example, an ether solvent such as tetrahydrofuran, an aliphatic hydrocarbon solvent such as hexane, a halogenated hydrocarbon solvent such as chloroform, an aromatic hydrocarbon solvent such as toluene, an ester solvent such as ethyl acetate, a ketone solvent such as acetone, a fluorinated solvent such as hexafluoroxylene are exemplified.

In the surface coating material, the mass composition ratio of the oil-repellent hydrophilic agent and the solvent is preferably in a range of a pair of 0.2 to 50 and 99.8 to 50, more preferably in a range of a pair of 1.0 to 30.0 and 99.0 to 70.0, further preferably in a range of a pair of 1 to 20 and 99 to 80, and particularly preferably in a range of a pair of 2 to 10 and 98 to 90. If the mass composition ratio of the oil-repellent hydrophilic agent in the surface coating material is equal to or more than 0.2, the entirety of the base can be treated to be sufficiently hydrophilic and oil-repellent. Thus, this range is preferable. If the mass composition ratio of the oil-repellent hydrophilic agent in the surface coating material is equal to or less than 50, solvent dispersion stability of the surface coating material is exceptional. Thus, this range is preferable. If coating properties or durability of a product is added, the mass composition ratio between the oil-repellent hydrophilic agent and the solvent in a surface coating material is preferably in a range of a pair of 2 to 10 and 98 to 90.

The surface coating material has a function of enclosing the oil-repellent hydrophilic agent so as to reduce an area of the oil-repellent hydrophilic agent itself, in which the oil-repellent hydrophilic agent is in contact with an environment, in addition to improving adhesion to the base. In order to improve persistence or durability of characteristics, the above-described binder is preferably added.

A mixing method for forming the surface coating material is not particularly limited as long as the mixing method is a method in which the oil-repellent hydrophilic agent can be dispersed or dissolved in a solvent. The mixing method may be used by a ball mill, a roll mill, a sand mill, a paint shaker, a homogenizer, an impeller type stirrer, an ultrasonic disperser, a magnetic stirrer, and the like.

The surface coating material may contain an additive of a certain component, in addition to the oil-repellent hydrophilic agent, the solvent, and the binder. The additive may be contained in order to impart a function other than hydrophilicity and oil repellency, such as a pigment or a conductive imparting agent, and a leveling agent. An inorganic particle may be added to the surface coating material, and thus improving strength, durability, corrosion resistance, and hardness may be achieved.

(Second Process)

Then, in the second process, at least a portion of the surface of the base is coated with the prepared surface coating material. Here, a coating method of the surface of the base is not particularly limited. Specifically, for example, an immersion method of immersing the base in the surface coating material, and a method using coating means such as a spray, a brush, and a roller, or using a printing technique are exemplified.

(Third Process)

Then, in the third process, the dispersion medium or the solvent is removed by drying, and a coating film is formed on the surface of the base. Here, conditions for drying treatment for the coating film varies depending on the type or the content of a solvent contained in the surface coating material. For example, drying at room temperature for 1 to 24 hours or drying by heating as much as not influencing the base is exemplified.

As described above, according to the method for producing the filter medium in this embodiment, the surface of the base is coated with a coating liquid in which the above-described one or more of nitrogen-containing fluorine compounds are dispersed or dissolved in a solvent. Then, the dispersion medium or the solvent is removed by drying, and the coating film is formed on the surface of the base. Thus, it is possible to safely and simply manufacture the above-described filter medium. In a case where the base is a fiber assembly or an aggregate of particles, a coating film is formed in advance, on the surface of fibers or particles. Then, an assembly may be produced by using fibers or particles of which the coating film is formed on the surface.

<Water Treatment Module>

Next, a water treatment module according to this embodiment will be described. A water treatment module in this embodiment is not particularly limited as long as the module includes the above-described filter medium. Specifically, for example, a module in which an element (also referred to as a filter) formed by, for example, folding or bending the above-described film-like filter medium is stored in a pressure container and the like is exemplified. The water treatment module may be used as, for example, an oil-water separation filtration filter.

<Water Treatment Device>

Next, a water treatment device in this embodiment will be described. The water treatment device in this embodiment is not particularly limited as long as the device includes the above-described water treatment module. The water treatment device may be used as, for example, an oil-water separation device.

Specifically, for example, a method of a mass filtration type or a cross-flow type may be used as a filtration method of the water treatment device. As a filter base used in filtration, a membrane filter (fluororesin, cellulose acetate, polyester, and the like) or a hollow-fiber membrane may be used.

The shape of the filter medium may be appropriately selected in accordance with a separation system. For example, a sheet shape, a flat film type, a cartridge type, and a module type are exemplified.

In the cartridge type, an object obtained by winding a fiber so as to form a filter, or a filter using non-woven fabric, and the like are exemplified.

As a method in which filling with a particulate type filter medium (including a form of powder of the oil-repellent hydrophilic agent itself) is performed, and thus oil-water separation is performed, the filter medium (oil-water separation filter medium) in this embodiment, as a filtration assistant, is laid on the known separation filter as pretreatment of a liquid separation operation, and thus only water may be permeated without oil being not permeated.

As described above, since the water treatment module and the water treatment device in this embodiment includes the above-described filter medium, oil-water separation is possible. In addition, the antifouling properties, the easy washing properties, and the anti-fouling properties are exceptional.

In a case where a spillage accident of oil due to the malfunction of a facility, disaster, or the like occurs in factories or electric utilities of, for example, food manufacturing, fiber treatment, petroleum refining, and a heavy oil storage facility, an oil-water separation filtration filter which is an example of the water treatment module in this embodiment is laid on the floor or the ground or in a drainage ditch, in order to prevent leakage of oil to the outside of the site. Thus, the oil-water separation filtration filter may be used as an oil retaining wall for emergency, which blocks only oil from a liquid. The liquid is to be treated, contains oil, and, for example, is an oil-water liquid mixture in which water and oil is mixed. In a case where oil is spilled to a river, the sea, and the like, the oil-water separation filtration filter may be used as an oil fence for emergency which is used for preventing diffusion of oil.

In particular, in factories and the like which need drainage treatment, prevention of leaked oil put and mixed in a drainage path, from being spilled to the outside of the site is required. Thus, if the water treatment device (oil-water separation device) in the this embodiment which has a function as a water-passing oil-retaining wall which blocks only oil with maintaining passing of water is laid in the drainage path, it is possible to continuously operate, and to prevent diffusion of the leaked oil and collect the leaked oil. Thus, the water treatment device is useful for an emergency.

As capability required for an oil-water separation membrane (filter medium), permeation flux which is as large as possible, and continuous use for a long term are desirable. For example, as the permeation flux of the oil-water separating member, a member of 0.5 to 5 $m^3/hr \cdot m^2$ is generally used. In the oil-water separation membrane (filter medium) which is an embodiment of the present invention, a hydrophilic base is used as the base, and thus it is possible to continuously maintain water permeability of the oil-water separation membrane, and to maintain the permeation flux appropriate for continuous use for a long term.

The technical range of the present invention is not limited to the above embodiment. Various modifications may be made in a range without departing from the gist of the invention.

EXAMPLES

Advantages of the present invention will be described below in detail by using examples. The present invention is not limited to the examples.

[Synthesis of Nitrogen-Containing Fluorine Compound]

Synthetic Example 1

Synthesis of 2-[3-[[perfluoro(2-methyl-3-dibutylaminopropanoyl)]amino]propyl-dimethyl-ammonium] acetate 120 g of perfluoro(2-methyl-3-dibutylaminopropionic acid)fluoride obtained by electrolytic fluorination of 2-methyl-3-dibutyl amiopropionate methyl were dropped in a solution in which 39 g of dimethyl aminopropylamine were dissolved in 500 ml of an IPE solvent, in an ice bath. Stirring was performed at an room temperature for two hours, and then filtration was performed. An IPE layer in a filtrate was subjected to washing treatment by a NaHCO$_3$ aqueous solution and a NaCl aqueous solution. Liquid separation was performed, and then water washing was performed. Then, IPE was distilled, and thus 64 g of (C$_4$F$_9$)$_2$NCF$_2$CF(CF$_3$)CONHC$_3$H$_6$N(CH$_3$)$_2$ were obtained as a crude product (yield of 47%).

Then, 8 g of obtained (C$_4$F$_9$)$_2$NCF$_2$CF(CF$_3$)CONHC$_3$H$_6$N(CH$_3$)$_2$ flowed back along with sodium monochloroacetate for one night, with stirring in ethanol. Filtration and concentration was performed, and thus 9 g of a dimethyl betaine substance represented by the following formula (376) were obtained (yield of 99%).

[Chemical Formula 382]

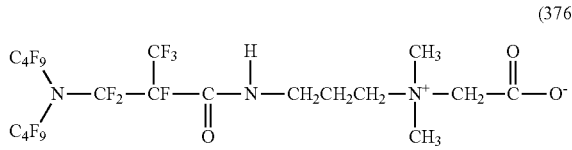

(376)

Synthetic Example 2

Synthesis of 2-[3-[[perfluoro(3-dibutylaminopropanoyl)]amino]propyl-dimethyl-ammonium]acetate 20 g of perfluoro(3-dibutyl aminopropionic acid)fluoride obtained by electrolytic fluorination of 3-dibutyl amiopropionate methyl were dropped in a solution in which 4 g of dimethyl aminopropylamine were dissolved in 50 ml of an IPE solvent, in an ice bath. Stirring was performed at room temperature for two hours, and then filtration was performed. An IPE layer in a filtrate was subjected to washing treatment by a NaHCO$_3$ aqueous solution and a NaCl aqueous solution. Liquid separation was performed, and then water washing was performed. Then, IPE was distilled, and thus 14 g of (C$_4$F$_9$)$_2$NC$_2$F$_4$CONHC$_3$H$_6$N(CH$_3$)$_2$ were obtained as a crude product (yield of 60%).

Then, 3 g of obtained (C$_4$F$_9$)$_2$NC$_2$F$_4$CONHC$_3$H$_6$N(CH$_3$)$_2$ flowed back along with sodium monochloroacetate for one night, with stirring in ethanol. Thus, 3 g of a dimethyl betaine substance represented by the following formula (377) were obtained (yield of 92%).

[Chemical Formula 383]

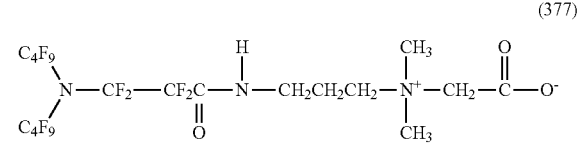

(377)

Synthetic Example 3

Synthesis of 2-[3-[[perfluoro(2-methyl-3-piperidinopropanoyl)]amino]propyl-dimethyl-ammonium]acetate 20 g of perfluoro(2-methyl-3-piperidinopropionic acid) fluoride obtained by electrolytic fluorination were dropped in a solution in which 9 g of dimethyl aminopropylamine were dissolved in 110 ml of an IPE solvent, in an ice bath. Stirring was performed at room temperature for two hours, and then filtration was performed. An IPE layer in a filtrate was subjected to washing treatment by a NaHCO$_3$ aqueous solution and a NaCl aqueous solution. Liquid separation was performed, and then water washing was performed. Then, IPE was distilled, and thus 18 g of CF$_2$(CF$_2$CF$_2$)$_2$NCF$_2$CF(CF$_3$)CONHC$_3$H$_6$N(CH$_3$)$_2$ were obtained as a crude product (crude yield of 76%).

Then, 10 g of the obtained crude product of CF$_2$(CF$_2$CF$_2$)$_2$NCF$_2$CF(CF$_3$)CONHC$_3$H$_6$N(CH$_3$)$_2$ flowed back along with 3 g of sodium monochloroacetate for one night, with stirring in ethanol. Thus, 11 g of a dimethyl betaine substance represented by the following formula (378) were obtained (yield of 99%).

[Chemical Formula 384]

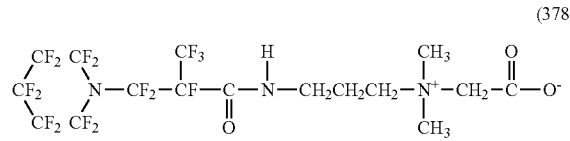

(378)

Synthetic Example 4

Synthesis of 2-[3-[[perfluoro(2-methyl-3-morpholinopropanoyl)]amino]propyl-dimethyl-ammonium]acetate 21 g of perfluoro(3-methyl-3-morpholinopropionic acid) fluoride obtained by electrolytic fluorination were dropped in a solution in which 10 g of dimethyl aminopropylamine were dissolved in 100 ml of an IPE solvent, in an ice bath. Then, stirring was performed at room temperature for two hours, and then filtration was performed. An IPE layer in a filtrate was subjected to washing treatment by a NaHCO$_3$ aqueous solution and a NaCl aqueous solution. Liquid separation was performed, and then water washing was performed. Then, IPE was distilled, and thus 22 g of O(CF$_2$CF$_2$)$_2$NCF$_2$CF(CF$_3$)CONHC$_3$H$_6$N(CH$_3$)$_2$ were obtained as a crude product (crude yield of 88%).

Then, 10 g of the obtained crude product of O(CF$_2$CF$_2$)$_2$NCF$_2$CF(CF$_3$)CONHC$_3$H$_6$N(CH$_3$)$_2$ flowed back along with 3 g of sodium monochloroacetate for one night, with stirring in ethanol. Thus, 11 g of a dimethyl betaine substance represented by the following formula (379) were obtained (yield of 99%).

[Chemical Formula 385]

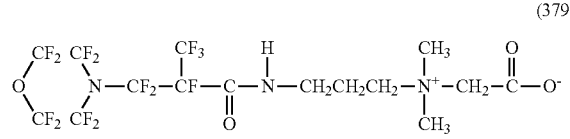

(379)

Synthetic Example 5

Synthesis of perfluoro(3-dibutylaminopropionic acid)calcium 352 g of a 12.5% sodium hydroxide aqueous solution were put into a 2 L glass flask, and 837 g of perfluoro(3- dibutylaminopropionic acid)fluoride obtained by electrolytic fluorination of methyl 3-dibutylaminopropionate were dropped so as to cause a reaction. After dropping, 500 mL of ethyl acetate were added, and then sodium perfluoro(3-dibutylaminopropionic acid) was extracted. After an ethyl acetate layer was separated from water, ethyl acetate was distilled in a rotary evaporator. 488 g of sodium perfluoro (3-dibutylaminopropionic acid) of a light-yellow solid body were obtained.

Then, 488 g of sodium perfluoro(3-dibutylaminopropionic acid) and 280 g of 95% sulfuric acid were put into a 1 L of glass flask, and were mixed. Reduced—pressure distillation was performed, and thus 436 g of perfluoro (3-dibutylaminopropionic acid) of a solid body were obtained at normal temperature (yield of 93% from a sodium salt).

23.5 g of obtained perfluoro (3-dibutylaminopropionic acid) were neutralized in a methanol/water liquid mixture by 1.5 g of calcium hydroxide. Crystals obtained by precipitation were separated by filtration. Drying was performed at 100° C., and thus 23.5 g of perfluoro(3-dibutylaminopropionic acid)calcium represented by the following formula (380) was obtained (yield of 97%). The solubility of the compound to water at room temperature was 0.02 mass %.

[Chemical Formula 386]

(380)

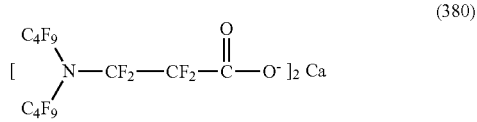

Synthetic Example 6

Synthesis of 3-[[perfluoro(3-dibutylaminopropanoyl)]amino]propyl-trimethyl-ammonium iodide 10 g of perfluoro(3-dibutyl aminopropionic acid)fluoride obtained by electrolytic fluorination of 3-dibutyl amiopropionate methyl were dropped in a solution in which 4 g of dimethyl aminopropylamine were dissolved in 50 ml of an IPE solvent, in an ice bath. Stirring was performed at room temperature for two hours, and then filtration was performed. An IPE layer in a filtrate was subjected to washing treatment by a NaHCO$_3$ aqueous solution and a NaCl aqueous solution. Liquid separation was performed, and then water washing was performed. Then, IPE was distilled, and thus 7 g of $(C_4F_9)_2NC_2F_4CONHC_3H_6N(CH_3)_2$ were obtained as a crude product (yield of 62%).

Then, methyl iodide in methyl ethyl ketone was added to the obtained crude product, and was stirred at room temperature for one night. After the reaction is ended, separate collection was performed, and thus 6 g of a quaternary ammonium iodide substance represented by the following formula (381) was obtained (yield of 71%).

[Chemical Formula 387]

(381)

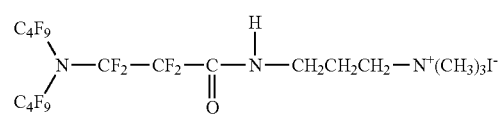

Synthetic Example 7

Synthesis of 3-[3-[[perfluoro(2-methyl-3-dibutylaminopropanoyl)]amino]propyl-dimethyl-ammonium] propanesulfonate 120 g of perfluoro(2-methyl-3-dibutylaminopropionic acid)fluoride obtained by electrolytic fluorination of 2-methyl-3-dibutyl amiopropionate methyl were dropped in a solution in which 39 g of dimethyl aminopropylamine were dissolved in 500 ml of an IPE solvent, in an ice bath. Stirring was performed at room temperature for two hours, and then filtration was performed. An IPE layer in a filtrate was subjected to washing treatment by a NaHCO$_3$ aqueous solution and a NaCl aqueous solution. Liquid separation was performed, and then water washing was performed. Then, IPE was distilled, and thus 64 g of $(C_4F_9)_2NCF_2CF(CF_3)$ CONHC$_3$H$_6$N(CH$_3$)$_2$ were obtained as a crude product (yield of 47%).

Then, 1.5 g of obtained $(C_4F_9)_2NCF_2CF(CF_3)$ CONHC$_3$H$_6$N(CH$_3$)$_2$ flowed back along with 1,3-propane sultone for 23 hours, with stirring in acetonitrile. Then, reprecipitation in a fluorinated solvent AK225 and an IPE solvent mixture was performed, and thus 1.3 g of a sulfobetaine substance represented by the following formula (382) were obtained (yield of 75%).

[Chemical Formula 388]

(382)

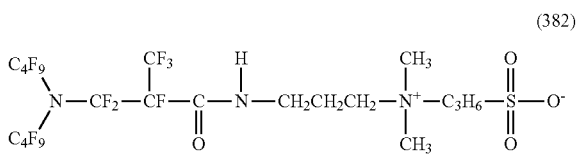

Synthetic Example 8

Synthesis of [3-[[perfluoro(2-methyl-3-morpholinopropanoyl)]amino]propyl-dimethyl-ammonium]oxide 21 g of perfluoro(2-methyl-3-morpholinopropionic acid) fluoride obtained by electrolytic fluorination of 2-methyl-3-morpholinopropionate methyl was dropped in a solution in which 10 g of dimethyl aminopropylamine was dissolved in 100 ml of an IPE solvent, in an ice bath. Then, stirring was performed at room temperature for two hours, and then filtration was performed. An IPE layer in a filtrate was subjected to washing treatment by a NaHCO$_3$ aqueous solution and a NaCl aqueous solution. Liquid separation was performed, and then water washing was performed. Then, IPE was distilled, and thus 22 g of O(CF$_2$CF$_2$)$_2$NCF$_2$CF (CF$_3$)CONHC$_3$H$_6$N(CH$_3$)$_2$ were obtained as a crude product (crude yield of 88%).

Then, 5 g of obtained O(CF$_2$CF$_2$)$_2$NCF$_2$CF(CF$_3$) CONHC$_3$H$_6$N(CH$_3$)$_2$ was caused to react with hydrogen peroxide water at 70° C. in ethanol for two hours, with stirring. Then, filtration and concentration was performed, and thus 2 g of an amine oxide substance represented by the following formula (383) was obtained (yield of 39%).

[Chemical Formula 389]

(383)

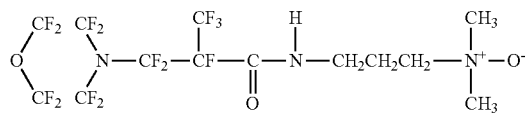

Synthetic Example 9

Synthesis of 2-[3-[[perfluoro(3-morpholinopropyl-sulfonyl)]amino]propyl-dimethyl-ammonium]acetate 4 g of perfluoro-(N-morpholinopropanesulfonyl)fluoride obtained by electrolytic fluorination of N-morpholinopropanesulfonyl chloride was dropped in a solution in which 2 g of dimethyl aminopropylamine was dissolved in 20 ml of an IPE solvent, in an ice bath. Stirring was performed at room temperature for two hours, and then filtration was performed. An IPE layer in a filtrate was subjected to washing treatment by a $NaHCO_3$ aqueous solution and a NaCl aqueous solution. Liquid separation was performed, and then water washing was performed. Then, IPE was distilled, and thus 2.1 g of $O(C_2F_4)_2NC_3F_6SO_2NHC_3H_6N(CH_3)_2$ were obtained as a crude product (yield of 45%).

Then, 1 g of obtained $O(C_2F_4)_2NC_3F_6SO_2NHC_3H_6N(CH_3)_2$ flowed back along with sodium monochloroacetate for one night, with stirring in ethanol. Filtration and concentration was performed, and thus 1.1 g of a dimethyl betaine substance represented by the following formula (384) were obtained (yield of 99%).

[Chemical Formula 390]

(384)

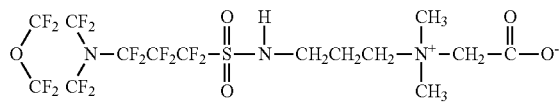

Synthetic Example 10

Synthesis of 2-[3-[[perfluoro(2-methyl-3-(4-methyl-1-piperazyl)propanoyl)]amino]propyl-dimethyl-ammonium]acetate 20 g of perfluoro(2-methyl-3-(4-methyl-1-piperazyl)propionic acid)fluoride obtained by electrolytic fluorination of 2-methyl-3-(4-methyl-1-piperazyl)methyl propionate was dropped in a solution in which 8.5 g of dimethyl aminopropylamine was dissolved in 100 ml of an IPE solvent, in an ice bath. Then, stirring was performed at room temperature for two hours, and then filtration was performed. An IPE layer in a filtrate was subjected to washing treatment by a $NaHCO_3$ aqueous solution and a NaCl aqueous solution. Liquid separation was performed, and then water washing was performed. Then, IPE was distilled, and thus 19.8 g of $CF_3N(CF_2CF_2)_2NCF_2CF(CF_3)CONHC_3H_6N(CH_3)_2$ were obtained as a crude product (crude yield of 85%).

Then, 10 g of the obtained crude product of $CF_3N(CF_2CF_2)_2NCF_2CF(CF_3)CONHC_3H_6N(CH_3)_2$ flowed back along with 3 g of sodium monochloroacetate for one night, with stirring in ethanol. Thus, 10.9 g of a dimethyl betaine substance represented by the following formula (385) were obtained (yield of 99%).

[Chemical Formula 391]

(385)

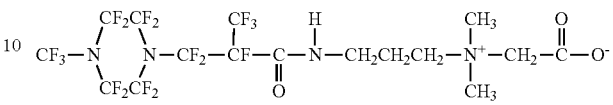

Synthetic Example 11

Synthesis of 2-[3-[[perfluoro(pyrrolidinoacetyl)]amino] propyl-dimethyl-ammonium]acetate 15 g of perfluoro(pyrrolidinoacetyl fluoride) obtained by electrolytic fluorination of N-(2-hydroxyethyl)pyrrolidine were dropped in a solution in which 10 g of dimethyl aminopropylamine were dissolved in 100 ml of an IPE solvent, in an ice bath. Then, stirring was performed at room temperature for two hours, and then filtration was performed. An IPE layer in a filtrate was subjected to washing treatment by a $NaHCO_3$ aqueous solution and a NaCl aqueous solution. Liquid separation was performed, and then water washing was performed. Then, IPE was distilled, and thus 14.2 g of $(CF_2CF_2)_2NCF_2CONHC_3H_6N(CH_3)_2$ were obtained as a crude product (crude yield of 75%).

Then, 10 g of the obtained crude product of $(CF_2CF_2)_2NCF_2CONHC_3H_6N(CH_3)_2$ flowed back along with 4 g of sodium monochloroacetate for one night, with stirring in ethanol. Thus, 11.4 g of a dimethyl betaine substance represented by the following formula (386) were obtained (yield of 99%).

[Chemical Formula 392]

(386)

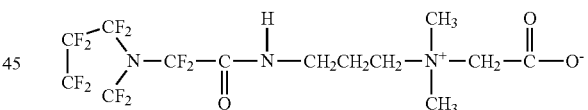

Synthetic Example 12

Synthesis of 3-[[perfluoro(2-dimethylaminoethylsulfonyl)]amino]propyl-trimethyl-ammonium iodide Perfluoro(3-dimethylamino)propionyl fluoride obtained by electrolytic fluorination of 3-dimethylaminopropionate methyl derives perfluoro[2-(dimethylamino)ethanesulfonic acid fluoride by a method described in Japanese Patent No. 4406700. 40 g of perfluoro[2-(dimethylamino)ethanesulfonic acid fluoride were dropped in a solution in which 25.0 g of dimethyl aminopropylamine were dissolved in 250 ml of an IPE solvent, in an ice bath. Stirring was performed at room temperature for two hours, and then filtration was performed. An IPE layer in a filtrate was subjected to washing treatment by a $NaHCO_3$ aqueous solution and a NaCl aqueous solution. Liquid separation was performed, and then water washing was performed. Then, IPE was distilled, and thus 19.9 g of $(CF_3)_2NCF_2CF_2SO_2NHC_3H_6N(CH_3)_2$ were obtained as a crude product (yield of 45%).

Then, methyl iodide in methyl ethyl ketone was added to 8 g of the obtained crude product, and was stirred at room temperature for one night. After the reaction is ended, separate collection was performed, and thus 6.4 g of a quaternary ammonium iodide substance represented by the following formula (387) was obtained (yield of 60%).

[Chemical Formula 393]

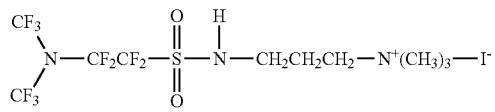

(387)

Synthetic Example 13

Synthesis of 2-[3-[[perfluoro(2-diethylaminoethyl-sulfonyl)]amino]propyl-dimethyl-ammonium]acetate Perfluoro(3-diethylamino)propionyl fluoride obtained by electrolytic fluorination of 3-diethylaminopropionate methyl derives perfluoro[2-(diethylamino)ethanesulfonic acid fluoride by a method described in Japanese Patent No. 4406700. 50 g of perfluoro[2-(diethylamino)ethanesulfonic acid fluoride were dropped in a solution in which 24.1 g of dimethyl aminopropylamine were dissolved in 250 ml of an IPE solvent, in an ice bath. Stirring was performed at room temperature for two hours, and then filtration was performed. An IPE layer in a filtrate was subjected to washing treatment by a $NaHCO_3$ aqueous solution and a NaCl aqueous solution. Liquid separation was performed, and then water washing was performed. Then, IPE was distilled, and thus 29.4 g of $(C_2F_5)_2NCF_2CF_2SO_2NHC_3H_6N(CH_3)_2$ were obtained as a crude product (yield of 50%).

Then, 10 g of obtained $(C_2F_5)_2NCF_2CF_2SO_2NHC_3H_6N(CH_3)_2$ flowed back along with sodium monochloroacetate for one night, with stirring in ethanol. Filtration and concentration was performed, and thus 11 g of a dimethyl betaine substance represented by the following formula (388) were obtained (yield of 99%).

[Chemical Formula 394]

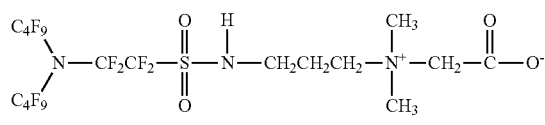

(388)

Synthetic Example 14

Synthesis of 2-[3-[perfluoro(3-dibutylaminopropanoyl)]oxypropyl-dimethyl-ammonium]acetate 20 g of perfluoro(3-dibutyl aminopropionic acid)fluoride obtained by electrolytic fluorination of 3-dibutyl amiopropionate methyl were dropped in a solution in which 4 g of N,N-dimethylpropanolamine were dissolved in 50 ml of an IPE solvent, in an ice bath. Stirring was performed at room temperature for two hours, and then filtration was performed. An IPE layer in a filtrate was subjected to washing treatment by a $NaHCO_3$ aqueous solution and a NaCl aqueous solution. Liquid separation was performed, and then water washing was performed. Then, IPE was distilled, and thus 11.4 g of $(C_4F_9)_2NC_2F_4COOC_3H_6N(CH_3)_2$ were obtained as a crude product (yield of 50%).

Then, 3 g of obtained $(C_4F_9)_2NC_2F_4COOC_3H_6N(CH_3)_2$ flowed back along with sodium monochloroacetate for one night, with stirring in ethanol. Thus, 3 g of a dimethyl betaine substance represented by the following formula (389) were obtained (yield of 93%).

[Chemical Formula 395]

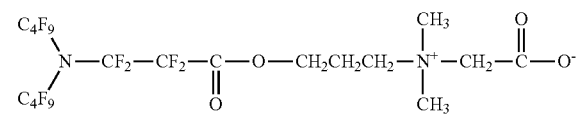

(389)

Synthetic Example 15

Synthesis of 2-[3-[[perfluoro(2-methyl-3-dihexylaminopropanoyl)]amino]propyl-dimethyl-ammonium]acetate 20 g of perfluoro(2-methyl-3-dihexylaminopropionic acid)fluoride obtained by electrolytic fluorination of 2-methyl-3-dihexylaminopropionate methyl were dropped in a solution in which 5 g of dimethyl aminopropylamine were dissolved in 50 ml of an IPE solvent, in an ice bath. Stirring was performed at room temperature for two hours, and then filtration was performed. An IPE layer in a filtrate was subjected to washing treatment by a $NaHCO_3$ aqueous solution and a NaCl aqueous solution. Liquid separation was performed, and then water washing was performed. Then, IPE was distilled, and thus 7.7 g of $(C_6F_{13})_2NCF_2CF(CF_3)CONHC_3H_6N(CH_3)_2$ were obtained as a crude product (yield of 35%).

Then, 5 g of obtained $(C_6F_{13})_2NCF_2CF(CF_3)CONHC_3H_6N(CH_3)_2$ flowed back along with sodium monochloroacetate for one night, with stirring in ethanol. Filtration and concentration was performed, and thus 5.2 g of a dimethyl betaine substance represented by the following formula (390) were obtained (yield of 97%).

[Chemical Formula 396]

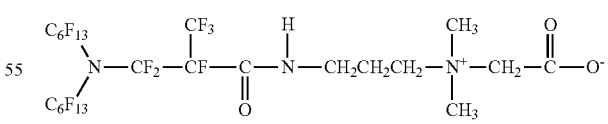

(390)

Synthetic Example 16

Synthesis of 4-[3-[[perfluoro(2-methyl-3-dibutylaminopropanoyl)]amino]propyl-dimethyl-ammonium butanesulfonate 120 g of perfluoro(2-methyl-3-dibutylaminopropionic acid)fluoride obtained by electrolytic fluorination of 2-methyl-3-dibutyl amiopropionate methyl were dropped in a solution in which 39 g of dimethyl aminopropylamine were dissolved in 500 ml of an IPE solvent, in an ice bath. Stirring was performed at room temperature for two hours, and then filtration was performed. An IPE layer in a filtrate was subjected to washing treatment by a NaHCO$_3$ aqueous solution and a NaCl aqueous solution. Liquid separation was performed, and then water washing was performed. Then, IPE was distilled, and thus 64 g of (C$_4$F$_9$)$_2$NCF$_2$CF(CF$_3$)CONHC$_3$H$_6$N(CH$_3$)$_2$ were obtained as a crude product (yield of 47%).

Then, 15 g of obtained (C$_4$F$_9$)$_2$NCF$_2$CF(CF$_3$)CONHC$_3$H$_6$N(CH$_3$)$_2$ flowed back along with 4.2 g of 1,4-butanesultone for 18 hours, with stirring in acetonitrile. Then, reprecipitation in a fluorinated solvent AK225 and an IPE solvent mixture was performed, and thus 13.3 g of a sulfobetaine substance represented by the following formula (391) were obtained (yield of 75%).

[Chemical Formula 397]

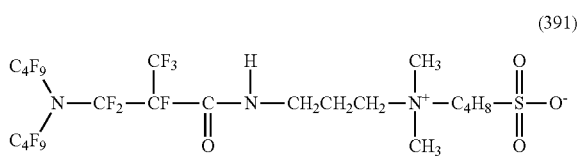

(391)

Synthetic Example 17

Synthesis of 3-[3-[[perfluoro(2-methyl-3-dibutylaminopropanoyl)]amino]propyl-dimethyl-ammonium] 2-hydroxypropane-1-sulfonate 120 g of perfluoro(2-methyl-3-dibutylaminopropionic acid)fluoride obtained by electrolytic fluorination of 2-methyl-3-dibutyl amiopropionate methyl were dropped in a solution in which 39 g of dimethyl aminopropylamine were dissolved in 500 ml of an IPE solvent, in an ice bath. Stirring was performed at room temperature for two hours, and then filtration was performed. An IPE layer in a filtrate was subjected to washing treatment by a NaHCO$_3$ aqueous solution and a NaCl aqueous solution. Liquid separation was performed, and then water washing was performed. Then, IPE was distilled, and thus 64 g of (C$_4$F$_9$)$_2$NCF$_2$CF(CF$_3$)CONHC$_3$H$_6$N(CH$_3$)$_2$ were obtained as a crude product (yield of 47%).

Then, 5.0 g of obtained (C$_4$F$_9$)$_2$NCF$_2$CF(CF$_3$)CONHC$_3$H$_6$N(CH$_3$)$_2$ was mixed with 2.0 g of 3-chloro-2-hydroxypropane sulfonate sodium, 10 ml of ethanol, and 2.1 g of water, and flowed back for 20 hours. Then, 0.7 g of sodium carbonate was added, and flowed back for four hours. After the reaction is ended, a reaction liquid was put into water. Then, precipitated solid is caused to be reprecipitated in a fluorinated solvent AK225 and an IPE mixture solvent. Thus, 3.5 g of a sulfobetaine substance represented by the following formula (392) were obtained (yield of 59%).

[Chemical Formula 398]

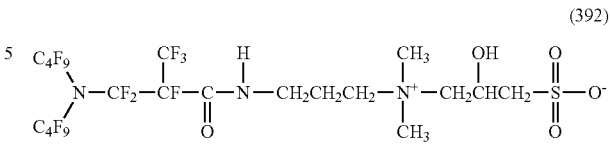

(392)

Synthetic Example 18

Synthesis of 3-[[perfluoro(2-methyl-3-dibutylaminopropanoyl)]amino]propyl-trimethyl-ammonium iodide 120 g of perfluoro(2-methyl-3-dibutylaminopropionic acid)fluoride obtained by electrolytic fluorination of 2-methyl-3-dibutyl amiopropionate methyl were dropped in a solution in which 39 g of dimethyl aminopropylamine were dissolved in 500 ml of an IPE solvent, in an ice bath. Stirring was performed at room temperature for two hours, and then filtration was performed. An IPE layer in a filtrate was subjected to washing treatment by a NaHCO$_3$ aqueous solution and a NaCl aqueous solution. Liquid separation was performed, and then water washing was performed. Then, IPE was distilled, and thus 64 g of (C$_4$F$_9$)$_2$NCF$_2$CF(CF$_3$)CONHC$_3$H$_6$N(CH$_3$)$_2$ were obtained as a crude product (yield of 47%).

Then, methyl iodide in methyl ethyl ketone was added to the obtained crude product, and was stirred at room temperature for one night. After the reaction is ended, separate collection was performed, and thus 6 g of a quaternary ammonium iodide substance represented by the following formula (393) was obtained (yield of 71%).

[Chemical Formula 399]

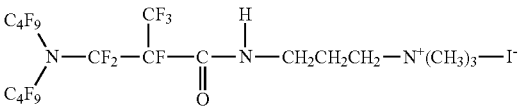

(393)

Synthetic Example 19

Synthesis of 3-[3-[[perfluoro(2-methyl-3-morpholinopropanoyl)]amino]propyl-dimethyl-ammonium]propanesulfonate 21 g of perfluoro(3-methyl-3-morpholinopropionic acid) fluoride obtained by electrolytic fluorination of 2-methyl-3-morpholinopropionate methyl was dropped in a solution in which 10 g of dimethyl aminopropylamine was dissolved in 100 ml of an IPE solvent, in an ice bath. Then, stirring was performed at room temperature for two hours, and then filtration was performed. An IPE layer in a filtrate was subjected to washing treatment by a NaHCO$_3$ aqueous solution and a NaCl aqueous solution. Liquid separation was performed, and then water washing was performed. Then, IPE was distilled, and thus 22 g of O(CF$_2$CF$_2$)$_2$NCF$_2$CF(CF$_3$)CONHC$_3$H$_6$N(CH$_3$)$_2$ were obtained as a crude product (crude yield of 88%).

Then, 2 g of obtained O(CF$_2$CF$_2$)$_2$NCF$_2$CF(CF$_3$)CONHC$_3$H$_6$N(CH$_3$)$_2$ flowed back along with 1,3-propane sultone for one night, with stirring in methylene chloride. Then, reprecipitation in a fluorinated solvent AK225 and an IPE mixture solvent was performed, and thus 2.2 g of a sulfobetaine substance represented by the following formula (394) were obtained (yield of 98%).

[Chemical Formula 400]

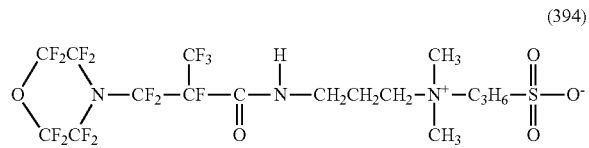

(394)

Example A (Base)

A commercial PTFE membrane filter having a diameter of 47 mm (ADVANTEC T100A047A: hole diameter of 1 μm, porosity of 79%, thickness of 75 μm), polypropylene nonwoven fabric having basis weight of 72 g/m², and a thickness of 0.26 mm, and polyethylene/polypropylene composite nonwoven fabric having a basis weight of 60 g/m² and a thickness of 0.40 mm were cut off so as to have a circular filter shape having a diameter of 47 mm, and resultants of the cutoff were used as the base.

(Binder)

As a binder, polyvinyl butyral (S-LEC B BL-1, S-LEC B BL-S, S-LEC B BM-2, S-LEC K KS-10 manufactured by SEKISUI CHEMICAL CO., LTD.), acrylic resin (ARUFON UC-3000 manufactured by TOAGOSEI CO., LTD.), and terpene phenolic resin (YS POLYSTER N125 manufactured by YASUHARA CHEMICAL CO., LTD.) are used.

<Manufacturing of Filter Medium>

Firstly, an oil-repellent hydrophilic agent, a binder, and methanol or ethanol which is a solvent were mixed to each other at predetermined proportions, thereby a surface coating material was manufactured.

Then, the base was dipped into the surface coating material so as to sufficiently impregnating the solution. The base was brought back, and then natural drying was performed. Thus, the solvent was removed. In this manner, a permeation test filter (filter medium) was manufactured.

<Evaluation by Filter Permeation Test>

Water and n-hexadecane each was dropped in the produced permeation test filter. Permeability was visually determined based on the following definitions, and thus the hydrophilic and oil-repellent properties were evaluated.

For a dropping method of water and n-hexadecane, the following conditions were used.

Dropped quantity: (40 to 45) μL/droplet (water)
Dropped quantity: (20 to 25) μL/droplet (n-hexadecane)
Dropping height: 5 cm from the surface of filter
Dropping tool: polyfiller
Measurement temperature: room temperature (22±1° C.)

In the filter permeation test, the definitions of evaluation results are as follows.

A: permeation occurs within 30 seconds after liquid droplets are dropped in the permeation test filter B: permeation occurs for a period which is longer than 30 seconds and within five minutes after liquid droplets are dropped C: permeation does not occur for 30 minutes after liquid droplets are dropped <Evaluation of Durability by Ultrasonic Washing>

The permeation test filter was immersed in 50 ml of pure water, and ultrasonic washing was performed at room temperature by using an ultrasonic washer USK-5R (240 W, 40 kHz) manufactured by AS ONE corporation.

Replacement with pure water was performed for each of 90 minutes during a period from ultrasonic wave irradiation start to six hours, and was performed for each of 60 minutes during a period after six hours.

After ultrasonic wave irradiation for three hours, after ultrasonic wave irradiation for six hours, and after ultrasonic wave irradiation for eight hours, the filter was extracted, and the hydrophilic and oil-repellent properties were evaluated by a method similar to that for the filter permeation test.

Example A1

2 mass % of a nitrogen-containing fluorine compound synthesized as an oil-repellent hydrophilic agent in Synthetic Example 1, and 4 mass % of S-LEC B BL-S as a binder were mixed and dissolved in 94 mass % of methanol as a solvent, at the above proportions, thereby a surface coating material was manufactured.

Then, polypropylene nonwoven fabric having a basis weight of 72 g/m² and a thickness of 0.26 mm was used as a base, and the base was coated with the manufactured surface coating material by using the above-described method. Thus, a permeation test filter in Example A1 was manufactured. The following Table 1 shows manufacturing conditions. "The surface coating material adhering amount (solid)" in Table 1 corresponds to the amount of solid of the surface coating material adhering to the base.

Water and n-hexadecane each was dropped in the permeation test filter in Example A1, and initial performance and permeability after ultrasonic washing was evaluated. The following Table 2 shows evaluation results.

Example A2

A permeation test filter in Example A2 was manufactured similarly to that in Example A1 except that S-LEC B BL-1 was used as the binder, and ethanol was used as the solvent. Then, initial performance and permeability after ultrasonic washing was evaluated by using a method similar to that in Example A1. The following Table 1 shows manufacturing conditions. The following Table 2 shows evaluation results.

Example A3

2 mass % of a nitrogen-containing fluorine compound synthesized as an oil-repellent hydrophilic agent in Synthetic Example 1, and 20 mass % of S-LEC B BL-1 as a binder were mixed and dissolved in 78 mass % of ethanol, at the above proportions, thereby a surface coating material was manufactured.

Then, in a manner similar to that in Example A1, a permeation test filter in Example A3 was manufactured. Then, initial performance and permeability after ultrasonic washing was evaluated by using a method similar to that in Example A1. The following Table 1 shows manufacturing conditions. The following Table 2 shows evaluation results.

Example A4

A permeation test filter in Example A4 was manufactured similarly to that in Example A1 except that S-LEC B BM-2 was used as the binder. Then, initial performance and permeability after ultrasonic washing was evaluated by using a method similar to that in Example A1. The following Table 1 shows manufacturing conditions. The following Table 2 shows evaluation results.

Example A5

A permeation test filter in Example A5 was manufactured similarly to that in Example A1 except that S-LEC K KS-10 was used as the binder. Then, initial performance and permeability after ultrasonic washing was evaluated by using a method similar to that in Example A1. The following Table 1 shows manufacturing conditions. The following Table 2 shows evaluation results.

Example A6

A permeation test filter in Example A6 was manufactured similarly to that in Example A1 except that ARUFON UC-3000 was used as the binder, and ethanol was used as the solvent. Then, initial performance and permeability after ultrasonic washing was evaluated by using a method similar to that in Example A1. The following Table 1 shows manufacturing conditions. The following Table 2 shows evaluation results.

Example A7

A permeation test filter in Example A7 was manufactured similarly to that in Example A1 except that YS POLYSTER N125 was used as the binder, and ethanol was used as the solvent. Then, initial performance and permeability after ultrasonic washing was evaluated by using a method similar to that in Example A1. The following Table 1 shows manufacturing conditions. The following Table 2 shows evaluation results.

Example A8

2 mass % of a nitrogen-containing fluorine compound synthesized as an oil-repellent hydrophilic agent in Synthetic Example 1, and 4 mass % of S-LEC B BL-1 as a binder were mixed and dissolved in 94 mass % of methanol as a solvent, at the above proportions, thereby a surface coating material was manufactured.

Then, polyethylene/polypropylene composite nonwoven fabric having a basis weight of 60 g/m² and a thickness of 0.40 mm was used as a base, and the base was coated with the manufactured surface coating material by using the above-described method. Thus, a permeation test filter in Example A8 was manufactured, and then initial performance and permeability after ultrasonic washing was evaluated by using a method similar to that in Example A1. The following Table 1 shows manufacturing conditions. The following Table 2 shows evaluation results.

Example A9

2 mass % of a nitrogen-containing fluorine compound synthesized as an oil-repellent hydrophilic agent in Synthetic Example 2, and 4 mass % of S-LEC B BL-1 as a binder were mixed and dissolved in 94 mass % of methanol as a solvent, at the above proportions, thereby a surface coating material was manufactured.

Then, polypropylene nonwoven fabric having a basis weight of 72 g/m² and a thickness of 0.26 mm was used as a base, and the base was coated with the manufactured surface coating material by using the above-described method. Thus, a permeation test filter in Example A9 was manufactured, and then initial performance and permeability after ultrasonic washing was evaluated by using a method similar to that in Example A1. The following Table 1 shows manufacturing conditions. The following Table 2 shows evaluation results.

Example A10

A permeation test filter in Example A10 was manufactured in a manner similar to that in Example A9 except that a nitrogen-containing fluorine compound synthesized in Synthetic Example 3 was used as an oil-repellent hydrophilic agent. Then, initial performance and permeability after ultrasonic washing was evaluated by using a method similar to that in Example A1. The following Table 1 shows manufacturing conditions. The following Table 2 shows evaluation results.

Example A11

A permeation test filter in Example A11 was manufactured in a manner similar to that in Example A9 except that a nitrogen-containing fluorine compound synthesized in Synthetic Example 4 was used as an oil-repellent hydrophilic agent. Then, initial performance and permeability after ultrasonic washing was evaluated by using a method similar to that in Example A1. The following Table 1 shows manufacturing conditions. The following Table 2 shows evaluation results.

Example A12

A permeation test filter in Example A12 was manufactured in a manner similar to that in Example A9 except that a nitrogen-containing fluorine compound synthesized in Synthetic Example 5 was used as an oil-repellent hydrophilic agent. Then, initial performance and permeability after ultrasonic washing was evaluated by using a method similar to that in Example A1. The following Table 1 shows manufacturing conditions. The following Table 2 shows evaluation results.

Example A13

2 mass % of a nitrogen-containing fluorine compound synthesized as an oil-repellent hydrophilic agent in Synthetic Example 6 were mixed and dissolved in 98 mass % of methanol as a solvent, at the above proportions, thereby a surface coating material was manufactured.

Then, a commercial PTFE membrane filter having a diameter of 47 mm (ADVANTEC T100A047A: hole diameter of 1 μm, porosity of 79%, thickness of 75 μm) was used as the base. The base was coated with the manufactured surface coating material by using the above-described method. Thus, a permeation test filter in Example A13 was manufactured. Then, initial performance and permeability after ultrasonic washing was evaluated by using a method similar to that in Example A1. The following Table 1 shows manufacturing conditions. The following Table 2 shows evaluation results.

Comparative Example A1

As represented by the following formula (395), a compound which has a straight-chain nitrogen-containing perfluoroalkyl group in a molecule, and a polyoxyalkylene group as a hydrophilic group was dissolved in methanol, thereby 2.0 mass % of a methanol solution was manufactured. The manufactured methanol solution was set as a surface coating material of Comparative Example A1. Polypropylene nonwoven fabric having a basis weight of 72 g/m² and a thickness of 0.26 mm was coated with the surface coating material, thereby a permeation test filter in Comparative Example A1 was manufactured. Then, initial performance and permeability after ultrasonic washing was evaluated by using a method similar to that in Example A1. The following Table 1 shows manufacturing conditions. The following Table 2 shows evaluation results.

[Chemical Formula 401]

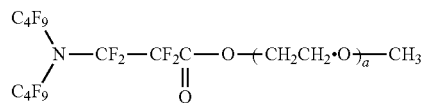
(395)

Comparative Example A2

As represented by the following formula (396), a compound which has a cyclic nitrogen-containing perfluoroalkyl group in a molecule, and a polyoxyalkylene group as a hydrophilic group was dissolved in methanol, thereby 2.0 mass % of a methanol solution was manufactured. The manufactured methanol solution was set as a surface coating material of Comparative Example A2. Polypropylene nonwoven fabric having a basis weight of 72 g/m² and a thickness of 0.26 mm was coated with the surface coating material, thereby a permeation test filter in Comparative Example A2 was manufactured. Then, initial performance and permeability after ultrasonic washing was evaluated by using a method similar to that in Example A1. The following Table 1 shows manufacturing conditions. The following Table 2 shows evaluation results.

[Chemical Formula 402]

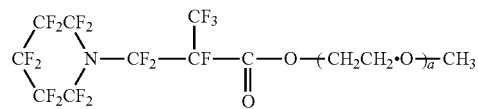
(396)

Comparative Example A3

A solution in which 98 mass % of methanol as a solvent were added and dissolved in 2 mass % of commercial calcium perfluorohexanoate represented by the following formula (397) was set as a surface coating material in Comparative Example A3.

Then, a commercial PTFE membrane filter having a diameter of 47 mm (ADVANTEC T100A047A: hole diameter of 1 μm, porosity of 79%, thickness of 75 μm) was used as the base. The base was coated with the manufactured surface coating material by using the above-described method. Thus, a permeation test filter in Comparative Example A3 was manufactured. Then, initial performance and permeability after ultrasonic washing was evaluated by using a method similar to that in Example A1. The following Table 1 shows manufacturing conditions. The following Table 2 shows evaluation results.

[Chemical Formula 403]

(397)

TABLE 1A

| | Surface coating material | | | | | Basis weight [g/m²] | Thickness [mm] | Surface coating material adhering amount (solid) [g/m²] |
| | Nitrogen-containing fluorine compound | | Binder | Solvent | | | | |
| | | [mass %] | [mass %] | [mass %] | Base | | | |
|---|---|---|---|---|---|---|---|---|
| Example A1 | Synthetic Example 1 | 2 | BL-S 4 | Methanol 94 | Polypropylene nonwoven fabric | 72 | 0.26 | 10.7 |
| Example A2 | | 2 | BL-1 4 | Ethanol 94 | Polypropylene nonwoven fabric | 72 | 0.26 | 9.2 |
| Example A3 | | 2 | BL-1 20 | Ethanol 78 | Polypropylene nonwoven fabric | 72 | 0.26 | 51.6 |
| Example A4 | | 2 | BM-2 4 | Methanol 94 | Polypropylene nonwoven fabric | 72 | 0.26 | 8.4 |
| Example A5 | | 2 | KS-10 4 | Methanol 94 | Polypropylene nonwoven fabric | 72 | 0.26 | 10.2 |
| Example A6 | | 2 | UC-3000 4 | Ethanol 94 | Polypropylene nonwoven fabric | 72 | 0.26 | 8.5 |
| Example A7 | | 2 | N125 4 | Ethanol 94 | Polypropylene nonwoven fabric | 72 | 0.26 | 8.8 |
| Example A8 | | 2 | BL-1 4 | Methanol 94 | Composite nonwoven fabric of polyethylene/polypropylene | 60 | 0.40 | 8.6 |
| Example A9 | Synthetic Example 2 | 2 | BL-1 4 | Methanol 94 | Polypropylene nonwoven fabric | 72 | 0.26 | 10.2 |
| Example A10 | Synthetic Example 3 | 2 | BL-1 4 | Methanol 94 | Polypropylene nonwoven fabric | 72 | 0.26 | 14.0 |

TABLE 1B

| | Surface coating material | | | | Basis weight [g/m²] | Thickness [mm] | Surface coating material adhering amount (solid) [g/m²] |
|---|---|---|---|---|---|---|---|
| | Nitrogen-containing fluorine compound [mass %] | Binder [mass %] | Solvent [mass %] | Base | | | |
| Example A11 | Synthetic Example 4 — 2 | BL-1 4 | Methanol 94 | Polypropylene nonwoven fabric | 72 | 0.26 | 17.4 |
| Example A12 | Synthetic Example 5 — 2 | BL-1 4 | Methanol 94 | Polypropylene nonwoven fabric | 72 | 0.26 | 15.7 |
| Example A13 | Synthetic Example 6 — 2 | — | Methanol 98 | PTFE membrane filter | — | — | — |
| Comparative Example A1 | Compound of formula (395) — 2 | — | Methanol 98 | Polypropylene nonwoven fabric | 72 | 0.26 | — |
| Comparative Example A2 | Compound of formula (396) — 2 | — | Methanol 98 | Polypropylene nonwoven fabric | 72 | 0.26 | — |
| Comparative Example A3 | Compound of formula (397) — 2 | — | Methanol 98 | PTFE membrane filter | — | — | — |

TABLE 2A

| | Initial performance | | After ultrasonic washing for 3 hours | | After ultrasonic washing for 6 hours | | After ultrasonic washing for 8 hours | |
|---|---|---|---|---|---|---|---|---|
| | Water | n-hexadecane | Water | n-hexadecane | Water | n-hexadecane | Water | n-hexadecane |
| Example A1 | A Hydrophilicity | C Oil repellency | A Hydrophilicity | C Oil repellency | A Hydrophilicity | C Oil repellency | A Hydrophilicity | C Oil repellency |
| Example A2 | A Hydrophilicity | C Oil repellency | A Hydrophilicity | C Oil repellency | A Hydrophilicity | C Oil repellency | B Hydrophilicity | A Lipophilicity |
| Example A3 | A Hydrophilicity | C Oil repellency | A Hydrophilicity | C Oil repellency | A Hydrophilicity | C Oil repellency | A Hydrophilicity | C Oil repellency |
| Example A4 | A Hydrophilicity | C Oil repellency | A Hydrophilicity | C Oil repellency | A Hydrophilicity | C Oil repellency | A Hydrophilicity | A Lipophilicity |
| Example A5 | A Hydrophilicity | C Oil repellency | A Hydrophilicity | C Oil repellency | A Hydrophilicity | C Oil repellency | A Hydrophilicity | A Lipophilicity |
| Example A6 | A Hydrophilicity | C Oil repellency | A Hydrophilicity | C Oil repellency | C Water repellency | B Lipophilicity | — | — |
| Example A7 | A Hydrophilicity | C Oil repellency | A Hydrophilicity | A Lipophilicity | — | — | — | — |
| Example A8 | A Hydrophilicity | C Oil repellency | A Hydrophilicity | C Oil repellency | A Hydrophilicity | A Lipophilicity | — | — |
| Example A9 | A Hydrophilicity | C Oil repellency | A Hydrophilicity | C Oil repellency | A Hydrophilicity | A Lipophilicity | — | — |
| Example A10 | A Hydrophilicity | C Oil repellency | B Hydrophilicity | A Lipophilicity | — | — | — | — |
| Example A11 | A Hydrophilicity | C Oil repellency | B Hydrophilicity | A Lipophilicity | — | — | — | — |
| Example A12 | B Hydrophilicity | C Oil repellency | B Hydrophilicity | A Lipophilicity | — | — | — | — |

TABLE 2B

| | Initial performance | | After ultrasonic washing for 3 hours | | After ultrasonic washing for 6 hours | | After ultrasonic washing for 8 hours | |
|---|---|---|---|---|---|---|---|---|
| | Water | n-hexadecane | Water | n-hexadecane | Water | n-hexadecane | Water | n-hexadecane |
| Example A13 | A Hydrophilicity | C Oil repellency | — | — | — | — | — | — |
| Comparative Example A1 | A Hydrophilicity | A Lipophilicity | — | — | — | — | — | — |
| Comparative Example A2 | A Hydrophilicity | A Lipophilicity | — | — | — | — | — | — |

TABLE 2B-continued

|  | Initial performance | | After ultrasonic washing for 3 hours | | After ultrasonic washing for 6 hours | | After ultrasonic washing for 8 hours | |
| --- | --- | --- | --- | --- | --- | --- | --- | --- |
|  | Water | n-hexadecane | Water | n-hexadecane | Water | n-hexadecane | Water | n-hexadecane |
| Comparative Example A3 | C Water repellency | B Lipophilicity | — | — | — | — | — | — |

As shown in Table 2, in the permeation test filter in Examples A1 and A3, initial performance of permeability was hydrophilic and oil-repellent properties, and the hydrophilic and oil-repellent properties were also maintained after eight hours from when the ultrasonic washing was performed. The reason that the permeation test filter in this example shows the hydrophilic and oil-repellent properties is supposed as follows. That is, a nitrogen-containing perfluoroalkyl group or a nitrogen-containing perfluoroalkylene group which is an oil-repellency imparting group is aligned to the surface, and thus oil repellent properties is exhibited in an air. If water is brought into contact with the filter, the hydrophilicity imparting group such as a carbonyl group and a sulfonyl group is aligned to the surface, and thus hydrophilicity is exhibited.

In the permeation test filter in Examples A2, A4, and A5, initial performance of permeability was hydrophilic and oil-repellent properties, and the hydrophilic and oil-repellent properties were also maintained after six hours from when the ultrasonic washing was performed.

In the permeation test filter in Examples A6, A8, and A9, initial performance of permeability was hydrophilic and oil-repellent properties, and the hydrophilic and oil-repellent properties were also maintained after three hours from when the ultrasonic washing was performed.

It could be confirmed that, in the permeation test filter in the Examples A7, A10, A11, A12, and A13, initial performance of permeability was hydrophilic and oil-repellent properties. Regarding Examples A7, A10, A11, and A12, hydrophilicity was also maintained after three hours from when the ultrasonic washing was performed.

On the contrary, in the permeation test filter in Comparative Examples A1 to A2, a permeation result of water was "A", a permeation result of n-hexadecane was "A", and thus it was confirmed that the permeation test filter was hydrophilic and lipophilic properties.

In the permeation test filter in Comparative Example A3, a permeation result of water was "C", a permeation result of n-hexadecane was "B", and thus it was confirmed that the permeation test filter was water-repellent and lipophilic properties.

As illustrated in FIG. 1, if water and n-hexadecane each was dropped in a nonwoven fabric filter which was subjected to surface treatment with an oil-repellent hydrophilic agent, and was the filter medium according to the present invention, water was spread, and was permeated into the nonwoven fabric filter. On the contrary, n-hexadecane was held to have an oil droplet shape.

Figure 2:
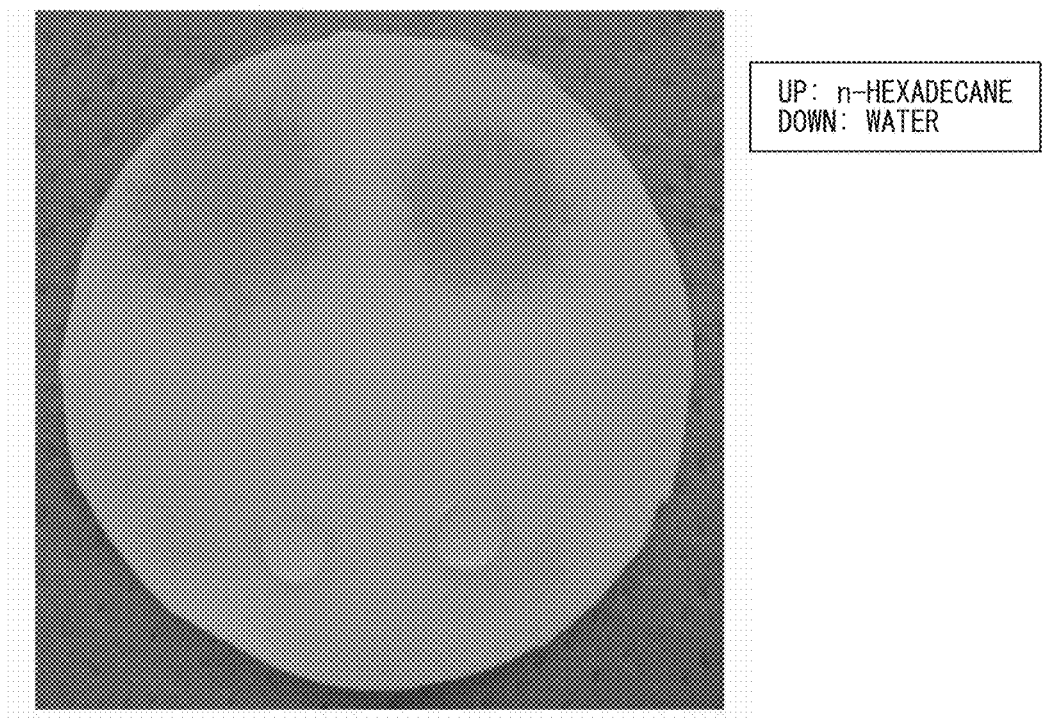
FIG. 2 is a picture showing a representative state of a permeation test result of a not-treated nonwoven fabric filter.

Similarly, as illustrated in FIG. 2, if water and n-hexadecane each was dropped in a not-treated nonwoven fabric, water was held to have a water droplet shape, and n-hexadecane was spread, and was permeated into the nonwoven fabric filter.

<Evaluation by Oil-Water Separation Test>

Example A14

Polypropylene nonwoven fabric (basis weight: 15 g/m², thickness: 0.16 mm, average pore diameter: 7 μm, and maximum pore diameter: 14 μm) was cut off so as to have a circular filter shape having a diameter of 60 mm. The polypropylene nonwoven fabric was immersion-treated in a liquid (surface coating material). Then, natural drying was performed (increased amount after drying: 0.0141 g), and an oil-water separation test was performed at a room temperature in a normal-pressure filtration device. In the liquid (surface coating material), 2 g of a nitrogen-containing fluorine compound synthesized as an oil-repellent hydrophilic agent in Synthetic Example 1, and 4 g of polyvinyl butyral (S-LEC BL-1 manufactured by SEKISUT CHEMICAL CO., LTD.) were dissolved in 94 g of methanol.

A liquid mixture of 30 mL of water and 10 mL of n-hexadecane was used as a test liquid.

When the test liquid was supplied to a normal-pressure filtration device, with stirring well, water passed through the nonwoven fabric (permeation flux: 1.2 cm/min), and n-hexadecane passing through the nonwoven fabric was not possible. Thus, oil was completely separated.

Example A15

Polypropylene nonwoven fabric (basis weight: 20 g/m², thickness: 0.21 mm, average pore diameter: 14 μm, and maximum pore diameter: 23 μm) was cut off so as to have a circular filter shape having a diameter of 60 mm. The polypropylene nonwoven fabric was immersion-treated in a surface coating material having the same composition as that in Example A14. Then, natural drying was performed (increased amount after drying: 0.0298 g), and the oil-water separation test was performed at a room temperature in a normal-pressure filtration device.

A liquid mixture of 30 mL of water and 10 mL of n-hexadecane was used as a test liquid.

When the test liquid was supplied to a normal-pressure filtration device, with stirring well, water passed through the nonwoven fabric (permeation flux: 2.4 cm/min), and n-hexadecane passing through the nonwoven fabric was not possible. Thus, oil was completely separated.

Example A16

Polypropylene nonwoven fabric (basis weight: 20 g/m², thickness: 0.24 mm, average pore diameter: 21 μm, and maximum pore diameter: 37 μm) was cut off so as to have a circular filter shape having a diameter of 60 mm. The polypropylene nonwoven fabric was immersion-treated in a surface coating material having the same composition as that in Example A14. Then, natural drying was performed (increased amount after drying: 0.0216 g), and the oil-water separation test was performed at a room temperature in a normal-pressure filtration device.

A liquid mixture of 30 mL of water and 10 mL of n-hexadecane was used as a test liquid.

When the test liquid was supplied to a normal-pressure filtration device, with stirring well, water passed through the nonwoven fabric (permeation flux: 6.3 cm/min), and n-hexadecane passing through the nonwoven fabric was not possible. Thus, oil was completely separated.

Example A17

5 parts by mass of a nitrogen-containing fluorine compound synthesized in Synthetic Example 7 as the nitrogen-containing fluorine compound, 5 parts by mass of polyvinyl alcohol (reagent manufactured by Wako Pure Chemical Industries, Ltd.) as the binder, and 95 parts by mass of water as the solvent were mixed at the above proportions, thereby a surface coating material was manufactured.

Then, a commercial nylon mesh (aperture of 161 μm) was used as the base. The base was dipped into the surface coating material, and the material was sufficiently impregnated. The base was brought back, and then natural drying was performed so as to remove the solvent. Thus, a permeation test sample was manufactured. Then, permeability was evaluated by a method similar to that in Example A1. The following Table 3 shows manufacturing conditions. The following Table 4 shows evaluation results. "The surface coating material adhering amount (solid)" in Table 3 corresponds to the amount of solid of the surface coating material adhering to the base.

Example A18

5 parts by mass of a nitrogen-containing fluorine compound synthesized in Synthetic Example 8 as the nitrogen-containing fluorine compound, and 5 parts by mass of polyvinyl butyral (S-LEC BL-1 manufactured by SEKISUI CHEMICAL CO., LTD.) as the binder were mixed with 95 parts by mass of ethanol as the solvent, at the above proportions, thereby a surface coating material was manufactured.

Then, a commercial nylon mesh (aperture of 86 μm) was used as the base. The base was dipped into the surface coating material, and the liquid was sufficiently impregnated. The base was brought back, and then natural drying was performed so as to remove the solvent. Thus, a permeation test sample was manufactured. Then, permeability was evaluated by a method similar to that in Example A1. The following Table 3 shows manufacturing conditions. The following Table 4 shows evaluation results.

Example A19

0.5 parts by mass of a nitrogen-containing fluorine compound synthesized in Synthetic Example 9 as the oil-repellent hydrophilic agent, and 0.5 parts by mass of polyvinyl butyral (S-LEC BL-1 manufactured by SEKISUI CHEMICAL CO., LTD.) as the binder, 0.5 parts by mass of silica sol ("IPA-ST" manufactured by NISSAN CHEMICAL INDUSTRIES. LTD.) as the additive, and 98.5 parts by mass of ethanol as the solvent were mixed, at the above proportions, thereby a surface coating material was manufactured.

Then, commercial cellulose filter paper (ADVANTEC quantitative filter paper No. 5B, retention particle diameter of 4 μm) having a diameter of 47 mm was used as the base. The base was dipped into the surface coating material, and the material was sufficiently impregnated. The base was brought back, and then natural drying was performed so as to remove the solvent. Thus, a permeation test sample was manufactured. Then, permeability was evaluated by a method similar to that in Example A1. The following Table 3 shows manufacturing conditions. The following Table 4 shows evaluation results.

Example A20

0.25 parts by mass of a nitrogen-containing fluorine compound synthesized in Synthetic Example 5 and 0.25 parts by mass of a nitrogen-containing fluorine compound synthesized in Synthetic Example 6 as the oil-repellent hydrophilic agent, 4.5 parts by mass of water glass (No. 3 manufactured by Fuji Chemicals Corp.) as the binder were mixed and dissolved in 95 parts by mass of water-methanol solvent mixture (mass ratio of 1:1) at the above proportions, thereby a surface coating material was manufactured.

Then, a commercial glass filter (SIBATA 1GP16, pore size of 10 to 16 μm) was used as the base. The base was dipped into the surface coating material, and the material was sufficiently impregnated. The base was brought back, and then heating and curing was performed at 150° C. for 30 minutes. Thus, a permeation test sample was manufactured. Then, permeability was evaluated by a method similar to that in Example A1. The following Table 3 shows manufacturing conditions. The following Table 4 shows evaluation results.

Example A21

1 part by mass of a nitrogen-containing fluorine compound synthesized in Synthetic Example 10 as the oil-repellent hydrophilic agent, 1 part by mass of polyvinyl butyral (S-LEC BL-1 manufactured by SEKISUT CHEMICAL CO., LTD.) as the binder, and 0.1 parts by mass of tetraethoxysilane (10 mass % of ethanol solution in SiO2 conversion) were mixed and dissolved at the above proportions, in 99 parts by mass of methanol as the solvent. Thus, a surface coating material was manufactured.

Then, an object obtained by cutting off commercial blend filter cloth (TEFAIRE TFA-65) of PFTE 75% and glass fiber 25% was used as the base. The base was dipped into the surface coating material, and the material was sufficiently impregnated. The base was brought back, and then heating and curing was performed at 120° C. for 30 minutes. Thus, a permeation test sample was manufactured. Then, permeability was evaluated by a method similar to that in Example A1. The following Table 3 shows manufacturing conditions. The following Table 4 shows evaluation results.

Example A22

2 parts by mass of a nitrogen-containing fluorine compound synthesized in Synthetic Example 11 as the nitrogen-containing fluorine compound, and 4 parts by mass of polyvinyl butyral (S-LEC BH-3 manufactured by SEKISUI CHEMICAL CO., LTD.) as the binder, and 94 parts by mass of ethanol as the solvent were mixed and dissolved at the above proportions, thereby a surface coating material was manufactured.

Then, particles of 45 to 75 μm obtained by grinding and sieving anthracite (commercial product filtration sand: effective diameter of 1 mm) were sorted as the base. 5 parts by mass of the anthracite was immersed in 100 parts by mass of the above-described surface coating material, and the surface coating material was sufficiently impregnated. Then, the solution was filtered, and thus anthracite subjected to hydrophilic and oil-repellent treatment was collected. Drying at 60° C. was performed so as to remove the solvent. The anthracite which was obtained by the hydrophilic and oil-repellent treatment was laid on filter paper No. 5C (manufactured by Kiriyama glass Co., diameter of 21 mm) so as to obtain an aggregate. Then, permeability was evaluated by a method similar to that in Example A1. The following Table 3 shows manufacturing conditions. The following Table 4 shows evaluation results.

Example A23

2 parts by mass of a nitrogen-containing fluorine compound synthesized in Synthetic Example 12 as the nitrogen-containing fluorine compound, and 4 parts by mass of polyvinyl butyral (S-LEC BL-1 manufactured by SEKISUI CHEMICAL CO., LTD.) as the binder, and 94 parts by mass of ethanol as the solvent were mixed and dissolved at the above proportions, thereby a surface coating material was manufactured.

Then, porous granular type silica gel (WAKO GEL C-300 manufactured by Wako Pure Chemical Industries, Ltd.) having granularity of 45 to 75 μm was used as the base. 5 parts by mass of silica gel was immersed in 100 parts by mass of the above-described surface coating material, and the surface coating material was sufficiently impregnated. Then, the solution was filtered, and thus silica gel subjected to hydrophilic and oil-repellent treatment was collected. Drying at 60° C. was performed so as to remove the solvent. The silica gel which was obtained by the hydrophilic and oil-repellent treatment was laid on filter paper No. 5C (manufactured by Kiriyama glass Co., diameter of 21 mm) so as to obtain an aggregate. Then, permeability was evaluated by a method similar to that in Example A1. The following Table 3 shows manufacturing conditions. The following Table 4 shows evaluation results.

Example A24

2 parts by mass of a nitrogen-containing fluorine compound synthesized in Synthetic Example 13 as the nitrogen-containing fluorine compound, and 4 parts by mass of polyvinyl butyral (S-LEC BL-1 manufactured by SEKISUI CHEMICAL CO., LTD.) as the binder, and 94 parts by mass of ethanol as the solvent were mixed and dissolved at the above proportions, thereby a surface coating material was manufactured.

Then, γ-alumina (reagent manufactured by Wako Pure Chemical Industries, Ltd.) was used as the base. Sieving was performed so as to select particles of 45 to 75 μm. 5 parts by mass of γ-alumina was immersed in 100 parts by mass of the above-described surface coating material, and the surface coating material was sufficiently impregnated. Then, the solution was filtered, and thus γ-alumina subjected to hydrophilic and oil-repellent treatment was collected. Drying at 60° C. was performed so as to remove the solvent. The γ-alumina which was obtained by the hydrophilic and oil-repellent treatment was laid on filter paper No. 5C (manufactured by Kiriyama glass Co., diameter of 21 mm) so as to obtain an aggregate. Then, permeability was evaluated by a method similar to that in Example A1. The following Table 3 shows manufacturing conditions. The following Table 4 shows evaluation results.

Example A25

2 parts by mass of a nitrogen-containing fluorine compound synthesized in Synthetic Example 14 as the nitrogen-containing fluorine compound, and 4 parts by mass of polyvinyl butyral (S-LEC KS-10 manufactured by SEKISUI CHEMICAL CO., LTD.) as the binder, and 94 parts by mass of ethanol as the solvent were mixed and dissolved at the above proportions, thereby a surface coating material was manufactured.

Then, zeolite (manufactured by UNION SHOWA: molecular sieve 13× powder) was used as the base, and sieving was performed so as to select particles of 45 to 75 μm. 5 parts by mass of the zeolite was immersed in 100 parts by mass of the above-described surface coating material, and the surface coating material was sufficiently impregnated. Then, the solution was filtered, and thus zeolite subjected to hydrophilic and oil-repellent treatment was collected. Drying at 60° C. was performed so as to remove the solvent. The zeolite which was obtained by the hydrophilic and oil-repellent treatment was laid on filter paper No. 5C (manufactured by Kiriyama glass Co., diameter of 21 mm) so as to obtain an aggregate. Then, permeability was evaluated by a method similar to that in Example A1. The following Table 3 shows manufacturing conditions. The following Table 4 shows evaluation results.

Example A26

2 parts by mass of a nitrogen-containing fluorine compound synthesized in Synthetic Example 15 as the nitrogen-containing fluorine compound, and 4 parts by mass of polyvinyl butyral (S-LEC BL-1 manufactured by SEKISUI CHEMICAL CO., LTD.) as the binder, and 94 parts by mass of ethanol as the solvent were mixed and dissolved at the above proportions, thereby a surface coating material was manufactured.

Then, montmorillonite (manufactured by HOJUN., Co., Ltd.: organic bentonite ESBEN W) which is clay mineral was used as the base, and sieving was performed so as to select particles of 45 to 75 μm. 5 parts by mass of the clay mineral was immersed in 100 parts by mass of the above-described surface coating material, and the surface coating material was sufficiently impregnated. Then, the solution was filtered, and thus clay mineral subjected to hydrophilic and oil-repellent treatment was collected. Drying at 60° C. was performed so as to remove the solvent. The clay mineral which was obtained by the hydrophilic and oil-repellent treatment was laid on filter paper No. 5C (manufactured by Kiriyama glass Co., diameter of 21 mm) so as to obtain an aggregate. Then, permeability was evaluated by a method similar to that in Example A1. The following Table 3 shows manufacturing conditions. The following Table 4 shows evaluation results.

Example A27

16 parts by mass of perfluoro(3-dibutylaminopropionic acid)calcium synthesized in Synthetic Example 5 as the nitrogen-containing fluorine compound, and 4 parts by mass of polyvinyl butyral ("S-LEC BL-1" manufactured by SEKISUI CHEMICAL CO., LTD.) having a hydrophilic group and a hydroxyl group were dissolved in 180 parts by mass of methanol, thereby a surface coating material was manufactured. Spray drying was performed on the surface coating material by a spray dryer (ADL311S-A manufactured by YAMATO Scientific Co., Ltd.). Thus, nitrogen-containing fluorine compound particles of which the most frequent diameter was 4 μm were obtained. The obtained nitrogen-containing fluorine compound particles were laid on filter paper No. 5C (manufactured by Kiriyama glass Co., diameter of 21 mm) so as to obtain an aggregate. Then, permeability was evaluated by a method similar to that in Example A1. The following Table 3 shows manufacturing conditions. The following Table 4 shows evaluation results.

Example A28

2 parts by mass of a nitrogen-containing fluorine compound synthesized as an oil-repellent hydrophilic agent in Synthetic Example 17 were mixed and dissolved in 98 parts by mass of ethanol as a solvent, at the above proportion, thereby a surface coating material was manufactured. Then, commercial polyester nonwoven fabric (basis weight of 80 g/m$^2$, and thickness of 0.40 mm) was used as the base, and the base was coated with the manufactured surface coating material by using the above-described method. Thus, a permeation test sheet was manufactured. Water and n-hexadecane each was dropped in the permeation test filter, and initial performance and permeability after ultrasonic washing was evaluated. The following Table 3 shows manufacturing conditions. The following Table 4 shows evaluation results.

Example A29

2 parts by mass of a nitrogen-containing fluorine compound synthesized in Synthetic Example 7 as the nitrogen-containing fluorine compound, and 4 parts by mass of polyvinyl butyral (S-LEC BL-1 manufactured by SEKISUT CHEMICAL CO., LTD.) as the binder, and 96 parts by mass of ethanol as the solvent were mixed and dissolved at the above proportions, thereby a surface coating material was manufactured. Then, commercial polyester nonwoven fabric (basis weight of 80 g/m$^2$, and thickness of 0.40 mm) was used as the base, and the base was coated with the manufactured surface coating material by using the above-described method. Thus, a permeation test sheet was manufactured. Water and n-hexadecane each was dropped in the permeation test filter, and initial performance and permeability after ultrasonic washing was evaluated. The following Table 3 shows manufacturing conditions. The following Table 4 shows evaluation results.

Example A30

2 parts by mass of a nitrogen-containing fluorine compound synthesized in Synthetic Example 16 as the nitrogen-containing fluorine compound, and 4 parts by mass of polyvinyl butyral (S-LEC BL-1 manufactured by SEKISUI CHEMICAL CO., LTD.) as the binder, and 96 parts by mass of ethanol as the solvent were mixed and dissolved at the above proportions, thereby a surface coating material was manufactured. Then, commercial polyester nonwoven fabric (basis weight of 80 g/m$^2$, and thickness of 0.40 mm) was used as the base, and the base was coated with the manufactured surface coating material by using the above-described method. Thus, a permeation test sheet was manufactured. Water and n-hexadecane each was dropped in the permeation test filter, and initial performance and permeability after ultrasonic washing was evaluated. The following Table 3 shows manufacturing conditions. The following Table 4 shows evaluation results.

Example A31

2 parts by mass of a nitrogen-containing fluorine compound synthesized in Synthetic Example 17 as the nitrogen-containing fluorine compound, and 4 parts by mass of polyvinyl butyral (S-LEC BL-1 manufactured by SEKISUI CHEMICAL CO., LTD.) as the binder, and 96 parts by mass of ethanol as the solvent were mixed and dissolved at the above proportions, thereby a surface coating material was manufactured. Then, commercial polyester nonwoven fabric (basis weight of 80 g/m$^2$, and thickness of 0.40 mm) was used as the base, and the base was coated with the manufactured surface coating material by using the above-described method. Thus, a permeation test sheet was manufactured. Water and n-hexadecane each was dropped in the permeation test filter, and initial performance and permeability after ultrasonic washing was evaluated. The following Table 3 shows manufacturing conditions. The following Table 4 shows evaluation results.

TABLE 3A

| | Surface coating material | | | | | | | Surface coating material |
|---|---|---|---|---|---|---|---|---|
| | Nitrogen-containing fluorine compound | | Binder | Solvent | Others | Basis | | adhering amount |
| | | [part by mass] | [part by mass] | [part by mass] | [part by mass] | Base | weight [g/m$^2$] | Thickness [mm] | (solid) [g/m$^2$] |
| Example A17 | Synthetic Example 7 | 5 | polyvinyl alcohol 5 | water 95 | | nylon mesh | — | — | — |
| Example A18 | Synthetic Example 8 | 5 | BL-1 5 | ethanol 95 | | nylon mesh | — | — | — |
| Example A19 | Synthetic Example 9 | 0.5 | BL-1 0.5 | ethanol 98.5 | silica sol 0.5 | cellulose filter paper | — | — | — |
| Example A20 | Synthetic Example 5 + Synthetic Example 6 | each 0.25 | water glass 4.5 | solvent mixture of water and methanol 95 | | glass filter | — | — | — |
| Example A21 | Synthetic Example 10 | 1 | BL-1 1 | methanol 99 | tetraethoxysilane 0.1 | blend filter cloth of PFTE 75% and glass fiber 25% | — | — | — |

TABLE 3A-continued

| | Surface coating material | | | | | | | Surface coating material adhering amount |
|---|---|---|---|---|---|---|---|---|
| | Nitrogen-containing fluorine compound | Binder | Solvent | Others | Basis | | | |
| | | | | | Base | weight [g/m²] | Thickness [mm] | (solid) [g/m²] |
| | [part by mass] | [part by mass] | [part by mass] | [part by mass] | | | | |
| Example A22 | Synthetic Example 11 — 2 | BL-1 4 | ethanol 94 | | anthracite | — | — | — |
| Example A23 | Synthetic Example 12 — 2 | BL-1 4 | ethanol 94 | | silica gel | — | — | — |

TABLE 3B

| | Surface coating material | | | | | | | Surface coating material adhering amount |
|---|---|---|---|---|---|---|---|---|
| | Nitrogen-containing fluorine compound | Binder | Solvent | Others | Basis | | | |
| | | | | | Base | weight [g/m²] | Thickness [mm] | (solid) [g/m²] |
| | [part by mass] | [part by mass] | [part by mass] | [part by mass] | | | | |
| Example A24 | Synthetic Example 13 — 2 | BL-1 4 | ethanol 94 | | alumina | — | — | — |
| Example A25 | Synthetic Example 14 — 2 | KS-10 4 | ethanol 94 | | zeolite | — | — | — |
| Example A26 | Synthetic Example 15 — 2 | BL-1 4 | ethanol 94 | | clay mineral | — | — | — |
| Example A27 | Synthetic Example 5 — 16 | BL-1 4 | methanol 180 | | — | — | — | — |
| Example A28 | Synthetic Example 17 — 2 | — | ethanol 98 | | polyester nonwoven fabric | 80 | 0.4 | 9.1 |
| Example A29 | Synthetic Example 7 — 2 | BL-1 4 | ethanol 96 | | polyester nonwoven fabric | 80 | 0.4 | 25.9 |
| Example A30 | Synthetic Example 16 — 2 | BL-1 4 | ethanol 96 | | polyester nonwoven fabric | 80 | 0.4 | 27.7 |
| Example A31 | Synthetic Example 17 — 2 | BL-1 4 | ethanol 96 | | polyester nonwoven fabric | 80 | 0.4 | 24.4 |

TABLE 4A

| | Initial performance | | After ultrasonic washing for 3 hours | | After ultrasonic washing for 6 hours | | After ultrasonic washing for 8 hours | |
|---|---|---|---|---|---|---|---|---|
| | Water | n-hexadecane | Water | n-hexadecane | Water | n-hexadecane | Water | n-hexadecane |
| Example A17 | A Hydrophilicity | C Oil repellency | — | — | — | — | — | — |
| Example A18 | A Hydrophilicity | C Oil repellency | — | — | — | — | — | — |
| Example A19 | A Hydrophilicity | C Oil repellency | — | — | — | — | — | — |
| Example A20 | A Hydrophilicity | C Oil repellency | — | — | — | — | — | — |
| Example A21 | A Hydrophilicity | C Oil repellency | — | — | — | — | — | — |
| Example A22 | A Hydrophilicity | C Oil repellency | — | — | — | — | — | — |
| Example A23 | A Hydrophilicity | C Oil repellency | — | — | — | — | — | — |
| Example A24 | A Hydrophilicity | C Oil repellency | — | — | — | — | — | — |

TABLE 4A-continued

| | Initial performance | | After ultrasonic washing for 3 hours | | After ultrasonic washing for 6 hours | | After ultrasonic washing for 8 hours | |
| --- | --- | --- | --- | --- | --- | --- | --- | --- |
| | Water | n-hexadecane | Water | n-hexadecane | Water | n-hexadecane | Water | n-hexadecane |
| Example A25 | A<br>Hydrophilicity | C<br>Oil repellency | — | — | — | — | — | — |
| Example A26 | A<br>Hydrophilicity | C<br>Oil repellency | — | — | — | — | — | — |
| Example A27 | A<br>Hydrophilicity | C<br>Oil repellency | — | — | — | — | — | — |
| Example A28 | A<br>Hydrophilicity | C<br>Oil repellency | A<br>Hydrophilicity | C<br>Oil repellency | A<br>Hydrophilicity | C<br>Oil repellency | A<br>70 hours<br>Hydrophilicity | C<br>70 hours<br>Oil repellency |

TABLE 4B

| | Initial performance | | After ultrasonic washing for 3 hours | | After ultrasonic washing for 6 hours | | After ultrasonic washing for 8 hours | |
| --- | --- | --- | --- | --- | --- | --- | --- | --- |
| | Water | n-hexadecane | Water | n-hexadecane | Water | n-hexadecane | Water | n-hexadecane |
| Example A29 | A<br>Hydrophilicity | C<br>Oil repellency | A<br>Hydrophilicity | C<br>Oil repellency | A<br>Hydrophilicity | C<br>Oil repellency | A<br>70 hours<br>Hydrophilicity | C<br>70 hours<br>Oil repellency |
| Example A30 | A<br>Hydrophilicity | C<br>Oil repellency | A<br>Hydrophilicity | C<br>Oil repellency | A<br>Hydrophilicity | C<br>Oil repellency | A<br>90 hours<br>Hydrophilicity | C<br>90 hours<br>Oil repellency |
| Example A31 | A<br>Hydrophilicity | C<br>Oil repellency | A<br>Hydrophilicity | C<br>Oil repellency | A<br>Hydrophilicity | C<br>Oil repellency | A<br>90 hours<br>Hydrophilicity | C<br>90 hours<br>Oil repellency |

As shown in Table 4, in the permeability test filter in Examples A17 to A21, initial performance of permeability was hydrophilic and oil-repellent properties. However, any one showed the hydrophilic and oil-repellent properties.

Regarding an aggregate of fine particles which were surface-treated with the nitrogen-containing fluorine compound in Examples A22 to A26, initial performance of permeability of water and n-hexadecane was evaluated. However, in any aggregate of fine particles, water was not permeated, but hexadecane showed the hydrophilic and oil-repellent properties without being permeated.

Regarding an aggregate of particles of the nitrogen-containing fluorine compound in Example A27, initial performance of permeability of water and n-hexadecane was evaluated. As a result, regarding the aggregate of particles of the nitrogen-containing fluorine compound, water was not permeated, but hexadecane showed the hydrophilic and oil-repellent properties without being permeated. The permeability test filter in Examples A28 to A31 showed the hydrophilic and oil-repellent properties even though ultrasonic washing was performed for a long term.

Example B (Binder)

Acrylic polymer (ARUFON UC-3000 manufactured by TOAGOSEI CO., LTD.), polyvinyl butyral (S-LEC B, BL-1, S-LEC BH-3 manufactured by SEKISUI CHEMICAL CO LTD.), and polyvinyl alcohol (reagent manufactured by Wako Pure Chemical Industries, Ltd., GOHSENX Z-410 manufactured by Nippon Synthetic Chemical Industry Co., Ltd.) were used as the binder.

<Manufacturing of Surface Coating Material>

The oil-repellent hydrophilic agent, the binder, an inorganic compound having charges, an inorganic compound having ionicity, fluororesin particles, and a solvent were mixed at a predetermined proportion, thereby a surface coating material was manufactured.

<Initial Evaluation of Hydrophilic and Oil-Repellent Properties by Permeation Test>

Nonwoven fabric which was cut off so as to have a circular shape having a diameter of 47 mm was dipped into a surface coating material, and the material was sufficiently impregnated. The nonwoven fabric was brought back, and then natural drying was performed so as to remove the solvent. Thus, a permeation test sheet was manufactured.

Water and n-hexadecane each was dropped in the produced permeation test sheet. Permeability was visually determined based on the following definitions, and thus the hydrophilic and oil-repellent properties were evaluated.

<Durability Evaluation of Hydrophilic and Oil-Repellent Properties by Ultrasonic Washing>

The permeation test sheet was immersed in 50 ml of pure water, and ultrasonic washing was performed at room temperature by using an ultrasonic washer USK-5R (240 W, 40 kHz) manufactured by AS ONE corporation.

Replacement with pure water was performed for each of 90 minutes during a period from ultrasonic wave irradiation start to six hours, and was performed for each of 60 minutes during a period after six hours.

After ten hours from ultrasonic wave irradiation, after 20 hours, after 30 hours, after 40 hours, after 60 hours, after 80 hours, or at an intermediate time thereof, the sheet was extracted, and the hydrophilic and oil-repellent properties were evaluated by a method similar to that for the permeation test.

For a dropping method of water and n-hexadecane, the following conditions were used.

Dropped quantity: (40 to 45) μL/droplet (water)

Dropped quantity: (20 to 25) μL/droplet (n-hexadecane)

Dropping height: 5 cm from the surface of filter
Dropping tool: polyfiller
Measurement temperature: room temperature (22±1° C.)
In the permeation test sheet treated with the surface coating material, evaluation criteria for the hydrophilicity and the oil repellent properties are as follows.
(Criteria for Evaluating Hydrophilicity)
When a time until a liquid is completely permeated after water is dropped is set to T,
A: permeation occurs for T<1 second
B: permeation occurs for a period of 1 second≤F<60 seconds
C: permeation occurs for a period of 60 seconds≤T<300 seconds (five minutes)
D: permeation occurs for a period of 300 seconds≤T<1,800 seconds (30 minutes)
E: permeation does not occur even for a period of T≥1,800 seconds (30 minutes)
(Criteria for Evaluating Oil Repellent Properties)
When a time until a liquid is completely permeated after n-hexadecane is dropped is set to T,
A: base is never permeated even after a period of T≥1,800 seconds (30 minutes), that is, 30 minutes elapses
B: base is permeated for 30 minutes
C: permeation occurs for a period of five seconds T<1,800 seconds (30 minutes)
D: permeation occurs for a period of T<five seconds
Regarding nonwoven fabric before treatment with the surface coating material, hydrophilicity evaluation was performed. Specifically, the above definitions were applied. If a result of the hydrophilicity evaluation corresponded to A to C, evaluation as "hydrophilicity" was performed. If the result corresponded to D and E, evaluation as "hydrophobicity" was performed.

Example B1

2 parts by mass of a nitrogen-containing fluorine compound synthesized in Synthetic Example 1 as the oil-repellent hydrophilic agent, 4 parts by mass of acrylic polymer (ARUFON UC-3000 manufactured by TOAGOSEI CO., LTD.) as the binder, and 94 parts by mass of ethanol as the solvent were mixed and sufficiently dispersed at the above proportions, thereby a surface coating material was manufactured.
Then, a medium (hydrophilicity: B) obtained in a manner that commercial polypropylene nonwoven fabric (basis weight of 72 g/m$^2$, and thickness of 0.26 mm) was subjected to sulfonation treatment by a method described in Japanese Patent No. 2715153 was used as the base. The base was coated with the manufactured surface coating material by using the above-described method, thereby a permeation test sheet was manufactured. The following Table 5 shows manufacturing conditions. "The surface coating material adhering amount (solid)" in Table 5 corresponds to the amount of solid of the surface coating material adhering to the base.
Water and n-hexadecane each was dropped in the permeation test filter in Example B1, and initial performance and permeability after ultrasonic washing was evaluated. The following Table 6 shows evaluation results.

Example B2

Commercial polyester nonwoven fabric (basis weight of 80 g/m$^2$, and thickness of 0.40 mm) was stirred in 5 mass % of a caustic soda aqueous solution at 50° C. for three hours, so as to perform alkali treatment. After flowing water washing, drying was performed at 80° C. for 16 hours. A medium (hydrophilicity: A) obtained by the drying was used. A permeation test sheet was manufactured by using the medium. The manufacturing was performed in a manner similar to that in Example B1 except that 0.5 parts by mass of a nitrogen-containing fluorine compound synthesized in Synthetic Example 1 were used as the oil-repellent hydrophilic agent, 0.5 parts by mass of polyvinyl butyral ("S-LEC BL-1" manufactured by SEKISUI CHEMICAL CO LTD.) were used as the binder, and 98 parts by mass of ethanol as the solvent were used. Then, initial performance and permeability after ultrasonic washing was evaluated by using a method similar to that in Example B1. The following Table 5 shows manufacturing conditions. The following Table 6 shows evaluation results.

Example B3

Commercial vinylon nonwoven fabric (basis weight of 100.1 g/m$^2$, thickness of 0.30 mm, and hydrophilicity: B) was used as the base. A permeation test sheet was manufactured by using the medium. The manufacturing was performed in a manner similar to that in Example B1 except that 4 parts by mass of polyvinyl butyral ("S-LEC B BH-3" manufactured by SEKISUI CHEMICAL CO., LTD.) were used as the binder. Then, initial performance and permeability after ultrasonic washing was evaluated by using a method similar to that in Example B1. The following Table 5 shows manufacturing conditions. The following Table 6 shows evaluation results.

Example B4

Commercial pulp-polyester mixed nonwoven fabric (basis weight of 73.5 g/m$^2$, thickness of 0.20 mm, and hydrophilicity: B) was used as the base. A permeation test sheet was manufactured by using the medium. The manufacturing was performed in a manner similar to that in Example B1 except that 4 parts by mass of polyvinyl butyral ("S-LEC B BH-3" manufactured by SEKISUI CHEMICAL CO., LTD.) were used as the binder. Then, initial performance and permeability after ultrasonic washing was evaluated by using a method similar to that in Example B1. The following Table 5 shows manufacturing conditions. The following Table 6 shows evaluation results.

Example B5

Commercial vinylon-cellulose mixed nonwoven fabric (hydrophilicity: A) was used as the base. A permeation test sheet was manufactured by using the medium. The manufacturing was performed in a manner similar to that in Example B1 except that 4 parts by mass of polyvinyl butyral ("S-LEC B BH-3" manufactured by SEKISUI CHEMICAL CO., LTD.) were used as the binder. Then, initial performance and permeability after ultrasonic washing was evaluated by using a method similar to that in Example B1. The following Table 5 shows manufacturing conditions. The following Table 6 shows evaluation results.

Example B6

A permeation test sheet was manufactured in a manner similar to that in Example B1 except that 2 parts by mass of a nitrogen-containing fluorine compound synthesized in Synthetic Example 2 was used as the oil-repellent hydrophilic agent, and 4 parts by mass of polyvinyl butyral (S-LEC B BH-3 manufactured by SEKISUI CHEMICAL CO., LTD.) was used as the binder. Then, initial performance and permeability after ultrasonic washing was evaluated by using a method similar to that in Example B1. The following Table 5 shows manufacturing conditions. The following Table 6 shows evaluation results.

Example B7

A permeation test sheet was manufactured in a manner similar to that in Example B1 except that 2 parts by mass of a nitrogen-containing fluorine compound synthesized in Synthetic Example 18 was used as the oil-repellent hydrophilic agent, and 4 parts by mass of polyvinyl butyral (S-LEC B BH-3 manufactured by SEKISUI CHEMICAL CO., LTD.) was used as the binder. Then, initial performance and permeability after ultrasonic washing was evaluated by using a method similar to that in Example B1. The following Table 5 shows manufacturing conditions. The following Table 6 shows evaluation results.

Example B8

A permeation test sheet was manufactured in a manner similar to that in Example B1 except that 2 parts by mass of a nitrogen-containing fluorine compound synthesized in Synthetic Example 12 was used as the oil-repellent hydrophilic agent, 20 parts by mass of polyvinyl butyral ("S-LEC BL-1" manufactured by SEKISUI CHEMICAL CO., LTD.) was used as the binder, and 78 parts by mass of methanol was used as the solvent. Then, initial performance and permeability after ultrasonic washing was evaluated by using a method similar to that in Example B1. The following Table 5 shows manufacturing conditions. The following Table 6 shows evaluation results.

Example B9

A medium (hydrophilicity: A) obtained in a manner that commercial polypropylene nonwoven fabric (basis weight of 40 g/m$^2$, and thickness of 0.09 mm) was subjected to hydrophilic treatment by a method described in Japanese Patent No. 2930376 was used as the base. A permeation test sheet was manufactured by using the medium, in a manner similar to that in Example B1 except that 2 parts by mass of a nitrogen-containing fluorine compound synthesized in Synthetic Example 15 was used as the oil-repellent hydrophilic agent, and 4 parts by mass of polyvinyl butyral ("S-LEC B BH-3" manufactured by SEKISUI CHEMICAL CO LTD.) was used as the binder. Then, initial performance and permeability after ultrasonic washing was evaluated by using a method similar to that in Example B1. The following Table 5 shows manufacturing conditions. The following Table 6 shows evaluation results.

Example B10

Polyester nonwoven fabric used in Example B2 was used as the base. A permeation test sheet was manufactured by using the fabric, in a manner similar to that in Example B1 except that 2 parts by mass of a nitrogen-containing fluorine compound synthesized in Synthetic Example 3 were used as the oil-repellent hydrophilic agent, 98 parts by mass of ethanol were used as the solvent, and the binder was not used. Then, initial performance and permeability after ultrasonic washing was evaluated by using a method similar to that in Example B1. The following Table 5 shows manufacturing conditions. The following Table 6 shows evaluation results.

Example B11

Polyester nonwoven fabric used in Example B2 was used as the base. A permeation test sheet was manufactured by using the fabric, in a manner similar to that in Example B1 except that 2 parts by mass of a nitrogen-containing fluorine compound synthesized in Synthetic Example 7 was used as the oil-repellent hydrophilic agent, 98 parts by mass of ethanol was used as the solvent, and the binder was not used. Then, initial performance and permeability after ultrasonic washing was evaluated by using a method similar to that in Example B1. The following Table 5 shows manufacturing conditions. The following Table 6 shows evaluation results.

Example B12

2 parts by mass of a nitrogen-containing fluorine compound synthesized in Synthetic Example 7 as the oil-repellent hydrophilic agent, 4 parts by mass of polyvinyl alcohol (reagent manufactured by Wako Pure Chemical Industries, Ltd.) as the binder, and 94 parts by mass of water as the solvent were mixed at the above proportions, thereby a surface coating material was manufactured.

Then, a commercial nylon mesh (aperture of 161 μm, thickness of 0.12 mm, and hydrophilicity: C) was used as the base. The base was dipped into the surface coating material, and the liquid was sufficiently impregnated. The base was brought back, and then natural drying was performed so as to remove the solvent. Thus, a permeation test sheet was manufactured. Then, permeability was evaluated by a method similar to that in Example B1. The following Table 5 shows manufacturing conditions. The following Table 6 shows evaluation results.

Example B13

A permeation test sheet was manufactured in a manner similar to that in Example B1 except that 2 parts by mass of a nitrogen-containing fluorine compound synthesized in Synthetic Example 9 was used as the oil-repellent hydrophilic agent, 0.5 parts by mass of fumed silica ("AEROSIL 300" manufactured by JAPAN AEROSIL corporation) were added as the inorganic compound having charges, and 4 parts by mass of polyvinyl butyral ("S-LEC B BH-3" manufactured by SEKISUI CHEMICAL CO., LTD.) were used as the binder. Then, initial performance and permeability after ultrasonic washing was evaluated by using a method similar to that in Example B1. The following Table 5 shows manufacturing conditions. The following Table 6 shows evaluation results.

Example B14

A permeation test sheet was manufactured in a manner similar to that in Example B1 except that 2 parts by mass of fumed silica ("AEROSIL 300" manufactured by JAPAN AEROSIL corporation) were added as the inorganic compound having charges, and 2 parts by mass of polyvinyl butyral ("S-LEC B BL-1" manufactured by SEKISUI CHEMICAL CO., LTD.) were used as the binder. Then, initial performance and permeability after ultrasonic washing was evaluated by using a method similar to that in Example B1. The following Table 5 shows manufacturing conditions. The following Table 6 shows evaluation results.

Example B15

Polyester nonwoven fabric used in Example B2 was used as the base. A permeation test sheet was manufactured by using the polyester nonwoven fabric. The manufacturing was performed in a manner similar to that in Example B1 except that 3 parts by mass of a nitrogen-containing fluorine compound synthesized in Synthetic Example 1 were used as the oil-repellent hydrophilic agent, 3 parts by mass of fumed silica ("AEROSIL 300" manufactured by JAPAN AEROSIL corporation) were added as the inorganic compound having charges, 4 parts by mass of polyvinyl alcohol ("GOHSENX Z-410" manufactured by Nippon Synthetic Chemical Industry Co., Ltd.) were used as the binder, and 90 parts by mass of water were used as the solvent. Then, initial performance and permeability after ultrasonic washing was evaluated by using a method similar to that in Example B1. The following Table 5 shows manufacturing conditions. The following Table 6 shows evaluation results.

Example B16

A permeation test sheet was manufactured in a manner similar to that in Example B1 except that 4 parts by mass of fumed silica ("AEROSIL 50" manufactured by JAPAN AEROSIL corporation) were added as the inorganic compound having charges, and 4 parts by mass of polyvinyl butyral ("S-LEC B BH-3" manufactured by SEKISUI CHEMICAL CO., LTD.) were used as the binder. Then, initial performance and permeability after ultrasonic washing was evaluated by using a method similar to that in Example B1. The following Table 5 shows manufacturing conditions. The following Table 6 shows evaluation results.

Example B17

A permeation test sheet was manufactured in a manner similar to that in Example B1 except that 2 parts by mass of iron flocculant ("Polytetsu" manufactured by Nittetsu Mining Co., Ltd.) were added as the inorganic compound having ionicity, and 4 parts by mass of polyvinyl butyral ("S-LEC B BL-1" manufactured by SEKISUI CHEMICAL CO., LTD.) were used as the binder. Then, initial performance and permeability after ultrasonic washing was evaluated by using a method similar to that in Example B1. The following Table 5 shows manufacturing conditions. The following Table 6 shows evaluation results.

Example B18

Polyester nonwoven fabric used in Example B2 was used as the base. A permeation test sheet was manufactured in a manner similar to that in Example B1 except that 4 parts by mass of organosilica sol ("IPA-ST" manufactured by NISSAN CHEMICAL INDUSTRIES. LTD.) were added as the inorganic compound having charges, 1 part by mass of polyvinyl butyral ("S-LEC B BL-1" manufactured by SEKISUI CHEMICAL CO., LTD.) was used as the binder, and 93 parts by mass of ethanol were used as the solvent. Then, initial performance and permeability after ultrasonic washing was evaluated by using a method similar to that in Example B1. The following Table 5 shows manufacturing conditions. The following Table 6 shows evaluation results.

Example B19

Polyester nonwoven fabric used in Example B2 was used as the base. A permeation test sheet was manufactured in a manner similar to that in Example B1 except that 4 parts by mass of organosilica sol ("IPA-ST" manufactured by NISSAN CHEMICAL INDUSTRIES. LTD.) were added as the inorganic compound having charges, 4 parts by mass of polyvinyl butyral ("S-LEC B BL-1" manufactured by SEKISUI CHEMICAL CO LTD.) was used as the binder, and 94 parts by mass of a liquid mixture of hexafluoroxylene/ethanol/n-butanol having a mass ratio of 12/8/1 were used as the solvent. Then, initial performance and permeability after ultrasonic washing was evaluated by using a method similar to that in Example B1. The following Table 5 shows manufacturing conditions. The following Table 6 shows evaluation results.

Example B20

A permeation test sheet was manufactured in a manner similar to that in Example B1 except for using a surface coating material obtained by mixing and dissolving 2.5 parts by mass of a nitrogen-containing fluorine compound synthesized in Synthetic Example 1 as the oil-repellent hydrophilic agent, 2 parts by mass of zeolite ("13× powder" manufactured by UNION SHOWA Corp.) as the inorganic compound having charges, 7.5 parts by mass of polyvinyl butyral ("S-LEC B BL-1" manufactured by SEKISUI CHEMICAL CO., LTD.) as the binder, and 88.5 parts by mass of ethanol as the solvent, at the above proportion. Then, initial performance and permeability after ultrasonic washing was evaluated by using a method similar to that in Example B1. The following Table 5 shows manufacturing conditions. The following Table 6 shows evaluation results.

Example B21

A permeation test sheet was manufactured in a manner similar to that in Example B1 except that 2 parts by mass of aluminum sulfate (manufactured by TAIMEI CHEMICALS Co., Ltd.) were added as the inorganic compound having ionicity, and 4 parts by mass of polyvinyl butyral ("S-LEC B BL-1" manufactured by SEKISUI CHEMICAL CO., LTD.) were used as the binder. Then, initial performance and permeability after ultrasonic washing was evaluated by using a method similar to that in Example B1. The following Table 5 shows manufacturing conditions. The following Table 6 shows evaluation results.

Example B22

A permeation test sheet was manufactured in a manner similar to that in Example B1 except that 2 parts by mass of polyaluminum chloride (manufactured by TAIMEI CHEMICALS Co., Ltd.) were added as the inorganic compound having ionicity, and 4 parts by mass of polyvinyl butyral ("S-LEC B BL-1" manufactured by SEKISUI CHEMICAL CO., LTD.) were used as the binder. Then, initial performance and permeability after ultrasonic washing was evaluated by using a method similar to that in Example B1. The following Table 5 shows manufacturing conditions. The following Table 6 shows evaluation results.

Example B23

A permeation test sheet was manufactured in a manner similar to that in Example B1 except for using a surface coating material obtained by mixing and sufficiently dispersing 2.5 parts by mass of a nitrogen-containing fluorine compound synthesized in Synthetic Example 1 as the oil-repellent hydrophilic agent, 2.5 parts by mass of organic bentonite ("ESBEN W" manufactured by HOJUN., Co. Ltd.) as the inorganic compound having charges, 9 parts by mass of polyvinyl butyral ("S-LEC B BL-1" manufactured by SEKISUT CHEMICAL CO., LTD.) as the binder, and 86 parts by mass of ethanol as the solvent, at the above proportion. Then, initial performance and permeability after ultrasonic washing was evaluated by using a method similar to that in Example B1. The following Table 5 shows manufacturing conditions. The following Table 6 shows evaluation results.

Example B24

A permeation test sheet was manufactured in a manner similar to that in Example B1 except that 0.5 parts by mass of fluororesin (PTFE) particles (powder of 0.3 μm manufactured by Kitamura Ltd.) were used as the fluororesin particle, and 4 parts by mass of polyvinyl butyral (S-LEC B BH-3 manufactured by SEKISUI CHEMICAL CO., LTD.) were used as the binder. Then, initial performance and permeability after ultrasonic washing was evaluated by using a method similar to that in Example B1. The following Table 5 shows manufacturing conditions. The following Table 6 shows evaluation results.

Example B25

A permeation test sheet was manufactured in a manner similar to that in Example B1 except that 2 parts by mass of a nitrogen-containing fluorine compound synthesized in Synthetic Example 14 were used as the oil-repellent hydrophilic agent, 10 parts by mass of fluororesin (PTFE) particles (powder of 0.3 μm manufactured by Kitamura Ltd.) were used as the fluororesin particle, and 4 parts by mass of polyvinyl butyral (S-LEC B BH-3 manufactured by SEKISUI CHEMICAL CO LTD.) was used as the binder. Then, initial performance and permeability after ultrasonic washing was evaluated by using a method similar to that in Example B1. The following Table 5 shows manufacturing conditions. The following Table 6 shows evaluation results.

Comparative Example B1

Commercial polypropylene nonwoven fabric (basis weight of 72 g/m$^2$, thickness of 0.26 mm, and hydrophilicity: E (hydrophobicity)) was used as the base. A surface coating material was manufactured by using the polyester nonwoven fabric. In the surface coating material, 2 parts by mass of polyvinyl butyral (S-LEC B BL-1 manufactured by SEKISUI CHEMICAL CO., LTD.) as the binder, and 98 parts by mass of ethanol as the solvent were mixed at the above proportion, and were sufficiently dispersed without mixing the oil-repellent hydrophilic agent.

Then, the base was coated with the manufactured surface coating material by using the above-described method. Thus, a permeation test sheet in Example A9 was manufactured, and then initial performance and permeability after ultrasonic washing was evaluated by using a method similar to that in Example B1. The following Table 5 shows manufacturing conditions. The following Table 6 shows evaluation results.

Comparative Example B2

Commercial polypropylene nonwoven fabric (basis weight of 72 g/m$^2$, thickness of 0.26 mm, and hydrophilicity: E (hydrophobicity)) was used as the base. A surface coating material was manufactured by using the polyester nonwoven fabric. In the surface coating material, 20 parts by mass of polyvinyl butyral (S-LEC B BL-1 manufactured by SEKISUI CHEMICAL CO., LTD.) as the binder, and 80 parts by mass of ethanol as the solvent were mixed at the above proportion, and were sufficiently dispersed without mixing the oil-repellent hydrophilic agent.

Then, the base was coated with the manufactured surface coating material by using the above-described method. Thus, a permeation test sheet was manufactured, and then initial performance of permeability was evaluated by using a method similar to that in Example B1. The following Table 5 shows manufacturing conditions. The following Table 6 shows evaluation results.

Comparative Example B3

Commercial polypropylene nonwoven fabric (basis weight of 72 g/m$^2$, thickness of 0.26 mm, and hydrophilicity: E (hydrophobicity)) was used as the base. A surface coating material was manufactured by using the polyester nonwoven fabric. In the surface coating material, 2 parts by mass of fumed silica ("AEROSIL 300" manufactured by JAPAN AEROSIL corporation) as the inorganic compound having charges, 2 parts by mass of polyvinyl butyral (S-LEC B BH-3 manufactured by SEKISUI CHEMICAL CO., LTD.) as the binder, and 98 parts by mass of ethanol as the solvent were mixed at the above proportion, and were sufficiently dispersed without mixing the oil-repellent hydrophilic agent.

Then, the base was coated with the manufactured surface coating material by using the above-described method. Thus, a permeation test sheet was manufactured in a manner similar to that in Example B1, and then initial performance and permeability after ultrasonic washing was evaluated by using a method similar to that in Example B1. The following Table 5 shows manufacturing conditions. The following Table 6 shows evaluation results.

Comparative Example B4

Commercial polypropylene nonwoven fabric (basis weight of 72 g/m$^2$, thickness of 0.26 mm, and hydrophilicity: E (hydrophobicity)) was used as the base. A surface coating material was manufactured by using the polyester nonwoven fabric. In the surface coating material, 2 parts by mass of organosilica sol ("IPA-ST" manufactured by NISSAN CHEMICAL INDUSTRIES. LTD.) were added as the inorganic compound having charges, and 2 parts by mass of polyvinyl butyral (S-LEC B BL-1 manufactured by SEKISUI CHEMICAL CO., LTD.) as the binder, and 91.3 parts by mass of ethanol as the solvent were mixed at the above proportion, and were sufficiently dispersed without mixing the hydrophilic and oil-repellent agent.

Then, the base was coated with the manufactured surface coating material by using the above-described method. Thus, a permeation test sheet in Example A9 was manufactured, and then initial performance and permeability after ultrasonic washing was evaluated by using a method similar to that in Example B1. The following Table 5 shows manufacturing conditions. The following Table 6 shows evaluation results.

TABLE 5A

| | Surface coating material | | | | | | | | Surface | |
| --- | --- | --- | --- | --- | --- | --- | --- | --- | --- | --- |
| | Nitrogen-containing fluorine compound | | binder | Inorganic compound/ fluororesin fine particle | solvent | Basis | | | coating material adhering amount | Weight increase ration after |
| | | [part by mass] | [part by mass] | [part by mass] | [part by mass] | Base Hydrophilicity | weight [g/m²] | Thickness [mm] | (solid) [g/m²] | treatment [%] |
| Example B1 | Synthetic Example 1 | 2.0 | UC-3000 4.0 | — | ethanol 94.0 | polypropylene nonwoven fabric B | 72 | 0.26 | 17.2 | 21.7 |
| Example B2 | | 0.5 | BL-1 0.5 | — | ethanol 98.0 | polyester nonwoven fabric A | 80 | 0.40 | 4.6 | 5.4 |
| Example B3 | | 2.0 | BH-3 4.0 | — | ethanol 94.0 | vinylon nonwoven fabric B | 100.1 | 0.30 | 12.9 | 12.7 |
| Example B4 | | 2.0 | BH-3 4.0 | — | ethanol 94.0 | pulp-polyester mixed nonwoven fabric B | 73.5 | 0.20 | 8.8 | 11.9 |
| Example B5 | | 2.0 | BH-3 4.0 | — | ethanol 94.0 | vinylon-cellulose mixed nonwoven fabric A | not shown | not shown | 7.7 | 21.4 |
| Example B6 | Synthetic Example 2 | 2.0 | BH-3 4.0 | — | ethanol 94.0 | polypropylene nonwoven fabric B | 72 | 0.26 | 14.8 | 20.6 |
| Example B7 | Synthetic Example 18 | 2.0 | BH-3 4.0 | — | ethanol 94.0 | polypropylene nonwoven fabric B | 72 | 0.26 | 15.9 | 22.1 |
| Example B8 | Synthetic Example 12 | 2.0 | BL-1 20.0 | — | methanol 78.0 | polypropylene nonwoven fabric B | 72 | 0.26 | 62.1 | 86.3 |
| Example B9 | Synthetic Example 15 | 2.0 | BH-3 4.0 | — | ethanol 94.0 | polypropylene nonwoven fabric A | 40 | 0.09 | 7.2 | 18.0 |
| Example B10 | Synthetic Example 3 | 2.0 | — | — | ethanol 98.0 | polyester nonwoven fabric A | 80 | 0.40 | 6.3 | 7.4 |

TABLE 5B

| | Surface coating material | | | | | | | | Surface | |
| --- | --- | --- | --- | --- | --- | --- | --- | --- | --- | --- |
| | Nitrogen-containing fluorine compound | | binder | Inorganic compound/ fluororesin fine particle | solvent | Basis | | | coating material adhering amount | Weight increase ration after |
| | | [part by mass] | [part by mass] | [part by mass] | [part by mass] | Base Hydrophilicity | weight [g/m²] | Thickness [mm] | (solid) [g/m²] | treatment [%] |
| Example B11 | Synthetic Example 7 | 2.0 | — | — | ethanol 98.0 | polyester nonwoven fabric A | 80 | 0.40 | 9.1 | 9.8 |
| Example B12 | | 2.0 | polyvinyl alcohol 4.0 | — | water 94.0 | nylon mesh C | not shown | 0.12 | not determined | 3.6 |
| Example B13 | Synthetic Example 9 | 2.0 | BH-3 4.0 | AEROSIL 300 0.5 | ethanol 94.0 | polypropylene nonwoven fabric B | 72 | 0.26 | 19.2 | 25.0 |
| Example B14 | Synthetic Example 1 | 2.0 | BL-1 2.0 | AEROSIL 300 2.0 | ethanol 94.0 | polypropylene nonwoven fabric B | 72 | 0.26 | 16.1 | 21.0 |
| Example B15 | | 3.0 | Z-410 4.0 | AEROSIL 300 3.0 | water 90.0 | polyester nonwoven fabric A | 80 | 0.40 | 40.0 | 50.0 |
| Example B16 | | 2.0 | BH-3 4.0 | AEROSIL 50 4.0 | ethanol 94.0 | polypropylene nonwoven fabric B | 72 | 0.26 | 40.8 | 54.0 |
| Example B17 | | 2.0 | BL-1 4.0 | Polytetsu 2.0 | ethanol 94.0 | polypropylene nonwoven fabric B | 72 | 0.26 | 48.0 | 61.3 |
| Example B18 | | 2.0 | BL-1 1.0 | organosilica sol 4.0 | ethanol 93.0 | polyester nonwoven fabric A | 80 | 0.40 | 24.9 | 29.3 |
| Example B19 | | 2.0 | BL-1 4.0 | organosilica sol 4.0 | hexafluoroxylene/ ethanol/n-butanol 94.0 | polyester nonwoven fabric A | 80 | 0.40 | 31.1 | 38.9 |
| Example B20 | | 2.5 | BL-1 7.5 | zeolite 13X 2.0 | ethanol 88.5 | polypropylene nonwoven fabric B | 72 | 0.26 | 32.2 | 41.9 |

TABLE 5C

| | Surface coating material | | | | | | | | Surface | |
| --- | --- | --- | --- | --- | --- | --- | --- | --- | --- | --- |
| | Nitrogen-containing fluorine compound | binder | Inorganic compound/ fluororesin fine particle | solvent | Basis | | | | coating material adhering amount | Weight increase ration after |
| | | [part by mass] | [part by mass] | [part by mass] | [part by mass] | Base Hydrophilicity | weight [g/m²] | Thickness [mm] | (solid) [g/m²] | treatment [%] |
| Example B21 | Synthetic Example 1 | 2.0 | BL-1 4.0 | aluminum sulfate 2.0 | ethanol 94.0 | polypropylene nonwoven fabric B | 72 | 0.26 | 17.8 | 22.6 |
| Example B22 | | 2.0 | BL-1 4.0 | polyaluminum chloride 2.0 | ethanol 94.0 | polypropylene nonwoven fabric B | 72 | 0.26 | 32.8 | 42.1 |
| Example B23 | | 2.5 | BL-1 9.0 | ESBEN W 2.5 | ethanol 86.0 | polypropylene nonwoven fabric B | 72 | 0.26 | 33.2 | 43.6 |
| Example B24 | | 2.0 | BH-3 4.0 | PTFE (0.3 µm) 0.5 | ethanol 94.0 | polypropylene nonwoven fabric B | 72 | 0.26 | 18.6 | 25.9 |
| Example B25 | Synthetic Example 14 | 2.0 | BH-3 4.0 | PTFE (0.3 µm) 10.0 | ethanol 94.0 | polypropylene nonwoven fabric B | 72 | 0.26 | 49.5 | 68.7 |
| Comparative Example B1 | | 0.0 | BL-1 2.0 | — | ethanol 98.0 | polypropylene nonwoven fabric E | 72 | 0.26 | 4.8 | 6.7 |
| Comparative Example B2 | | 0.0 | BL-1 20.0 | — | ethanol 80.0 | polypropylene nonwoven fabric E | 72 | 0.26 | 61.0 | 84.7 |
| Comparative Example B3 | | 0.0 | BH-3 2.0 | AEROSIL 300 2.0 | ethanol 98.0 | polypropylene nonwoven fabric E | 72 | 0.26 | 4.8 | 6.6 |
| Comparative Example B4 | | 0.0 | BL-1 2.0 | organosilica sol 2.0 | ethanol 91.3 | polypropylene nonwoven fabric E | 72 | 0.26 | 10.1 | 14.0 |

TABLE 6A

| | Initial performance | | After ultrasonic wave for 10 hours from | | After ultrasonic wave for 20 hours | | After ultrasonic wave for 30 hours | | After ultrasonic wave for 40 hours | | After ultrasonic wave for 60 hours | | After ultrasonic wave for 80 hours | |
| --- | --- | --- | --- | --- | --- | --- | --- | --- | --- | --- | --- | --- | --- | --- |
| | Hydro-philicity | Oil repel-lency | Hydro-philicity | Oil repel-lency | Hydro-philicity | Oil repel-lency | Hydro-philicity | Oil repel-lency | Hydro-philicity | Oil repel-lency | Hydro-philicity | Oil repel-lency | Hydro-philicity | Oil repel-lency |
| Example B1 | A | A | B | A | B | A | B~C | B | — | — | — | — | — | — |
| Example B2 | A | A | A | A | B | A | B~C 35 hours | A~B 35 hours | — | — | — | — | — | — |
| Example B3 | B | A | B | A~B | C | C | — | — | — | — | — | — | — | — |
| Example B4 | A | A | B | A~B | B~C 15 hours | C 15 hours | — | — | — | — | — | — | — | — |
| Example B5 | A | A | B~C | B | C 15 hours | C 15 hours | — | — | — | — | — | — | — | — |
| Example B6 | A | A | C | A | D 18 hours | B 18 hours | — | — | — | — | — | — | — | — |
| Example B7 | A | A | C | A~B | D 18 hours | B 18 hours | — | — | — | — | — | — | — | — |
| Example B8 | A | A | A~B | A | C~D 18 hours | B~C 18 hours | — | — | — | — | — | — | — | — |
| Example B9 | A | A | A | A | B | A~B | — | — | — | — | — | — | — | — |
| Example B10 | B | B | — | — | — | — | — | — | — | — | — | — | — | — |
| Example B11 | A | A | A | A | A | A | A | A | A | A | A~B 70 hours | A 70 hours | — | — |
| Example B12 | A | A | — | — | — | — | — | — | — | — | — | — | — | — |
| Example B13 | A | A | A | A | A~B | A~B | B | B~C | — | — | — | — | — | — |

TABLE 6A-continued

| | Initial performance | | After ultrasonic wave for 10 hours from | | After ultrasonic wave for 20 hours | | After ultrasonic wave for 30 hours | | After ultrasonic wave for 40 hours | | After ultrasonic wave for 60 hours | | After ultrasonic wave for 80 hours | |
|---|---|---|---|---|---|---|---|---|---|---|---|---|---|---|
| | Hydro-philicity | Oil repel-lency | Hydro-philicity | Oil repel-lency | Hydro-philicity | Oil repel-lency | Hydro-philicity | Oil repel-lency | Hydro-philicity | Oil repel-lency | Hydro-philicity | Oil repel-lency | Hydro-philicity | Oil repel-lency |
| Example B14 | A | A | A~B | A | A~B | A | A~B | A | A~B | A | B | A | B | A~B |
| Example B15 | A | A | B | A | B | A | B | A | B | B | C 50 hours | C 50 hours | — | — |
| Example B16 | A | A | B | A | B | A | B | A | B | A | B | B | B | B |
| Example B17 | B | A | A | A | B | A | B | A | B | A | B | C | — | — |

TABLE 6B

| | Initial performance | | After ultrasonic wave for 10 hours from | | After ultrasonic wave 20 hours | | After ultrasonic wave for 30 hours | | After ultrasonic wave for 40 hours | | After ultrasonic wave for 60 hours | | After ultrasonic wave for 80 hours | |
|---|---|---|---|---|---|---|---|---|---|---|---|---|---|---|
| | Hydro-philicity | Oil repel-lency | Hydro-philicity | Oil repel-lency | Hydro-philicity | Oil repel-lency | Hydro-philicity | Oil repel-lency | Hydro-philicity | Oil repel-lency | Hydro-philicity | Oil repel-lency | Hydro-philicity | Oil repel-lency |
| Example B18 | A | A | A | A | B | A | B 25 hours | A 25 hours | — | — | — | — | — | — |
| Example B19 | A | A | B | A | B | A | C | C | — | — | — | — | — | — |
| Example B20 | A | A | A~B | A | B | A | B | B | — | — | — | — | — | — |
| Example B21 | A | A | A | A | B | A | C 25 hours | A 25 hours | — | — | — | — | — | — |
| Example B22 | B | A | A | A | A~B | B | A~B 25 hours | C 25 hours | — | — | — | — | — | — |
| Example B23 | A | A | A~B | A | A~B | A | C | C | — | — | — | — | — | — |
| Example B24 | A | A | A | A | B | B | B~C 25 hours | B 25 hours | — | — | — | — | — | — |
| Example B25 | A | A | B | B | B | C | B | C | — | — | — | — | — | — |
| Comparative Example B1 | C | D | D 3 hours | D 3 hours | — | — | — | — | — | — | — | — | — | — |
| Comparative Example B2 | E | D | — | — | — | — | — | — | — | — | — | — | — | — |
| Comparative Example B3 | D~E | D | D 1 hours | D 1 hours | — | — | — | — | — | — | — | — | — | — |
| Comparative Example B4 | B | D | B | D | — | — | — | — | — | — | — | — | — | — |

As shown in Table 6, in the permeation test filter of Examples B1 to B25, the hydrophilicity in the initial performance was "A" to "B", and the oil repellent properties was "A" to "B". Each one showed exceptional hydrophilic and oil-repellent properties. In particular, in Examples B14 and B16, even after 80 hours elapsed from ultrasonic washing, the hydrophilicity was "B", and the oil repellent properties was "A" to "B". Any one showed exceptional hydrophilic and oil-repellent properties.

On the contrary, the permeation test filter in Comparative Examples B1 and B2 in which the base having hydrophobicity was coated with polyvinyl butyral did not show the hydrophilic and oil-repellent properties. The permeation test filter in Comparative Example B3 in which the base having hydrophobicity was coated with fumed silica and polyvinyl butyral did not also show the hydrophilic and oil-repellent properties. The permeation test filter in Comparative Example B4 in which the base having hydrophobicity was coated with organosilica sol and polyvinyl butyral showed the hydrophilicity, but did not show the oil repellent properties.

<Continuous Oil-Water Separation Test>

Example B26

Commercial polyester nonwoven fabric (basis weight of 131 g/m$^2$, thickness of 0.60 mm, permeation precision of 1 μm, and hydrophilicity: A) was cut off so as to have a circular shape having a diameter of 24 cm. The cut-off polyester nonwoven fabric was used as the base. Then, a surface coating material was prepared by using 0.6 mass % of a nitrogen-containing fluorine compound synthesized in Synthetic Example 1 as the oil-repellent hydrophilic agent, 1.2 mass % of polyvinyl butyral (S-LEC B BL-1 manufactured by SEKISUI CHEMICAL CO., LTD.), 0.3 mass % of organosilica sol ("IPA-ST" manufactured by NISSAN CHEMICAL INDUSTRIES. LTD.), and 97.9 mass % of a solvent (details: hexafluoroxylene/ethanol/n-butanol having a mass ratio of 12/8/1). Then, after the base was immersion-treated in the surface coating material, the base was dried at 120° C. for 17 hours (increased amount after drying: 0.747 g), thereby an oil-water separation filtration filter was produced.

The oil-water separation filtration filter was disposed on SUS steel of an intermediate flange portion of a cylindrical type resin container, and the flange was fastened and fixed. The cylindrical type resin container has an outer diameter of 21.6 cm, an inner diameter of 20.2 cm, and a height of 60 cm. The cylindrical type resin container includes a flange at an intermediate portion, includes an air vent under the flange, and includes an exit port for water on the bottom side.

Then, a liquid mixture of water and n-hexadecane, which was prepared at an amount ratio of 24:1 was put into a storage tank including a stirring machine. While stirring, the liquid mixture was supplied over the filter by a pump, and an oil-water separation test was performed at room temperature.

While an oil-water liquid mixture was supplied to the storage tank, permeation flux (unit: m$^3$/m$^2$·hr) per one liter was measured during a period when the total amount of water passing through the filter reaches the maximum 30 liters. The following Table 7 shows evaluation results.

Comparative Example B5

A filter was produced (increased amount after drying: 0.109 g) in a manner similar to that in Example B25 except that commercial polypropylene nonwoven fabric (basis weight of 40 g/m$^2$, thickness of 0.09 mm, and hydrophilicity: E (hydrophobicity)) was used, and the oil-repellent hydrophilic agent was not mixed. Then, the oil-water separation test was performed by a device similar to that in Example B25. The following Table 7 shows evaluation results.

TABLE 7

| | Item Accumulated passing water flow rate | Unit | Measurement result | | | | |
|---|---|---|---|---|---|---|---|
| | | L | 2 | 5 | 10 | 20 | 30 |
| Example B26 | Permeation flux | m$^3$/m$^2$·hr | 0.63 | 0.70 | 0.75 | 0.74 | 0.69 |

TABLE 7-continued

| | Item Accumulated passing water flow rate | Unit | Measurement result | | | | |
|---|---|---|---|---|---|---|---|
| | | L | 2 | 5 | 10 | 20 | 30 |
| Comparative Example B5 | Permeation flux | m$^3$/m$^2$·hr | — | — | — | — | — |

As shown in Table 7, it can be confirmed that the oil-water separation filtration filter in Example B26 can separate a solution mixture in which water and oil is mixed to each other, into moisture and oil, with high accuracy, and can continuously maintain permeation flux appropriate for a use, for a long term. When the passed water was visually observed, an oil film derived from n-hexadecane was not recognized.

On the contrary, when an oil-water liquid mixture was supplied to the filter in Comparative Example B5, water passing through the filter was not possible.

As described above, the followings can be confirmed. Compatibility between the base and the surface coating material is increased by using the hydrophilic base, and, even though coating with a surface coating material having low concentration is performed, the oil-repellent hydrophilic agent is firmly held in the base. Thus, it is possible to keep the oil-water separation effect.

Example B27

Polyester nonwoven fabric used in Example B2 was used as the base. A permeation test sheet was manufactured by using the fabric, in a manner similar to that in Example B1 except that 1 part by mass of a nitrogen-containing fluorine compound synthesized in Synthetic Example 1 was used as the oil-repellent hydrophilic agent, and 99 parts by mass of a liquid mixture of hexafluoroxylene/ethanol/n-butanol having a mass ratio of 12/8/1 was used as the solvent. Then, initial performance and permeability after ultrasonic washing was evaluated by using a method similar to that in Example 131. The following Table 8 shows manufacturing conditions. The following Table 9 shows evaluation results. "The surface coating material adhering amount (solid)" in Table 8 corresponds to the amount of solid of the surface coating material adhering to the base.

Example B28

Polyester nonwoven fabric used in Example B2 was used as the base. A permeation test sheet was manufactured by using the fabric, in a manner similar to that in Example 1 except that 1 part by mass of a nitrogen-containing fluorine compound synthesized in Synthetic Example 16 was used as the oil-repellent hydrophilic agent, and 99 parts by mass of a liquid mixture of hexafluoroxylene/ethanol/n-butanol having a mass ratio of 12/8/1 was used as the solvent. Then, initial performance and permeability after ultrasonic washing was evaluated by using a method similar to that in Example 1. The following Table 8 shows manufacturing conditions. The following Table 9 shows evaluation results.

Example B29

Polyester nonwoven fabric used in Example 2 was used as the base. A permeation test sheet was manufactured by using the fabric, in a manner similar to that in Example 1 except that 1 part by mass of a nitrogen-containing fluorine compound synthesized in Synthetic Example 17 was used as the oil-repellent hydrophilic agent, and 99 parts by mass of a liquid mixture of hexafluoroxylene/ethanol/n-butanol having a mass ratio of 12/8/1 was used as the solvent. Then, initial performance and permeability after ultrasonic washing was evaluated by using a method similar to that in Example 1. The following Table 8 shows manufacturing conditions. The following Table 9 shows evaluation results.

Example B30

Polyester nonwoven fabric used in Example 2 was used as the base. A permeation test sheet was manufactured by using the fabric, in a manner similar to that in Example 1 except that 2 parts by mass of a nitrogen-containing fluorine compound synthesized in Synthetic Example 19 was used as the oil-repellent hydrophilic agent, and 98 parts by mass of ethanol was used as the solvent. Then, initial performance and permeability after ultrasonic washing was evaluated by using a method similar to that in Example 1. The following Table 8 shows manufacturing conditions. The following Table 9 shows evaluation results.

As shown in Table 9, in the permeation test filter of Examples B27 to B30, the hydrophilicity in the initial performance was "A", and the oil repellent properties was "A". Any one showed exceptional hydrophilic and oil-repellent properties. In the permeation test filter of Examples B27 to B29, even after 30 hours elapsed from ultrasonic washing, the hydrophilicity was "A" to [C], and the oil repellent properties was [A] to [C]. The hydrophilic and oil-repellent properties were shown. In particular, in the permeability test filter of Examples B28 and B29, even after 70 hours elapsed from ultrasonic washing, the hydrophilicity was "A" to [B], and the oil repellent properties were "A" to [B]. The hydrophilic and oil-repellent properties were shown.

INDUSTRIAL APPLICABILITY

In the filter medium according to the present invention, the hydrophilic and oil-repellent properties are applied to the surface of the channel in the base. The filter medium has exceptional water permeability, anti-fouling properties, or easy washing properties. Thus, the filter medium may be applied to an oil-water separation filter medium and the like. The water treatment module and the water treatment device

TABLE 8

| | Surface coating material | | | | | | | Surface | |
| --- | --- | --- | --- | --- | --- | --- | --- | --- | --- |
| | Nitrogen-containing fluorine compound | binder | Inorganic compound/ fluororesin fine particle | solvent | Base Hydrophilicity | Basis weight [g/m$^2$] | Thickness [mm] | coating material adhering amount (solid) [g/m$^2$] | Weight increase ratio after treatment [%] |
| | [part by mass] | [part by mass] | [part by mass] | [part by mass] | | | | | |
| Example B27 | Synthetic Example 1 | 1.0 | — | — | hexafluoroxylene/ ethanol/ n-butanol 99.0 | polyester nonwoven fabric A | 80 | 0.40 | 8.0 | 6.1 |
| Example B28 | Synthetic Example 16 | 1.0 | — | — | hexafluoroxylene/ ethanol/ n-butanol 99.0 | polyester nonwoven fabric A | 80 | 0.40 | 7.2 | 5.8 |
| Example B29 | Synthetic Example 17 | 1.0 | — | — | hexafluoroxylene/ ethanol/ n-butanol 99.0 | polyester nonwoven fabric A | 80 | 0.40 | 6.6 | 5.5 |
| Example B30 | Synthetic Example 19 | 2.0 | — | — | ethanol 98.0 | polyester nonwoven fabric A | 80 | 0.40 | 6.0 | 7.0 |

TABLE 9

| | Initial performance | | After ultrasonic wave for 10 hours | | After ultrasonic wave for 20 hours | | After ultrasonic wave for 30 hours | | After ultrasonic wave for 40 hours | | After ultrasonic wave for 60 hours | | After ultrasonic wave for 80 hours | |
| --- | --- | --- | --- | --- | --- | --- | --- | --- | --- | --- | --- | --- | --- | --- |
| | Hydro- philicity | Oil repel- lency | Hydro- philicity | Oil repel- lency | Hydro- philicity | Oil repel- lency | Hydro- philicity | Oil repel- lency | Hydro- philicity | Oil repel- lency | Hydro- philicity | Oil repel- lency | Hydro- philicity | Oil repel- lency |
| Example B27 | A | A | A | A | B | A~B | B~C | B~C | — | — | — | — | — | — |
| Example B28 | A | A | A | A | A | A | A | A | A | A | A~B 70 hours | A~B 70 hours | — | — |
| Example B29 | A | A | A | A | A | A | A | A | A | A | A | A | A~B | A~B |
| Example B30 | A | A | B | C | — | — | — | — | — | — | — | — | — | — | according to the present invention can be used as an oil-water separation filter and an oil-water separation device, for example, when treatment of discharged water which contains oil discharged from a general house, an industrial facility, public utilities, a factory, and the like is performed, an oil collection work by spillage of oil to a river, the ocean, and the like occurring by an accident and the like is performed, and non-aqueous oil is removed from water accompanying in the oil field, which is one type of oil-containing discharged water in oil drilling.

The invention claimed is:

1. A filter medium which uses a liquid containing oil and water as a separation target, and has a channel for the liquid, the medium comprising:
    a base constituting the channel; and
    one or more of nitrogen-containing fluorine compounds which are provided on at least a portion of a surface of the channel and are represented by the following formulas (1) to (4),

[Chemical Formula 1]

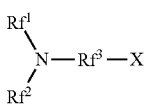
(1)

[Chemical Formula 2]

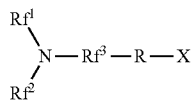
(2)

[Chemical Formula 3]

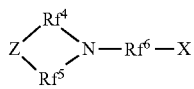
(3)

[Chemical Formula 4]

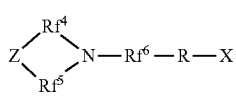
(4)

wherein, in the formulas (1) and (2), each of $Rf^1$ and $Rf^2$ is a straight-chain or branched perfluoroalkyl group which is the same as or different from each other, and has 1 to 6 carbon atoms, and $Rf^3$ is a straight-chain or branched perfluoroalkylene group which has 1 to 6 carbon atoms;
in the formulas (3) and (4), each of $Rf^4$, $Rf^5$, and $Rf^6$ is a straight-chain or branched perfluoroalkylene group which is the same as or different from each other, and has 1 to 6 carbon atoms, and Z includes any of an oxygen atom, a nitrogen atom, a $CF_2$ group, and a CF group;
in the formulas (2) and (4), R is a linking group which is a bivalent organic group; and
in the formulas (1) to (4), X is
    an anion type hydrophilicity imparting group having "—$CO_2M^1$", "—$OSO_3M^1$", "—$OP(OH)O_2M^1$", "—$OPO_3M^1{}_2$", "=$O_2PO_2M^1$", or "—$PO(OH)_x(OM^1)_{2-y}$," ($M^1$ indicates alkali metal, alkaline-earth metal, Mg, and Al, and $R^1R^2R^3R^4N^+$; $R^1$ to $R^4$ indicate straight chain or branched alkyl groups which are independent from each other, and have hydrogen atoms or 1 to 20 carbon atoms; and y indicates an integer of 0 to 2), or
    a cation type hydrophilicity imparting group having "—$N^+R^5R^6R^7$.Cl—", "—$N^+R^5R^6R^7$.Br—", "—$N^+R^5R^6R^7$.I—", "—$N^+R^5R^6R^7$.$CH_3SO_3{}^-$", "—$N^+R^5R^6R^7$.$R^7SO_4{}^-$", "—$N^+R^5R^6R^7$.$NO_3{}^-$", "(—$N^+R^5R^6R^7)_2CO_3{}^{2-}$", or "(—$N^+R^5R^6R^7)_2SO_4{}^{2-}$" at the termination ($R^5$ to $R^7$ are straight chain or branched alkyl groups which are independent from each other, and have hydrogen atoms or 1 to 20 carbon atoms), or
    an amphoteric type hydrophilicity imparting group having "—$N^+R^8R^9(CH_2)_nCO_2{}^-$", a sulfobetaine type of "—$N^+R^8R^9(CH_2)_nSO_3{}^-$", an amine oxide type of "—$N^+R^8R^9O^-$", or a phosphobetaine type of "—$OPO_3{}^-(CH_2)_nN^+R^8R^9R^{10}$" at the termination (n is an integer of 1 to 5, $R^8$ and $R^9$ indicates an alkyl group having a hydrogen atom or 1 to 10 carbon atoms, and $R^{10}$ indicates an alkyl group having a hydrogen atom or 1 to 10 carbon atoms or an alkylene group having 1 to 10 carbon atoms).

2. The filter medium according to claim 1, wherein the one or more of nitrogen-containing fluorine compounds are bonded to the surface of the channel by one or both of an organic binder and an inorganic binder.

3. The filter medium according to claim 2, wherein the organic binder contains any of a thermoplastic resin, a thermoplastic elastomer, a thermosetting resin, and an UV curable resin.

4. The filter medium according to claim 2, wherein the inorganic binder contains any of a silane compound and water glass.

5. The filter medium according to claim 1, wherein the base is a fiber assembly, and the channel is configured by a gap between fibers.

6. The filter medium according to claim 5, wherein the fiber includes an organic fiber selected from a group consisting of synthetic fiber, natural fiber, and cellulosic fiber, or an inorganic fiber selected from a group consisting of metallic fiber, carbon fiber, glass fiber, and ceramics fiber.

7. The filter medium according to claim 1, wherein the base is an aggregate of particles, and the channel is configured by a gap between the particles.

8. The filter medium according to claim 7, wherein the particle includes an inorganic particle selected from a group consisting of anthracite, sand, gravel, garnet, glass, ceramics, and metal.

9. The filter medium according to claim 1, wherein the base is a porous medium having a continuous pore, and the channel is configured by the continuous pore.

10. The filter medium according to claim 9, wherein the porous medium is an organic porous medium selected from a group consisting of porous fluororesin, porous polypropylene, porous polyethylene, porous polyester, porous polysulfone, porous polyethersulfone, porous vinylon, porous nylon, porous polyvinyl alcohol, porous vinyl copolymer containing polyalkylene oxide chain, and porous cellulose, or an inorganic porous medium selected from a group consisting of active carbon, ceramics, sintered metal, silica, alumina, zeolite, calcium carbonate, and clay mineral.

11. The filter medium according to claim 1, wherein the width of the channel is 0.1 to 180 μm.

12. A method for producing the filter medium according to claim 1, the method comprising:

a process of preparing a coating liquid in which one or more nitrogen-containing fluorine compounds represented by the formulas (1) to (4) are dispersed or dissolved in water, an organic solvent, or a solvent mixture of water and an organic solvent;

a process of coating at least a portion of the surface of the base with the coating liquid in which the nitrogen-containing fluorine compound is dispersed or dissolved; and a process of removing a dispersion medium or a solvent by drying, and forming a coating film on at least a portion of the surface of the base.

13. The method for producing a filter medium according to claim 12, wherein the coating liquid contains an organic binder or an inorganic binder.

14. A water treatment module comprising:

the filter medium according to claim 1.

15. A water treatment device comprising:

the water treatment module according to claim 14.

* * * * *